(12) United States Patent
Kim et al.

(10) Patent No.: US 7,426,040 B2
(45) Date of Patent: Sep. 16, 2008

(54) CHIP-SCALE OPTICAL SPECTRUM ANALYZERS WITH ENHANCED RESOLUTION

(75) Inventors: Hong Koo Kim, Pittsburgh, PA (US); Zhijun Sun, Pittsburgh, PA (US); Yun Suk Jung, Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 449 days.

(21) Appl. No.: 11/206,900

(22) Filed: Aug. 19, 2005

(65) Prior Publication Data

US 2006/0209413 A1 Sep. 21, 2006

Related U.S. Application Data

(60) Provisional application No. 60/602,623, filed on Aug. 19, 2004.

(51) Int. Cl.
*G01B 9/02* (2006.01)

(52) U.S. Cl. .................................. 356/519; 977/932

(58) Field of Classification Search .............. 356/519, 356/521, 454, 480; 977/932, 949–951
See application file for complete search history.

(56) References Cited

U.S. PATENT DOCUMENTS

| | | | |
|---|---|---|---|
| 4,410,454 A * | 10/1983 | Faschingbauer | ............ 502/306 |
| 4,659,429 A | 4/1987 | Isaacson et al. | |
| 4,662,747 A | 5/1987 | Isaacson et al. | |
| 4,815,854 A | 3/1989 | Tanaka et al. | |
| 4,891,830 A | 1/1990 | Iwahashi | |
| 4,997,278 A | 3/1991 | Finlan et al. | |
| 5,202,939 A * | 4/1993 | Belleville et al. | ............. 385/12 |
| 5,250,812 A | 10/1993 | Murai et al. | |
| 5,306,902 A | 4/1994 | Goodman | |
| 5,351,127 A | 9/1994 | King et al. | |
| 5,354,985 A | 10/1994 | Quate | |
| 5,359,681 A | 10/1994 | Jorgenson et al. | |
| 5,451,980 A | 9/1995 | Simon et al. | |
| 5,455,594 A | 10/1995 | Blasing et al. | |

(Continued)

FOREIGN PATENT DOCUMENTS

| WO | WO 2004/023499 A1 | 3/2004 |
|---|---|---|
| WO | WO 2004/097894 A2 | 11/2004 |
| WO | WO 2005/017570 A2 | 2/2005 |

OTHER PUBLICATIONS

Li Pira et al., Modelling and experimental evidence of quantum phenomena in metallic non-continuous films, May 31, 2001, Proc. of 2nd euspen International Conference—Turin, Italy, pp. 212-215.*

(Continued)

*Primary Examiner*—Patrick Connolly
*Assistant Examiner*—Scott M Richey
(74) *Attorney, Agent, or Firm*—Foley & Lardner LLP

(57) ABSTRACT

A Fabry-Perot cavity filter includes a first mirror and a second mirror. A gap between the first and the second mirror monotonically varies as a function of width of the filter. This filter may be used with photodetector and a channel selection filter in an optical device, such as a spectrum analyzer. The channel selection filter may be a metal nanooptic filter array which includes plurality of subwavelength apertures in a metal film or between metal islands.

24 Claims, 51 Drawing Sheets

U.S. PATENT DOCUMENTS

| | | | |
|---|---|---|---|
| 5,550,373 | A | 8/1996 | Cole et al. |
| 5,570,139 | A | 10/1996 | Wang |
| 5,633,972 | A | 5/1997 | Walt et al. |
| 5,647,030 | A | 7/1997 | Jorgenson et al. |
| 5,663,798 | A | 9/1997 | Karrai |
| 5,666,195 | A * | 9/1997 | Shultz et al. ............... 356/519 |
| 5,784,507 | A * | 7/1998 | Holm-Kennedy et al. ..... 385/31 |
| 5,789,742 | A | 8/1998 | Wolff |
| 5,835,645 | A | 11/1998 | Jorgenson et al. |
| 5,864,641 | A | 1/1999 | Murphy et al. |
| 5,933,233 | A | 8/1999 | Gunther |
| 5,946,083 | A | 8/1999 | Melendez et al. |
| 5,973,316 | A * | 10/1999 | Ebbesen et al. ............. 250/216 |
| 5,986,808 | A | 11/1999 | Wang |
| 6,014,251 | A * | 1/2000 | Rosenberg et al. .......... 359/350 |
| 6,040,936 | A | 3/2000 | Kim et al. |
| 6,044,981 | A * | 4/2000 | Chu et al. ................... 210/490 |
| 6,052,238 | A | 4/2000 | Ebbesen et al. |
| 6,097,456 | A | 8/2000 | Wang |
| 6,111,248 | A | 8/2000 | Melendez et al. |
| 6,147,756 | A | 11/2000 | Zavracky et al. |
| 6,151,114 | A * | 11/2000 | Russell ........................ 356/519 |
| 6,191,847 | B1 | 2/2001 | Melendez et al. |
| 6,236,033 | B1 | 5/2001 | Ebbesen et al. |
| 6,282,005 | B1 | 8/2001 | Thompson et al. |
| 6,285,020 | B1 | 9/2001 | Kim et al. |
| 6,326,004 | B1 | 12/2001 | Greve et al. |
| 6,441,298 | B1 | 8/2002 | Thio |
| 6,514,936 | B1 | 2/2003 | Greve et al. |
| 6,525,880 | B2 | 2/2003 | Flanders et al. |
| 6,539,156 | B1 | 3/2003 | Dickson et al. |
| 6,797,405 | B1 | 9/2004 | Coe et al. |
| 7,319,560 | B2 * | 1/2008 | Gunning et al. ............. 359/578 |
| 2003/0123125 | A1 * | 7/2003 | Little .......................... 359/290 |
| 2003/0128949 | A1 | 7/2003 | Kitagawa et al. |
| 2003/0173501 | A1 | 9/2003 | Thio et al. |
| 2005/0068541 | A1 * | 3/2005 | Gunning et al. ............. 356/519 |
| 2005/0161589 | A1 | 7/2005 | Kim et al. |
| 2005/0175939 | A1 * | 8/2005 | Perlo et al. .................. 430/322 |
| 2006/0039009 | A1 * | 2/2006 | Kiesel et al. ................ 356/519 |
| 2006/0083350 | A1 * | 4/2006 | Gerndt et al. ................ 378/70 |

OTHER PUBLICATIONS

Sakai et alia, "Metallic Mesh Bandpass Filters and Fabry-Perot Interferometer for the Far Infrared," Aug. 1969, Japanese Journal of Applied Physics, vol. 8, No. 8, pp. 1046-1055.*

Hogeveen and van de Stadt, "Fabry-Perot interferometers with three mirror," Nov. 15, 1986, Applied Optics, vol. 25, No. 22, pp. 4181-4184.*

Takunori Ito et al., "Photonic bands of metallic systems. II. Features of surface plasmon polaritons", Physical Review B. vol. 64, 045117-1-045117-8, Jul. 9, 2001.

P.W. Barber, "Surface-Enhanced Electric Intensities on Large Silver Spheroids", Physical Review Letters vol. 50, No. 13, Mar. 28, 1983, pp. 997-1000.

M. M. J. Treacy, "Dynamical diffraction explanation of the anomalous transmission of light through metallic gratings", Physical Review B 66, 2002, 195105-1-195105-11.

T. López-Rios et al., "Surface Shape Resonances in Lamellar Metallic Gratings", Physical Review Letters, vol. 81, No. 3, Jul. 20, 1998, pp. 665-668.

Principles of Optics—Electromagnetic theory of propagation, interference and diffraction of light, Max Born et al., Cambridge University Press, 1999.

T.W. Ebbesen et al., "Extraordinary optical transmission through sub-wavelength hole arrays", Nature, vol. 391, Feb. 1998, pp. 667-669.

H.F. Ghaemi et al., "Surface plasmons enhance optical transmission through subwavelength holes", Physical Review B., vol. 58, No. 11, Sep. 15, 1998, pp. 6779-6782.

A. Degiron et al., "Effects of hole depth on enhanced light transmission through subwavelength hole array", Applied Physics Letters, vol. 81, No. 23, Dec. 2, 2002, pp. 4327-4329.

L. Martín-Moreno et al., "Theory of Extraordinary Optical Transmission through Subwavelength Hole Arrays", Physical Review Letters, vol. 86, No. 6, Feb. 5, 2001, pp. 1114-1117.

E. Altewischer et al., "Plasmon-assisted transmission of entangled photons", Nature, vol. 418, Jul. 18, 2002, pp. 304-306.

H. J. Lezec et al., "Beaming Light from a Subwavelength Aperture", Science, vol. 297, Aug. 2, 2002, pp. 820-822.

L. Martín-Moreno et al., "Theory of Highly Directional Emission from a Single Subwavelength Aperture Surrounded by Surface Corrugations", Physical Review Letters, vol. 90, No. 16, pp. 167401-1-167401-4, Apr. 25, 2003.

William L. Barnes et al., "Surface plasmon subwavelength optics", Nature, vol. 424, Aug. 14, 2003, pp. 824-830.

U. Schröter et al., "Surface-plasmon-enhanced transmission through metallic gratings", Physical Review B, vol. 58, No. 23, pp. 15419-15421, Dec. 15, 1998.

J.A. Porto et al., "Transmission Resonances on Metallic Gratings with Very Narrow Slits", Physical Review Letters, vol. 83, No. 14, Oct. 4, 1999, pp. 2845-2848.

S. Astilean et al., "Light transmission through metallic channels much smaller than the wavelength", Optics Communications, 175 (2000), 265-273.

F.J. Garcia-Vidal et al., "Transmission and focusing of light in one-dimensional periodically nanostructured metals", Physical Review B, 66, (2002) 155412-1-155412-10.

F.J. Garcia-Vidal et al., "Multiple Paths to Enhance Optical Transmission through a Single Subwavelength Slit", Physical Review Letters, vol. 90, No. 21, May 30, 2003, pp. 213901-1-213901-4.

Zhijun Sun et al., "Role of Surface Plasmons in the Optical interaction in Metallic Gratings with Narrow Slits", Applied Physics Letters, vol. 83, No. 15, Oct. 13, 2003, pp. 3021-3023.

F.J. Garcia-Vidal et al., "Focusing light with a single subwavelength aperture flanked by surface corrugations", Applied Physics Letters, vol. 83, No. 22, pp. 4500-4502, Dec. 1, 2003.

D.E. Grupp et al., "Crucial role of metal surface in enhanced transmission through subwavelength apertures", Applied Physics Letters, vol. 77, No. 11, Sep. 11, 2000, pp. 1569-1571.

Zhijun Sun et al., "Growth of ordered, single-domain, alumina nanopore arrays with holographically patterned aluminum films", Applied Physics Letters, vol. 81, No. 18, Oct. 28, 2002, pp. 3458-3460.

A. Degiron et al., "Effects of Hole Depth on Enhanced Light Transmission Through Subwavelength Hole Arrays", Applied Physics Letters, vol. 81, No. 23, Dec. 2, 2002, pp. 4327-4329.

Tineke Thio et al., "Giant optical transmission of sub-wavelength apertures: physics and applications", Institute of Physics Publishing, Nanotechnology 13 (2002) pp. 429-432.

T. W. Ebbesen et al., "Extraordinary Optical Transmission Through Sub-Wavelength Hole Arrays", Nature, vol. 391, Feb. 12, 1998, pp. 667-669.

A. Krishnan et al., "Evanescently coupled resonance in surface plasmon enhanced transmission", Optics Communications 200 (2001) pp. 1-7.

Tae Jin Kim et al., "Control of optical transmission through metals perforated with subwavelength hole arrays", Optics Letters, vol. 24, No. 4, Feb. 15, 1999, pp. 256-258.

W. L. Barnes et al., "Physical origin of photonic energy gaps in the propagation of surface plasmons on gratings", Physical Review B, vol. 54, No. 9, pp. 6227-6244, Sep. 1, 1996.

H. F. Ghaemi et al., "Surface Plasmons Enhance Optical Transmission Through Subwavelength Holes", Physical Review B, vol. 58, No. 11, Sep. 15, 1998, pp. 6779-6782.

F. J. Garcia-Vidal et al., "Transmission and focusing of light in one-dimensional periodically nanostructured metals", Physical Review B, The American Physical Society, 66, 155412-1-155412-10, 2002.

M. M. J. Treacy, "Dynamical diffraction explanation of the anomalous transmission of light through metallic gratings", Physical Review B, 66, 195105-1-195105-11, 2002.

T, Lôpez-Rios et al., "Surface Shape Resonances in Lamellar Metallic Gratings", Physical Review Letters, vol. 81, No. 3, pp. 665-668, (1998).

Qing Cao et al., "Negative Role of Surface Plasmons in the Transmission of Metallic Gratings with Very Narrow Slits", Physical Review Letters, vol. 88, No. 5, pp. 057403-1-057403-4, (2002).

J.A. Porto et al., "Transmission Resonances on Metallic Gratings with Very Narrow Slits", Physical Review Letters, vol. 83, No. 14, pp. 2845-2848 (1999).

L. Martin-Moreno et al., "Theory of Extraordinary Optical Transmission through Subwavelength Hole Arrays", Physical Review Letters, vol. 86, No. 6, pp. 1114-1117, (2001).

Zhijun Sun et al., "Refractive transmission of light and beam shaping with metallic nano-optic lenses", Applied Physics Letters, vol. 85, No. 4, pp. 1-4, (2002).

Zhijun Sun et al., "Role of surface plasmons in the optical interaction in metallic gratings with narrow slits", Applied Physics Letters, vol. 83, No. 15, pp. 3021-3023, (2003).

Hong Koo Kim et al. "Nano-Optic Chip Technology", Proceedings of the 2th International Workshop on Advanced Materials for Information Technology and Applications: Organic/Inorganic Nanoelectronics and Nanophotonics, pp. 21-26, (2004).

M. Delaide et al., "Design and Application of Low-Frequency Twin Side-by-Side Phased Array Transducers for Improved UT Capability on Cast Stainless Steel Components", NDT.net, vol. 5, No. 10, (2003) http://www.ndt.net/article/v05n10/versp/versp.htm.

William L. Barnes et al., "Surface Plasmon Subwavelength Optics", Nature, vol. 424, pp. 824-830, (2003).

J.A. Wahl et al., "Tapered-Fabry-Pérot Filters," IEEE Photonics Technology Letters, vol. 16, No. 8 (Aug. 2004).

Z. Sun et al., "Dynamic evolution of surface plasmon resonances in metallic nanoslit arrays," Applied Physics Letters, 86, 023111, 3 pgs. (2005).

* cited by examiner

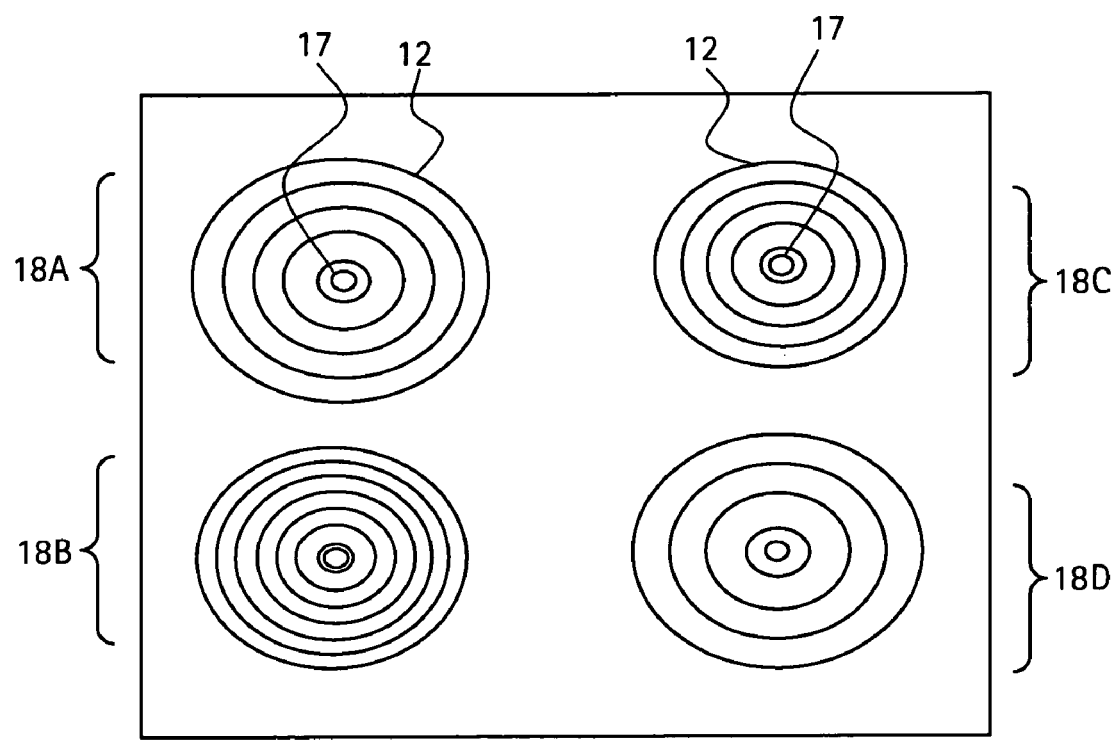

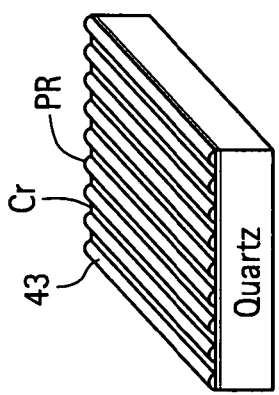
FIG. 9D
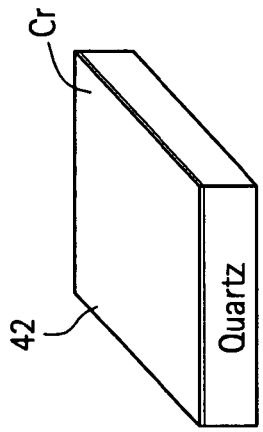
FIG. 9E
FIG. 9F
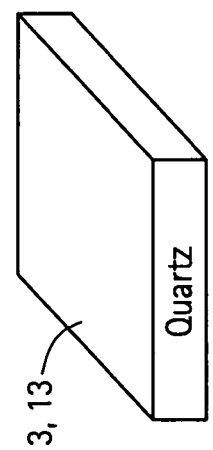
FIG. 9G
FIG. 9H
FIG. 9I $T = T_1 \times T_2$

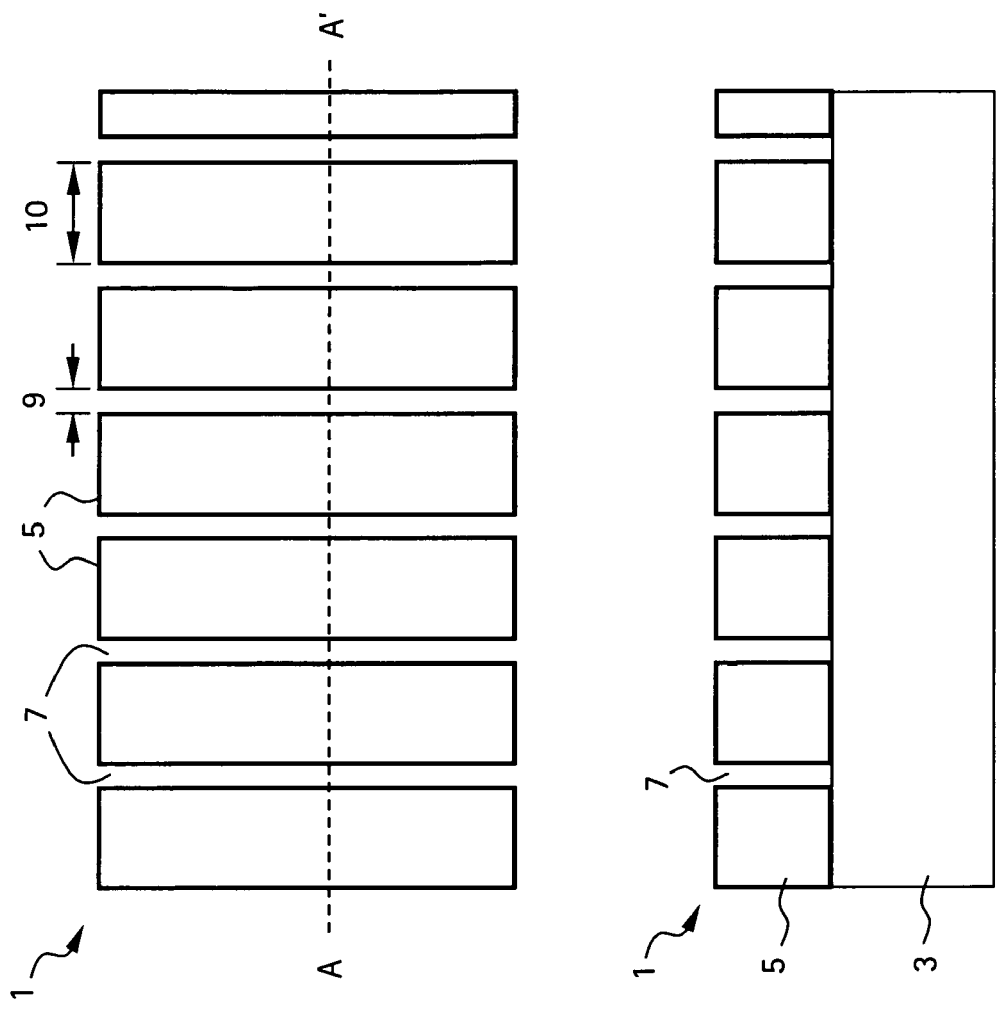

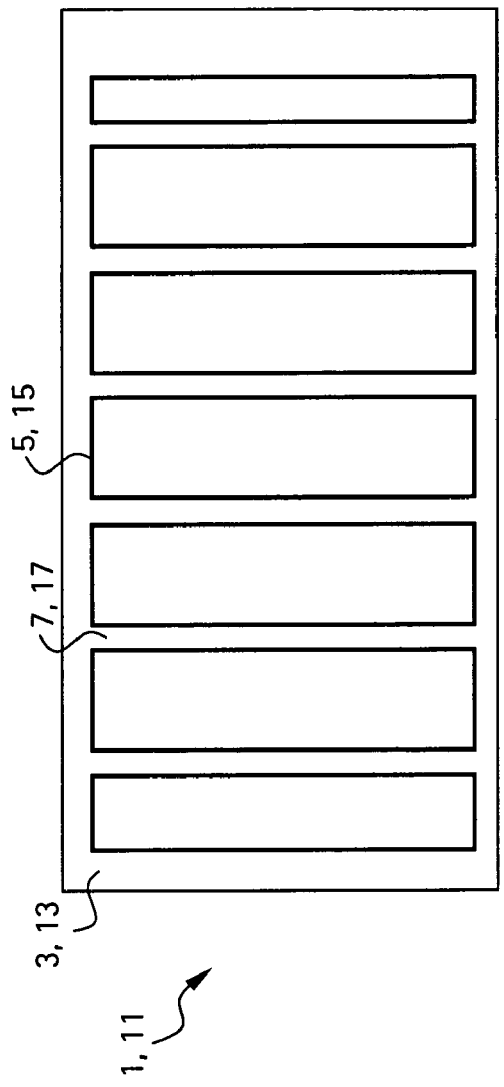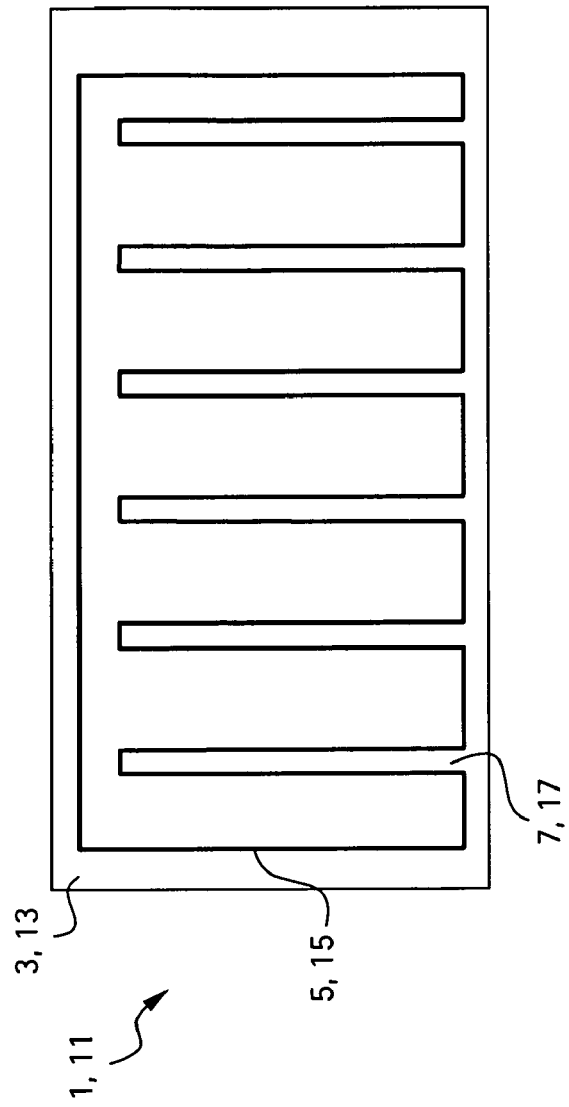

chirped grating period constant grating period

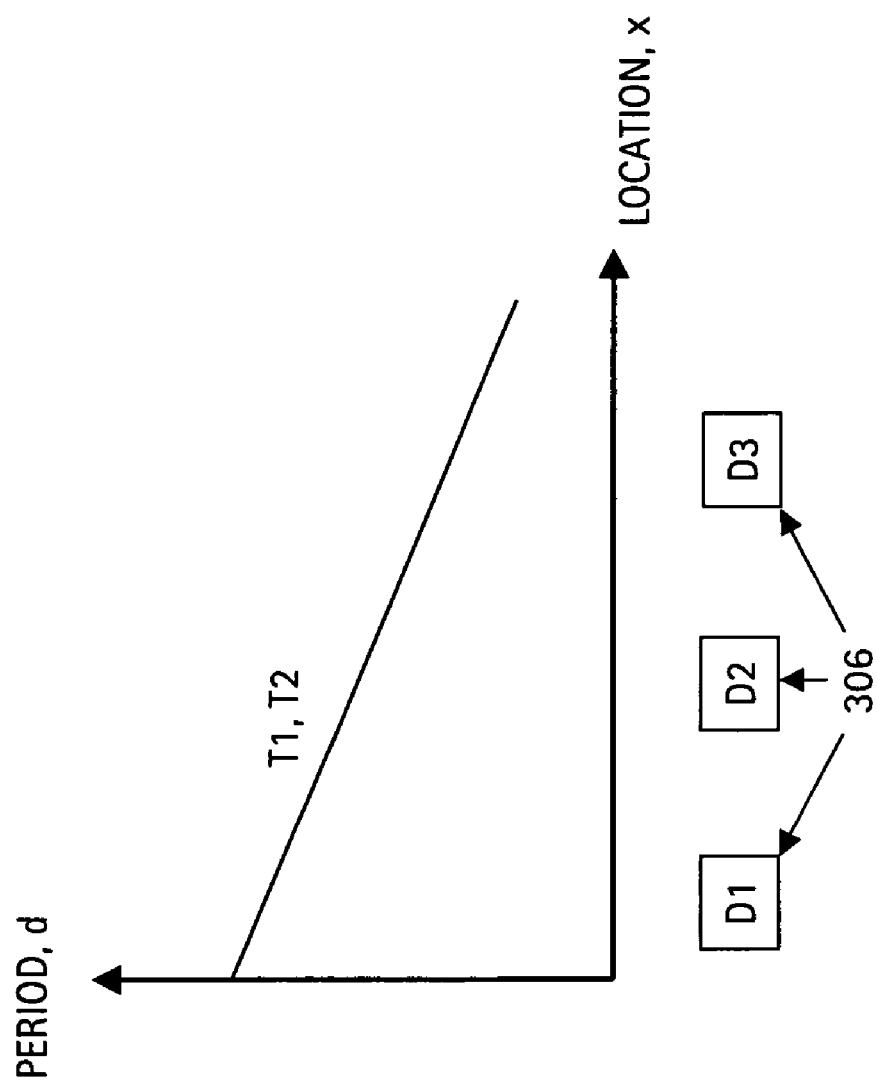

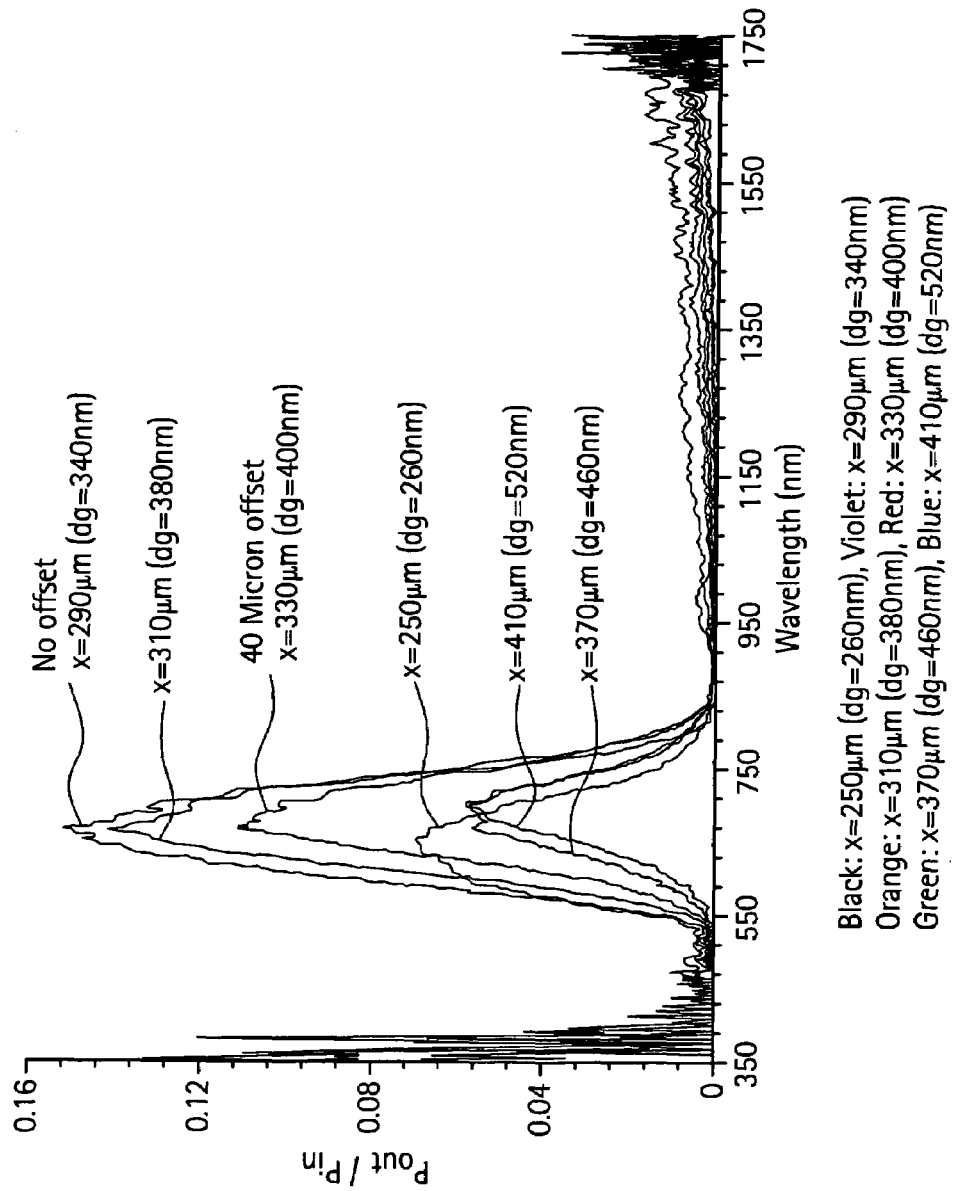

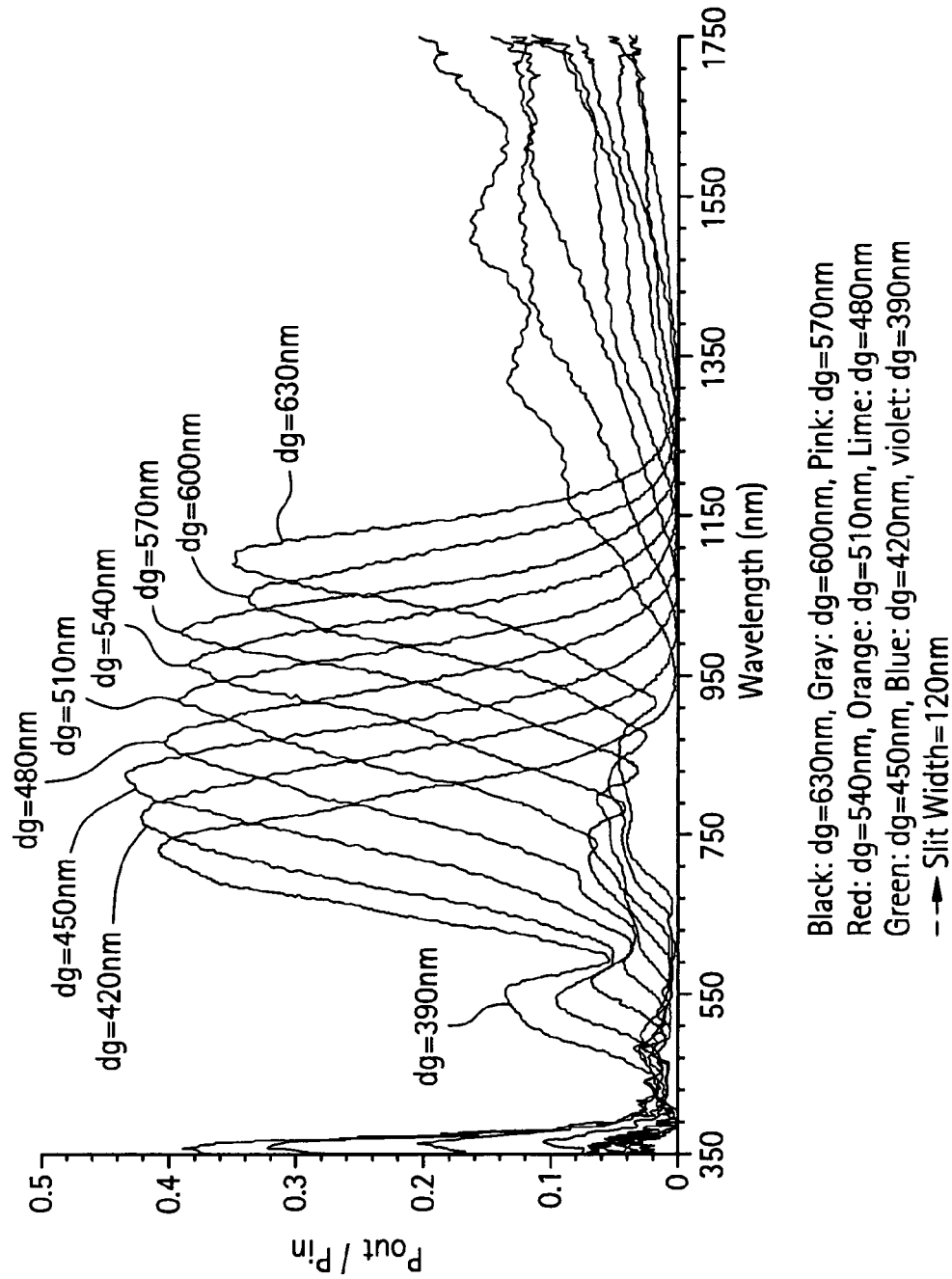

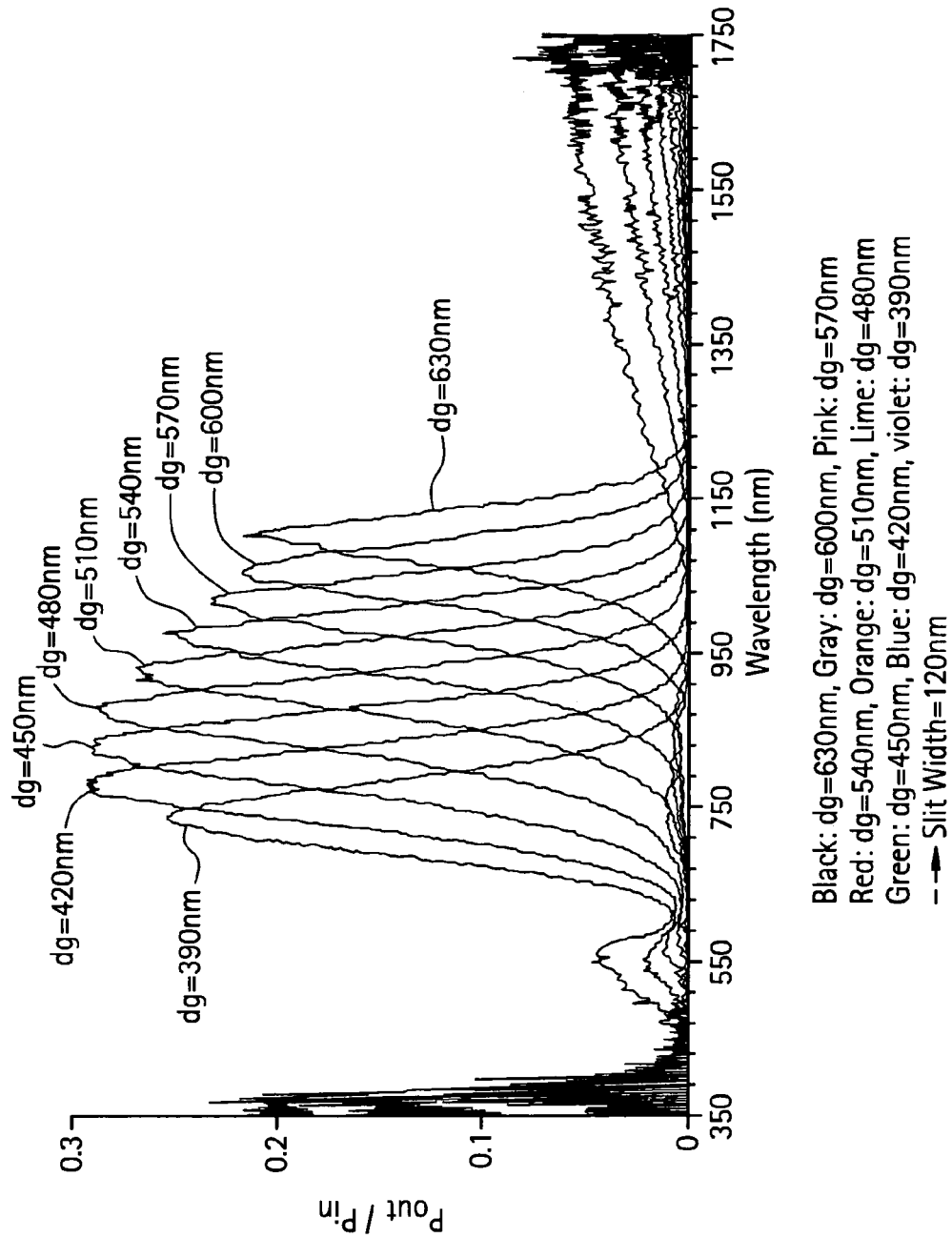

Transmission of light through a Ag/PR/Ag Cavity

Simulation

Transmission of light through a Ag/PR/Ag Cavity

Simulation

CHIP-SCALE OPTICAL SPECTRUM ANALYZERS WITH ENHANCED RESOLUTION

CROSS-REFERENCE TO RELATED PATENT APPLICATIONS

This application claims benefit of priority of U.S. Provisional Application Ser. No. 60/602,623, filed on Aug. 19, 2004 and is incorporated herein by reference in its entirety.

The U.S. government may have certain rights in this invention pursuant to grant number 00014-99-0663 from the Office of Naval Research and grant number ECS-0403865 from the National Science Foundation.

FIELD OF THE INVENTION

The present invention is directed generally to optical devices and more particularly to nanostructured optical devices and methods of making the devices.

BACKGROUND OF THE INVENTION

According to classical optics, transmission of light through a sub-wavelength aperture in a metal film is extremely small when its diameter d is significantly smaller than the wavelength $\lambda$, and is predicted to follow the Bethe limit $T/f \sim (d/\lambda)^4$, where T/f denotes the transmission normalized to the area occupied by the aperture. Recently it has been reported in U.S. Pat. Nos. 5,973,316 and 6,236,033 and in Nature, Vol. 391, pp. 667-669, all incorporated herein by reference in the entirety, that extremely high transmission through sub-wavelength aperture(s) in a metal film can be obtained when the incident light is resonant with surface plasmon in the metal film.

BRIEF DESCRIPTION OF THE DRAWINGS

FIGS. 2A, 2B, 2C and 2E are top views of devices according to the preferred embodiments of the present invention.

FIGS. 9D-9I are schematic three dimensional views of a method of making a device according to the preferred embodiments of the present invention.

FIG. 19A is a schematic top view of a device according to an embodiment of the present invention.

FIG. 19B is a side cross sectional view across line A-A' in FIG. 19A.

FIGS. 23 and 24 are schematic top views of devices according to the preferred embodiments of the present invention.

FIG. 35A is a schematic plot of grating period versus location on the detector for the device of example 12. FIG. 35B is a plot of transmission spectra for the device of example 12.

FIGS. 36A and 36B are plots of transmission spectra for the device of example 13 and 14.

DETAILED DESCRIPTION OF THE PREFERRED EMBODIMENTS

Figure 37A:
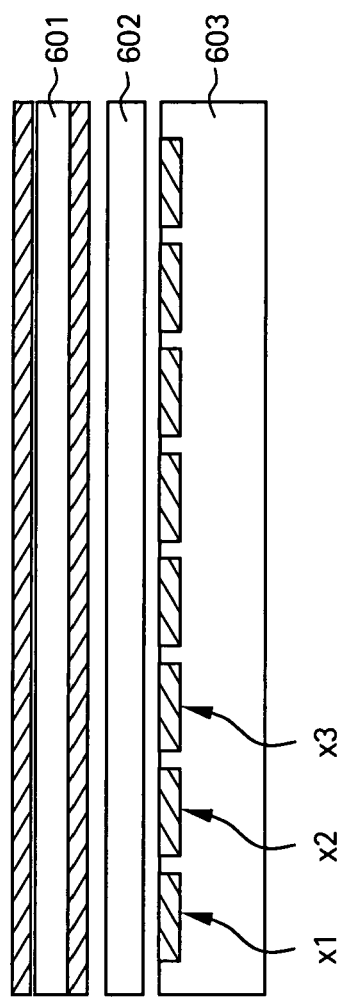
FIGS. 37A, 37B and 38 are schematic diagrams of a system containing a Fabry-Perot cavity filter and a channel selection filter array.

FIG. 37A illustrates a system that can provide significantly enhanced resolution of about $\lambda/50$ or less, such $\lambda/100$ or less (i.e., the resolution is the incident wavelength of light $\lambda$ divided by 100, for example about 10 nm resolution or band width for 1000 nm wavelength radiation). The system comprises three parts: a line selection filter array 601 that can provide passband width of about $\lambda/100$ or less, a channel selection filter array 602 that can provide pass bandwidth of about $\lambda/10$ or less, and a photodetector array 603 such as CCDs, CMOS image sensors, or focal plane arrays.

Figure 37B:
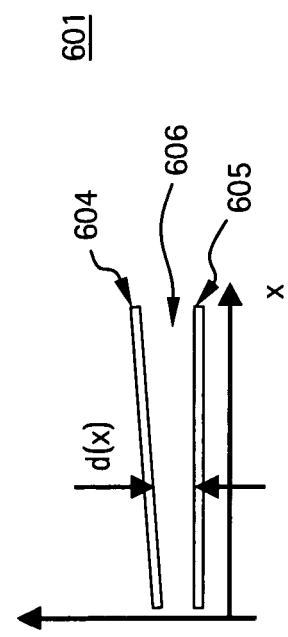
Figure 38:
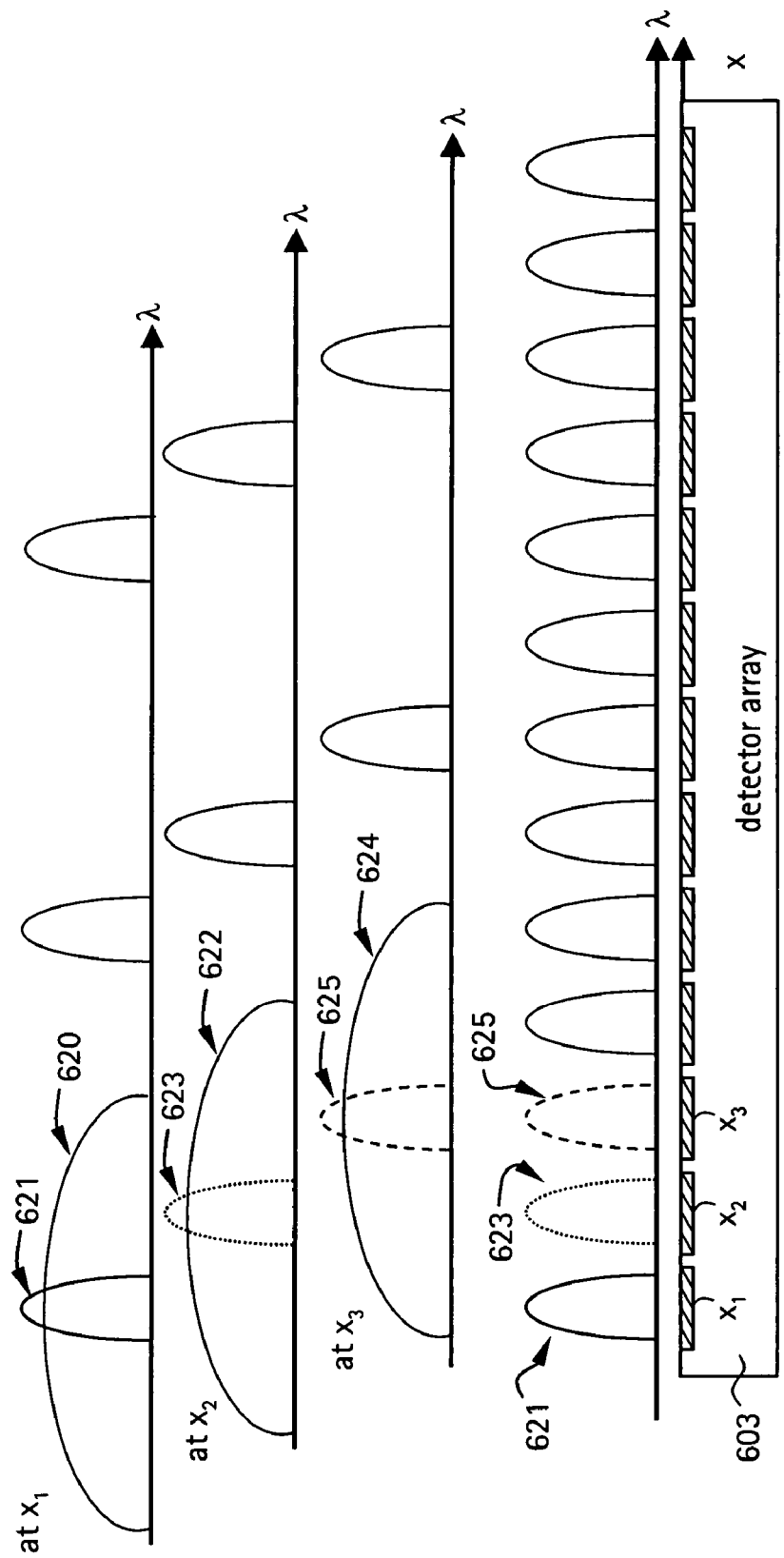

The concept of high-resolution spectral analysis is illustrated in the diagram shown in FIG. 38. One preferred narrow line selection filter 601 is a Fabry-Perot cavity structure or filter. FIG. 37B schematically illustrates the filter 601, which comprises two mirrors 604, 605 separated by a gap or cavity 606. A transmission spectrum of a Fabry-Perot cavity structure usually shows multiple peaks with narrow passband width. The spacing between neighboring peaks is primarily determined by the gap 606 between the two mirrors 604, 605 that form a cavity and a dielectric function of the material sandwiched in the cavity. The spectral width of a Fabry-Perot resonance peak is mainly determined by the reflectivity of the two mirrors, and can be designed to be less than $\lambda/100$. In the configuration of FIGS. 37A, 37B and 38, the mirror spacing (i.e., gap 606 between the mirrors 604, 605 or cavity length or height, "d") is variable along the photodetector array 603 direction or width ("x"). Preferably, the mirror spacing of the Fabry-Perot cavity filter 601 varies monotonically along (i.e., as a function of) the array 603 direction (i.e., along or as function of the filter 601 width direction), preferably in a continuous fashion along the array direction. In other words, the cavity height of the filter 601 is tapered either in a continuous or stepped fashion. Thus, as shown in FIGS. 37 and 38, different photodetectors x1, x2, x3 of the array 603 are located in locations which correspond to different cavity length or height ("d" in FIG. 1). Thus, each photodetector of the array 603 is adapted to detect a different peak wavelength transmitted through the Fabry-Perot filter 601.

This continuously-tuned, variable-gap Fabry-Perot cavity structure can be easily implemented by tilting one of the two mirrors with proper angle and separation. This can be accomplished by forming a tapered spacer material in the cavity. The tapered spacer material is thicker on one end than the other end. For example, the spacer material 606 may have one "flat" or "horizontal" side and one "tilted" or "diagonal" side, as shown in FIG. 37B. In another example, both the "upper" and "lower" spacer sides may be "tilted" or "diagonal" such that the spacer material has a trapezoid-like shape rotated by 90 degrees. The directional terms above are provided in quotes because they are described with respect to the structure being positioned horizontally. However, it should be understood that the structure may be positioned vertically or in any other suitable orientation. Alternatively, the mirror tilting can be accomplished by raising one end of a mirror slightly higher than the opposite end of the same mirror in case the cavity lacks a spacer material. Any suitable materials may be used. For example, the mirrors may be silver or multi-period $SiO_2/TiO_2$ mirrors. The spacer material may be glass ($SiO_2$) or air. Other optically transmissive materials may also be used. The Fabry-Perot cavity structure 601 thus has a wavelength tenability and a spatial and temporal (static and dynamic) passband width of about $\lambda/50$ or less, such $\lambda/100$ or less, such as about $\lambda/50$ to about $\lambda/100$.

The Fabry-Perot transmission peaks continuously shift to a certain direction as a function of location along the array (and thus of gap between mirrors). Depending on the spectral range of interest, only one Fabry-Perot peak in a relatively narrow wavelength span may be observed. However, in the case of relatively wide span, multiple Fabry-Perot peaks usually appear. Thus, the channel selection filter array 602 is used to select only one peak transmitted through the Fabry-Perot cavity filter 601 and to filter out all other peaks. Thus, in order to achieve narrow bandpass filtering, whose center wavelength is designed to vary along the array direction, an array of relatively wide bandpass filters (i.e., the channel selection filter array 602) is used. The filters 601 and 602 are optically coupled to each other such that an incident radiation beam passes through both filters before reaching the detector 603 or an observer (i.e., the filters 601 and 602 are either physically attached to each other, either directly or indirectly, or are not attached to each other, but are positioned such that an incident radiation beam passes through both filters). As shown in FIG. 37A, filter 602 is located between filter 601 and detector 603. However, filter 601 may be located between filter 602 and detector 603, if desired. It should be noted that the Fabry-Perot cavity structure 601 described above does not necessarily have to be used with a channel selection filter 602 and detector 603, but may be used alone or in combination with other suitable devices for any suitable applications, including but not limited to the ones described herein The bandpass or channel selection filter 602 may comprise a nano-optic filter array (i.e., wavelength separation device) described below with reference to FIGS. 1-36C. The channel selection filter array is designed such that spectral location of each bandpass filter is to match the desired Fabry-Perot peak in the wavelength domain and its passband width is small enough to filter out all other unwanted peaks, as shown in FIG. 38. The bandpass or channel selection filter array 602 is also designed such that the spatial location of each filter is aligned to each pixel (i.e., photodetector) of a detector array. For example, the array 602 may have a chirped grating period and may be suitable for polarization detection, as will be described in more detail below. The bandpass characteristic of a nano-optic filter 602 is mainly determined by the structural parameters of the nano-aperture array, as will be described below. A single layer of nano-optic filter typically shows passband width of about $\lambda/10$ (where $\lambda$ is the wavelength of light). This corresponds to about 100-200 nm in the visible to near-infrared range. While the nanooptic filter 602 based on plasmon resonance through holes or slits in a metal layer described below with respect to FIGS. 1-36C is preferred, any other suitable bandpass filters, including thin film filters based on dielectric materials, may be used instead in the system shown in FIG. 37.

In FIG. 38, the top spectral profiles show the transmission spectra of the Fabry-Perot cavity filter 601 and the nano-optic filter 602, respectively, measured at the location of the first pixel (x1, the leftmost one) of a detector array 603. The nano-optic channel selection filter 602 that is aligned to overlap with the first pixel area x1 offers only one passband 620 (broader one in the diagram), and this allows selection of one narrow Fabry-Perot peak 621 among many. Similarly, the second profiles at x2 correspond to the spectra of the filter components that fall on the second pixel of a detector. Overall, an array of bandpass filters with narrow passband can be implemented on top of a detector array (the bottom profile with many closely spaced narrow bands). In other words, in FIG. 38, each horizontal line represents what is detected at each particular pixel or detector (x1, x2, x3). The narrow bands 621, 623, 625 are the main and sideband peaks that are transmitted through the filter 601. The wide bands 620, 622, 624 represent the passband wavelengths of the filter 602. Thus, the filter 602 blocks all peaks transmitted through filter 601 except for one, such as the main peak or one of the sideband peaks. Thus, the passband ranges of each filter 602 are shifted in wavelength with respect to different detectors or pixels, as will be described in more detail below.

The system described above with respect to FIGS. 37-38 may be used in any device or method described below, such as analyte detection, color camera or spectrum analyzer. The system offers a number of unique advantages. First, the number of channels is easily scalable while maintaining high resolution. Pixel size of photodetectors (CCDs, CMOS imagers or focal plane arrays) is typically 5-10 micron and an array size greater than 1000 is commercially available. The nanooptic filters 602 also offer good scalability in their physical dimension, well matching the range of detector pixel size. Another important aspect of the nano-optic filter arrays is that the filter characteristic is primarily determined/designed by the lateral structure of a nanoslit array (such as grating period), unlike the case of conventional thin-film filters that require deposition of many layers of dielectric films with precisely controlled film thickness. This allows great flexibility and control and high throughput in designing and implementing a large number of filters on a small footprint in an integrated fashion with a simple fabrication process. The line selection filters 601 are designed independent from the channel selection filters 602, and this also allows great flexibility in developing high-resolution spectrum analyzers on a chip scale configuration.

Figure 39A:
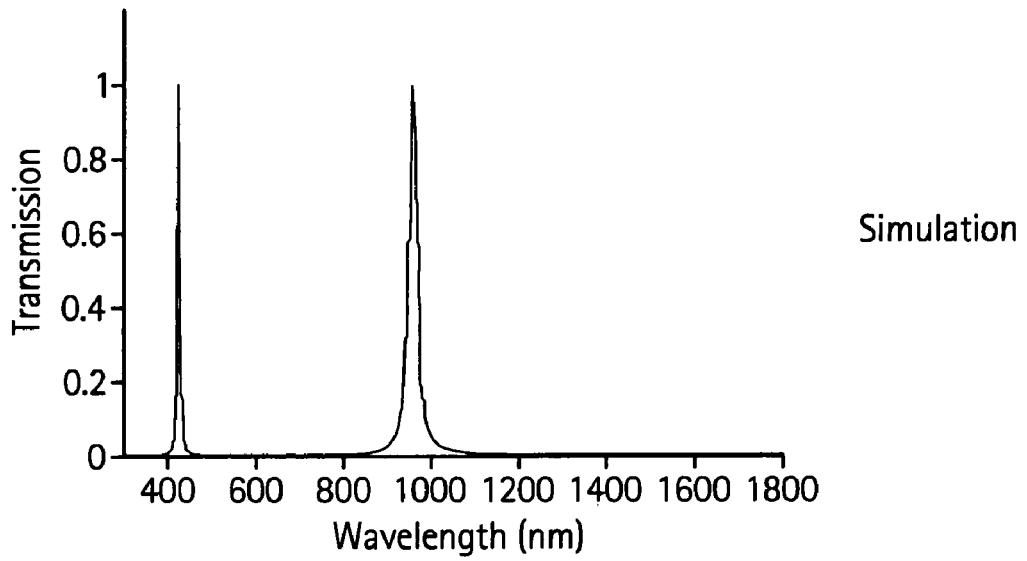
FIGS. 39A, 39B, 39C, 39D, 40 and 41 illustrate exemplary spectra for such systems.
Figure 39B:
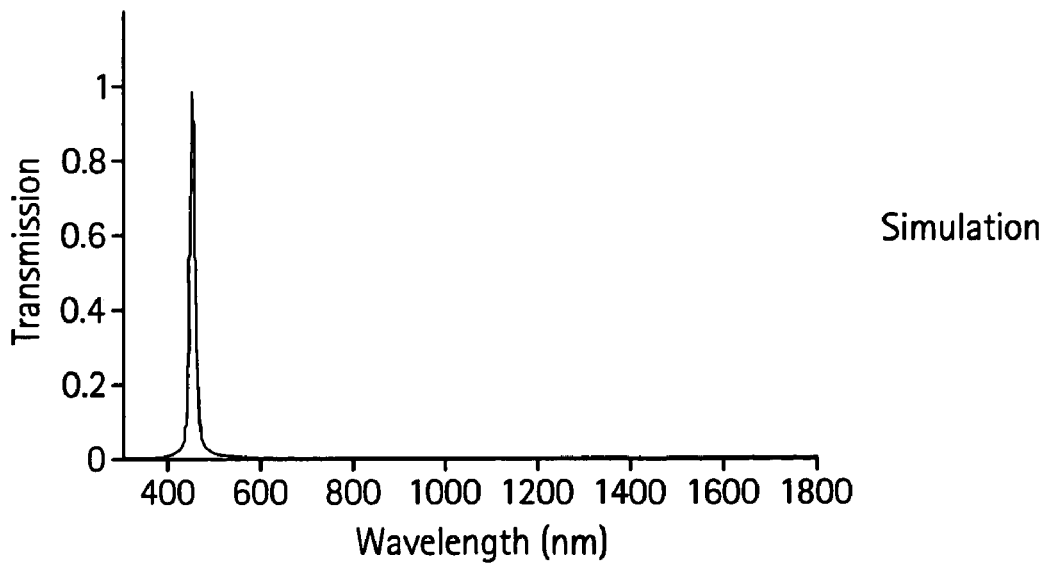
Figure 39C:
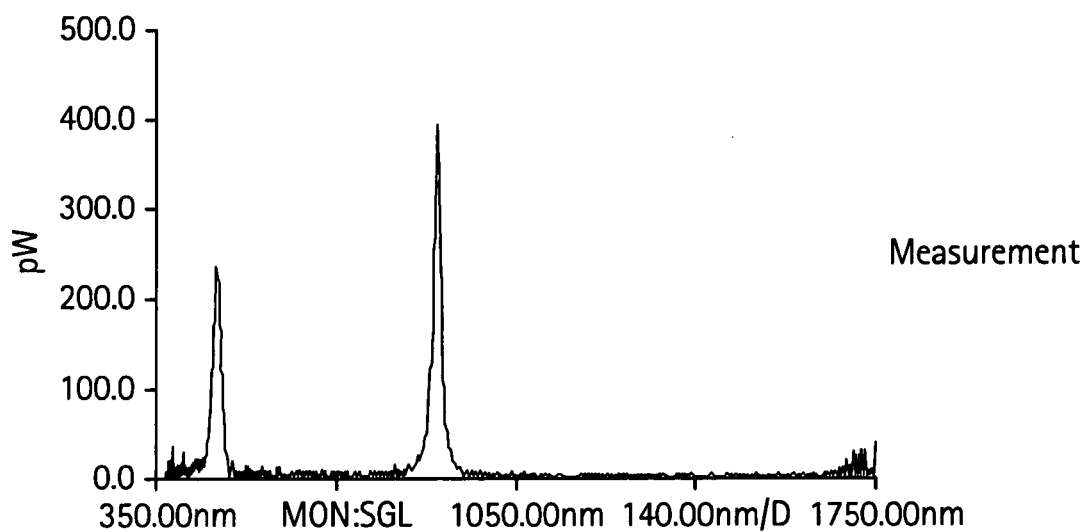
Figure 39D:
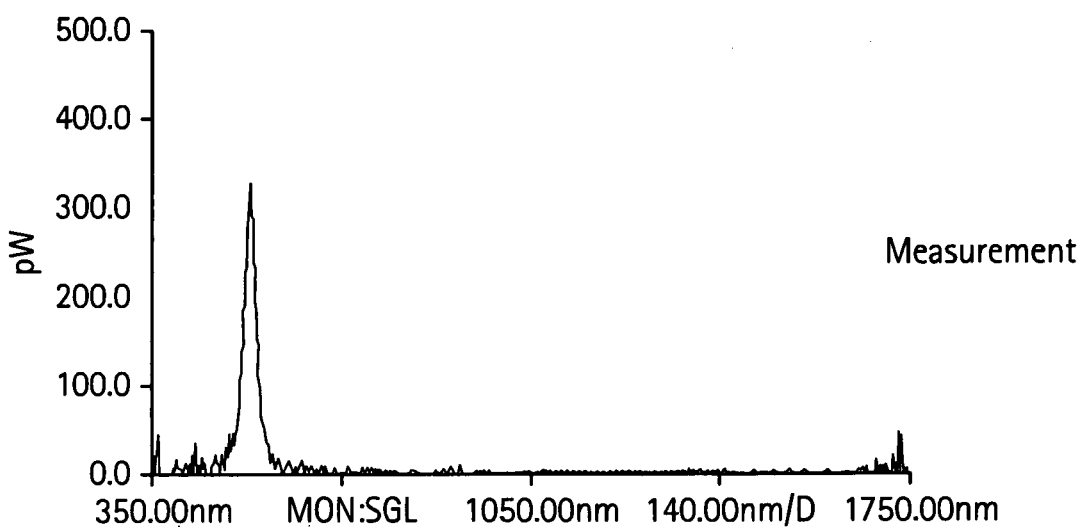

FIGS. 39A and 39B illustrate simulated and FIGS. 39C and 39D illustrate measured transmission spectra of a planar Fabry-Perot cavity. The dimensions of the device whose spectra is shown in FIG. 39C are as follows: silver mirror (30 nm thick)/photoresist spacer (210 nm thick)/silver mirror (70 nm thick)/quartz substrate. The dimensions of the device whose spectra is shown in FIG. 39D are as follows: silver mirror (30 nm thick)/photoresist spacer (95 nm thick)/silver mirror (70 nm thick)/quartz substrate. FIGS. 39A and 39B are simulations on the spectra from the devices of FIGS. 39C and 39D, respectively, described above. In the simulation, the dielectric constant of gap material (photoresist) is assumed to be 1.8-1.6 for wavelengths of 300-1800 nm.

Figure 40:
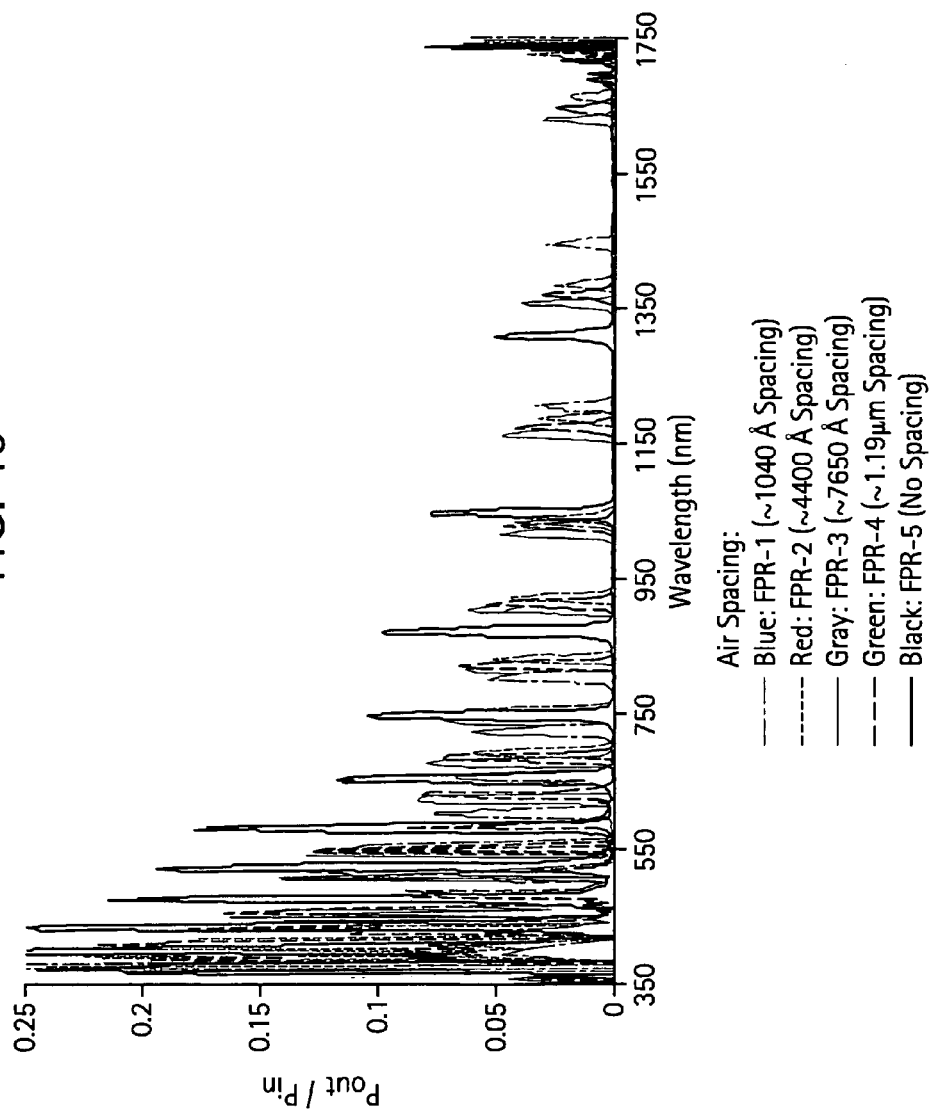

FIG. 40 shows a plot of transmission intensity ($P_{out}/P_{in}$) versus wavelength for different planar Fabry-Perot resonant cavity devices with Ag mirrors. Specifically, FIG. 40 shows the transmission spectra of five different devices, each with a uniform, fixed gap between the mirrors. The dimensions of each device are as follows: quartz substrate/silver mirror (370 A)/air gap (0, 1040 A, 4400 A, 7650 A, or 1.19 micron thickness, respectively, for each device)/silver mirror (370 A)/quartz substrate. As shown in FIG. 40, the transmission through the cavity is detected as the positions corresponding to cavity height (i.e., mirror spacing "d") of about zero, about 1040 Angstroms, about 4400 Angstroms, about 7650 Angstroms and about 1.19 microns. As can been seen in FIG. 40, the peak position shifted based on the cavity spacing.

Figure 41:
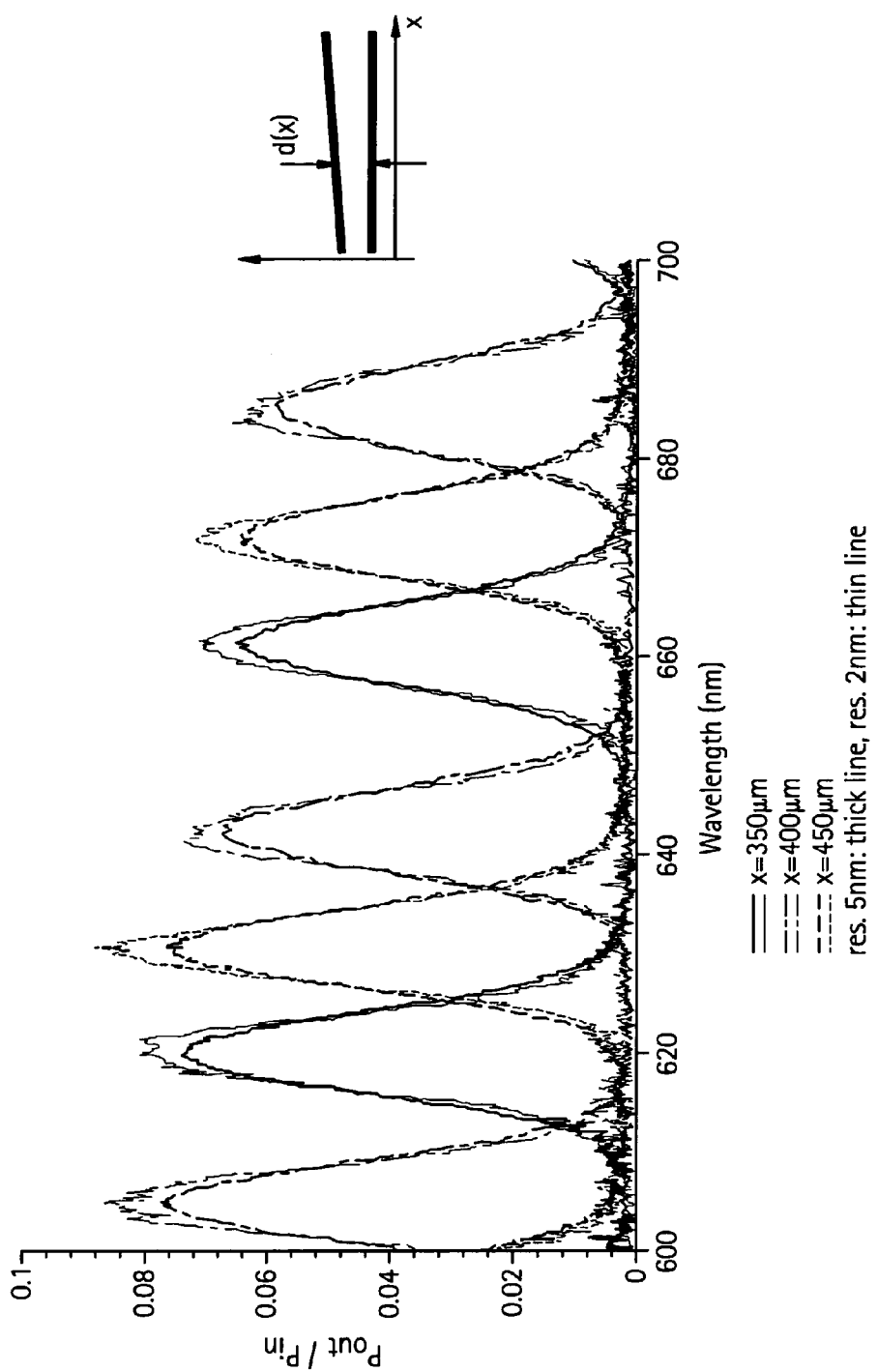

FIG. 41 shows a spectra from a Fabry-Perot cavity device with a variable (i.e., non-uniform) gap. The variable gap is achieved by tilting one of the silver mirrors against the other one, as shown in the schematic on the right hand side of FIG. 41. The dimensions of this device are as follows: quartz substrate/silver mirror (370 A)/tilt air gap/silver mirror (370 A)/quartz substrate. The tilt-angle is about 0.14 degrees. By probing with an optical fiber at different locations along the x-direction, the transmission spectra of the F-P cavity shown in FIG. 41 was measured as a function of local air gap defined at each probe location. FIG. 41 shows the wavelength tunability of the nanooptic filter. The peaks correspond to x=350 microns, 400 microns and 450 microns. The thin line corresponds to 2 nm resolution and the thick line to 5 nm resolution.

The systems, devices and methods using the filters 601 and 602 are described below. However, the systems, devices and methods may also include only one of the above described filters 601 and 602 used as the wavelength separation device. Furthermore, the filters 601 and/or 602 may also be used in combination with other filter types. Compact wavelength separation devices including monochromators and spectrum analyzers, as well as multispectral imaging systems and optical analyte detection systems may be based on plasmon resonance enhancement of radiation effect. The period of openings or surface features in a metal film or metal islands are varied in different portions or cells of the metal film or islands to form a two dimensional wavelength separation device portion 602 of the imaging and detection systems, which are renumbered with numbers such as 1, 11, 101, 201, 301 and 401 in different embodiments below. Furthermore, while the filter 601 is not shown in the figures described below, it should be understood that such filter 601 may be used together with the nanooptic array filter wavelength separation devices, such as devices 1, 11, 101 201, 301, and 401, for example.

The wavelength separation device includes a metal film or a plurality of metal islands, having a two dimensional array of a plurality of openings having a width that is less than a wavelength of incident radiation to be provided onto the film or islands. The metal film may comprise a single metal film or it may comprise one of a plurality of stacked layers of metal films. The metal islands may comprise a single layer of metal islands or they may comprise one of a plurality of stacked layers of metal islands. The metal film or islands are configured such that the incident radiation is resonant with at least one plasmon mode on the metal film or metal islands. The enhanced radiation transmitted through the openings has at least two passband ranges with two different peak wavelengths, and preferably three or more, such as ten or more, different passband ranges with different peak wavelengths.

Figure 1:
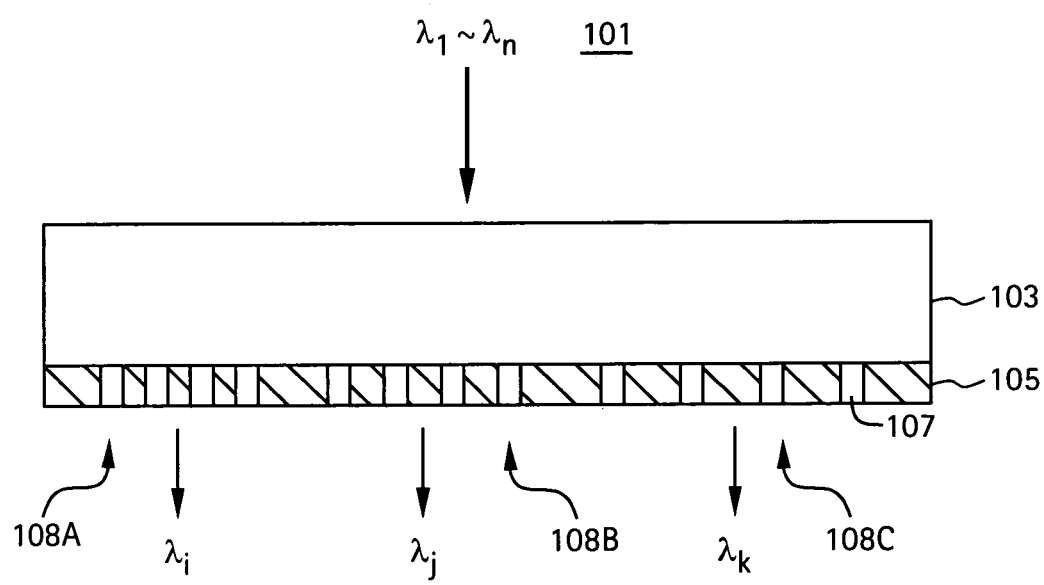
FIGS. 1, 2D and 3 are side cross sectional views of devices according to the preferred embodiments of the present invention.
Figure 2A:
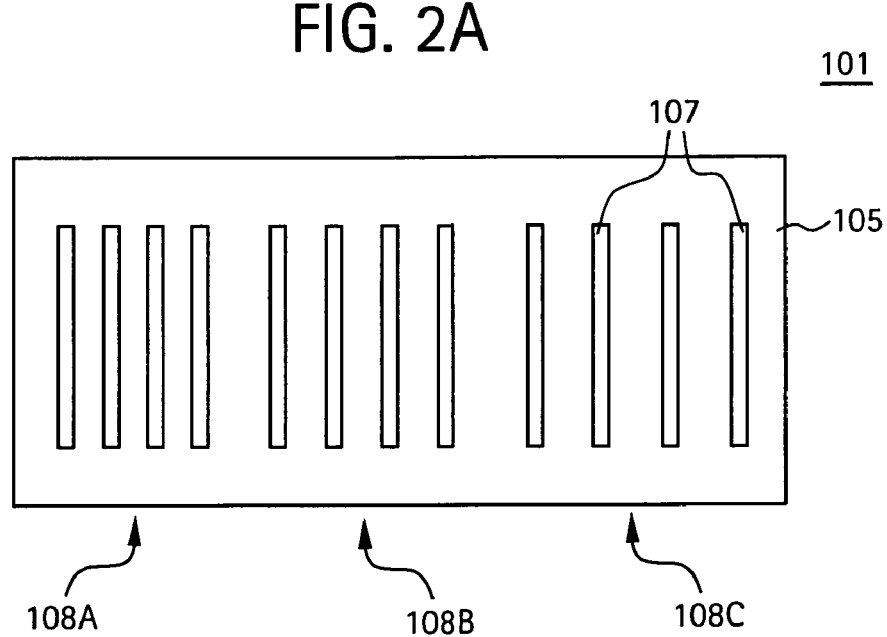

FIG. 1 is schematic illustration of wavelength separation using a stacked one dimensional (1D) slit array as a micronscale monochromator device 101. FIG. 2A illustrates the top of the device 101. As shown in FIG. 1, incident radiation having a range of wavelengths $\lambda_1$ to $\lambda_n$ is provided onto a metal film 105 having a plurality of openings 107. The openings have a width that is less than at least one wavelength of incident radiation, such that the incident radiation is resonant with at least one plasmon mode on the metal film. The transmitted radiation is provided through the plurality of openings such that the transmitted radiation is simultaneously separated into a plurality of passbands having different peak wavelengths $\lambda_i$, $\lambda_j$, and $\lambda_k$. The incident radiation may be provided onto either side of the film 105.

Preferably, radiation having a peak wavelength less than 700 nm, such as 400 nm to 700 nm (i.e., visible light) is used as the incident radiation. In this case, the openings 7 have a width of 700 nm or less, such as 15 to 200 nm, preferably 40 to 60 nm. In the case of incident radiation with longer wavelengths, such as infrared radiation, the openings may have a proportionally larger width.

Figure 2B:
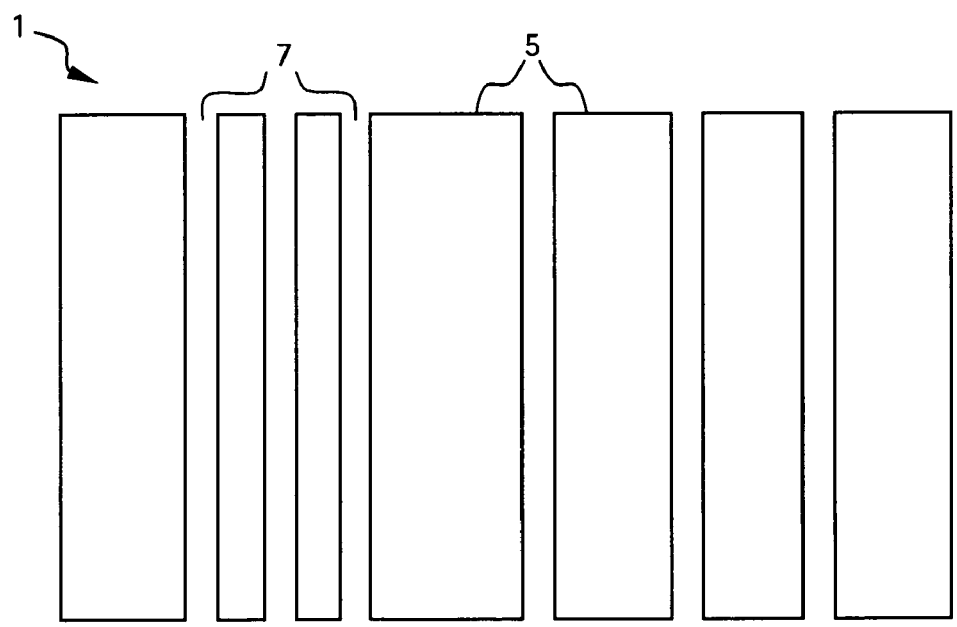

In this device 101, a metal layer or film 105 is formed over a radiation transparent substrate 103. However, a free standing metal membrane film without a supporting substrate or metal islands on a substrate may be used instead. For example, FIG. 2B illustrates a wavelength separation device 1 containing metal islands 5 separated by transparent regions 7.

Figure 2C:
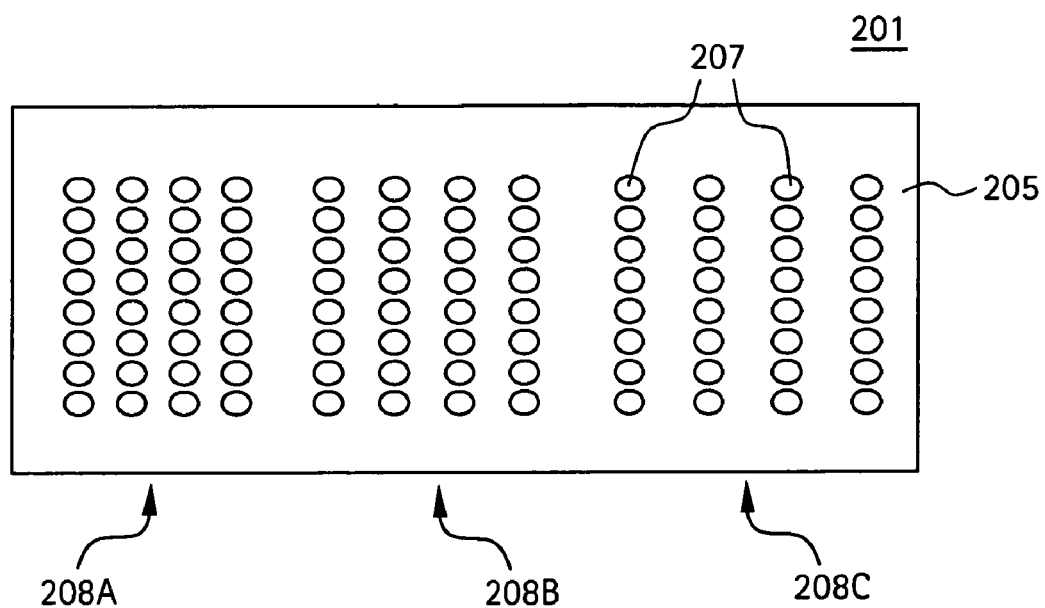

The metal film 105 contains slit shaped openings 107 that are periodically arranged with a cellular pattern. The slits preferably have a length that is at least ten times larger than the width. However, the openings 107 may have any other suitable shape, such as round, oval, polygonal or irregular shape. For example, FIG. 2C illustrates a device 201 containing a metal film 205 with groups of round openings 207 arranged in cells 208A, 208B and 208C.

The metal film 105 is divided into a desired number of cells or regions 108, such as at least two cells, where the grating period of the openings 107 is substantially the same within each cell. However, the grating period of the openings 107 differs between cells. In other words, the openings 107 in each cell are spaced apart from adjacent openings in the cell by about the same distance. However, this distance is different for different cells. For example, three cells 108A, 108B and 108C are illustrated in FIG. 1.

The grating period of the openings 107 in each cell 108 is designed to produce a passband at a certain peak wavelength in the transmission spectrum. Thus, a transmission of the radiation having one peak wavelength is enhanced due to the period of the openings in the first cell 108A. A transmission of the radiation having a different peak wavelength is enhanced due to the different period of the openings in the second cell 108B.

Preferably, the device 101 contains at least ten cells, more preferably at least 30 cells, such as 30 to 3,000 cells, for example 30 to 1,000 cells. A period of openings in each of the cells is different than periods of openings in each of the other cells. The transmission of passband radiation having a different peak wavelength through openings in each cell is enhanced due to the period of the openings in the respective cell. Preferably, the passband radiation transmitted through each cell 108 has a peak wavelength that differs by at least 1 nm, such as by at least 10 nm, for example by 10 to 100 nm, from peak wavelengths of radiation transmitted through the other cells 108.

The propagation length of surface plasmons is estimated to be about 5 to about 10 microns. A cell size comparable to this number or larger is preferred because it allows sufficient plasmon interaction. A 10-μm cell, for example, corresponds to about 30 periods of gratings when 0.5-μm peak passband wavelength is assumed. The cell size may be greater than 5 microns, such as greater than or equal to 10 microns, for example 10 to 10,000 microns, and the number of gratings per cell varies by cell size and peak passband wavelength.

A cell 108 size of about 10 microns, such as 5-20 microns is preferred because it matches a typical pixel size of commercially available CCD devices. For high array density (i.e., for better spatial resolution), it is desirable to keep the cell size as small as possible. However, for ease of fabrication, the cell size may be increased to about 50 to 500 μm. The overall size of a N-channel monochromator array 101 will then be approximately N×(50-500) μm. The N-channel monochromator array preferably has N cells 108, where N is an integer between 10 and 10,000.

Preferably, a period of openings in each cell ranges from about 250 nm to about 700 nm and a width of each opening preferably ranges from about 20 nm to about 80 nm for visible light incident radiation. The width of the openings 107 may be larger for infrared incident radiation.

An alternative design to the 1×N array pattern described above is to utilize a chirped grating (i.e., opening) pattern. In other words, the grating period (i.e., the period of the openings) is continuously chirped over a distance, L. If a radiation detector is used with the wavelength separation device, then the detector pixel size, W, defines the effective cell size of a wavelength separation device, such as a filter, and the total number of channels of the array will be L/W. An advantage of this design is that the entire monochromator array can be implemented with a single holographic lithography process, as will be described below.

Figure 2D:
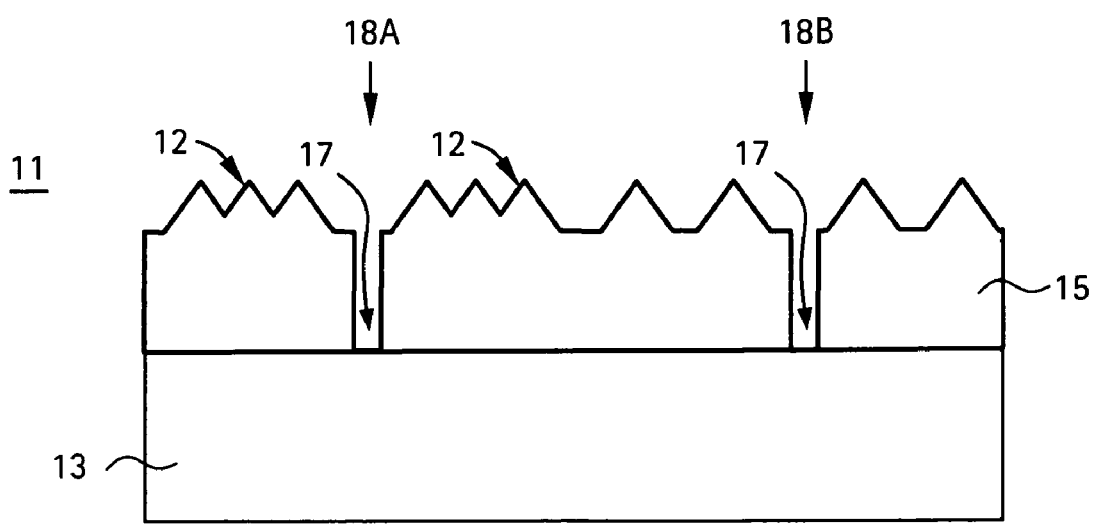

FIGS. 2D and 2E illustrate a wavelength separation device 11 according to a second preferred embodiment of the present invention. In the second embodiment, the metal film or metal islands 15 have a periodic or quasi-periodic surface topography 12 provided on at least one surface of the metal film or islands 15, as shown in FIG. 2D. If desired, the metal film or islands may be formed on a radiation transparent substrate 13. The topography 12 is configured such that it enhances the transmission of the radiation in the openings 17. The periodic topography 12 may comprise any metal features which provide strong coupling of the metal surface plasmons with incident radiation. For example, the topography may comprise any suitable raised and/or depressed regions on the surface of the metal film or islands 15 which are arranged in a regularly repeating (i.e., quasi-periodic or periodic) pattern, such as a two dimensional lattice. The raised regions may comprise cylindrical protrusions, semi-spherical protrusions, linear or curved ribs, rectangular ribs, raised rings and/or raised spirals. The depressed regions may comprise cylindrical depressions, semi-spherical depressions, linear or curved troughs, rectangular troughs, ring shaped troughs and/or spiral shaped troughs. The width or diameter of the raised or depressed regions is preferably less than the period of these features, and the product of this period with the refractive index of the substrate should be less than the maximum desired transmitted wavelength of the radiation.

The metal film or metal islands 15 comprise at least two cells 18, and preferably a plurality of cells, such as at least 10 cells, more preferably at least 30 cells. Each cell 18A, 18B, 18C, 18D comprises at least one of a plurality of openings 17. The periodic or quasi-periodic surface topography 12 configuration in each of the cells is different than periodic or quasi-periodic surface topography configurations in each of the other cells. Each cell is configured for transmission of passband radiation having a different peak wavelength, as in the first preferred embodiment.

While the linear grating patterns illustrated in FIGS. 2A-2C have polarization detection capability as an intrinsic function, the polarization dependence of filters may not be desirable for some applications. The monochromator patterns illustrated in FIG. 2E are insensitive to polarization in its transmission. For example, as shown in FIG. 2E, circular grating patterns 12 are used in forming corrugations of constant period for each concentric pattern. A subwavelength aperture 17 is made at the center of each pattern, and the incident light will be funneled into the aperture via resonant excitation of surface plasmons at a certain wavelength, which is determined by the grating period. Arranging the circular grating patterns of different periods into a two dimensional array, such as the 2×2 array shown in FIG. 2E results in a 4-channel spectrum analyzer that is insensitive to polarization.

In another preferred aspect of the second embodiment, the surface topography 12 comprises a topography comprising a material other than metal which includes surface plasmon coupling into the metal. In one example, the refractive index of the dielectric layer or ambient medium adjacent to the metal surface is periodically or quasi-periodically modulated, without topographic modulation of the metal surface (i.e., without corrugation/indentation on the metal surface). For example, periodic arrangement of dielectric layer or layers formed on a flat or corrugated metal surface can induce the surface plasmon coupling into metal. Thus, element 12 in FIG. 2D may refer to periodically or quasi-periodically arranged dielectric material features formed on a flat metal film or island 15 surface. Alternatively, a flat or textured dielectric layer or layers with a variable refractive index may be used for plasmon coupling. A variable refractive index in a flat dielectric layer or layers may be achieved by periodically or quasi-periodically modulating the composition of the layer or layers along their width on the metal film or islands. Any suitable dielectric material many be used, such as silica, quartz, alumnia, silicon nitride, etc.

In the second preferred embodiment, the openings or transparent regions 17 are separated by a period $a_o$ which is much larger than the period of the first embodiment, such that the period of the openings 17 does not substantially contribute to the enhancement of the transmission of the radiation. For example, the period $a_o$ is preferably equal to the effective propagation distance of the surface plasmons, such as 5 microns or greater, preferably about 5-10 microns for Ag islands being irradiated with visible light.

Figure 2H:
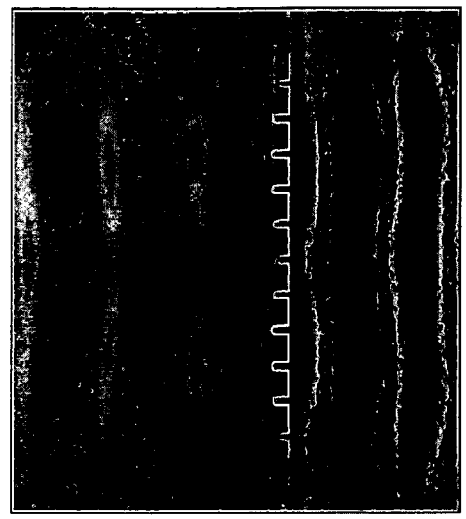
FIGS. 2F, 2G and 2H illustrate a finite-difference time-domain (FDTD) simulation of a difference in transmission of light having three different peak wavelengths.
Figure 2G:
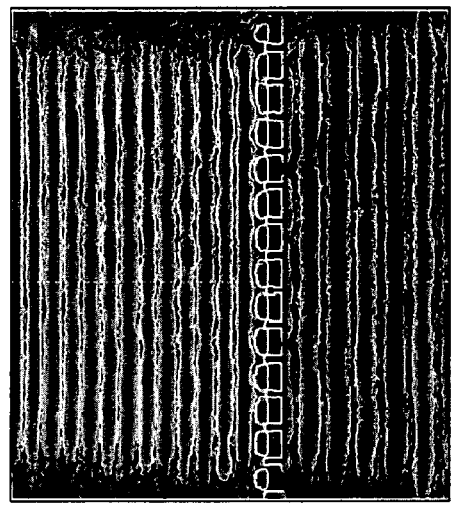
Figure 2F:
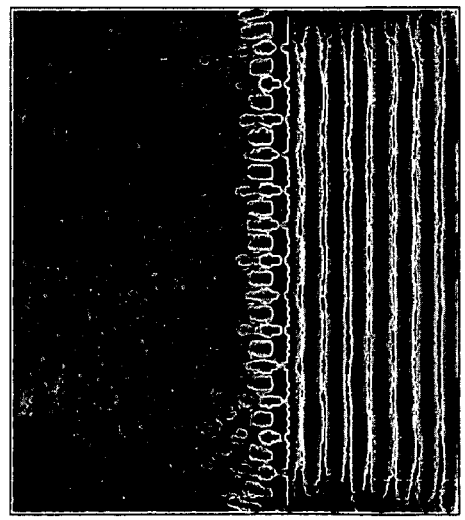

FIGS. 2F, 2G and 2H illustrate a finite-difference time-domain (FDTD) simulation of a difference in transmission of light having three different wavelengths through the same wavelength separation device comprising metal islands or a metal film containing a plurality of openings having a width that is smaller than the peak wavelength of the incident light. Specifically, the peak wavelength of the incident light is 540 nm, 680 nm and 1500 nm for the simulation illustrated in FIGS. 2F, 2G and 2H, respectively.

The wavelength separation devices, such as the monochromators or nano-optic filter arrays can be made ultra compact, and the wavelength separation can be achieved in an ultra-compact space. For example, the dimensions can be made as small as a micrometer-scale area along the a direction transverse to the radiation propagation direction (i.e., length) and virtually zero length (i.e., the thickness of stacked layers, such as less than 0.1 microns) along the longitudinal (i.e., radiation propagation) direction, without being restricted by the diffractive optics. Preferably, the monochromator length, width and thickness are each less than 1 cm. More preferably, the monochromator length is less than 100 microns and its thickness is less than 10 microns.

In the case of slit shaped openings in the metal film or between metal islands, (i.e., a 1D grating case), the optical transmission through the sub-wavelength openings depends on the polarization of incident light. For the TE polarized light (i.e., where the E-field is parallel to the grating lines), for example, surface plasmons are not excited due to the unavailability of grating vectors along the E-field direction, since the surface plasmons are longitudinal waves. Therefore, transmission for TE polarizations is expected to be much lower than TM polarization. This polarization dependence can be utilized for detecting the polarization (and its spatial distribution) of incident light. Alternatively, the wavelength separation device can be used as a polarizing filter.

Any suitable metal such as Ag, Al, Au and Cu may be used to form the metal film or metal islands. Preferably, metals, including Ag, Al, Au, Cu or their alloys, which exhibit a bulk plasmon frequency in the 9-10 eV range are used. This makes the plasmon-induced phenomena observable in a broad spectral range (Vis-to-IR). Al and Cu are common metals used as interconnect metallization in integrated circuit chips and photodetectors. Thus, the metal film or islands of the wavelength separation device may be made using the same semiconductor manufacturing equipment as used to form chips and photodetectors.

Figure 3:
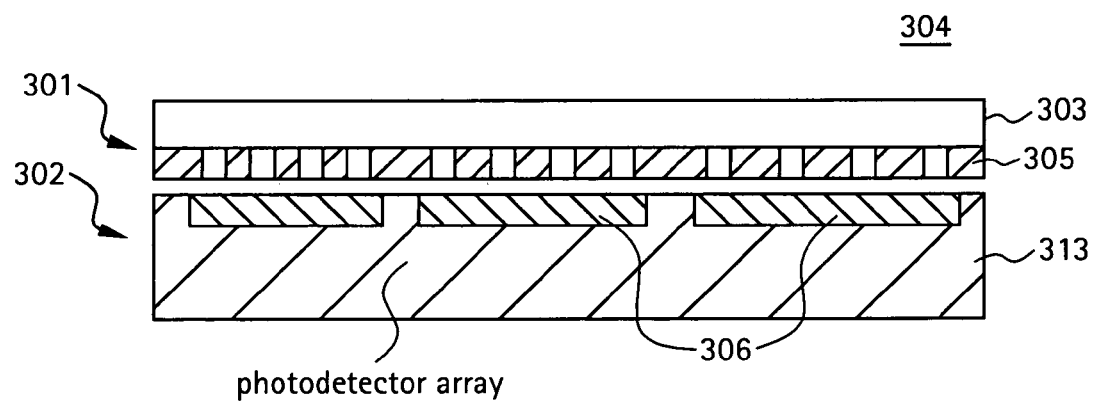

In a third preferred embodiment of the present invention, the wavelength separation devices 301 of the first two embodiments are used together with a photodetector 302 to form a spectrum analyzer device 304, as shown in FIG. 3. Any device which can detect visible, UV and/or IR passband transmitted radiation may be used as the photodetector 302. The photodetector 302 is adapted to detect radiation transmitted through the wavelength separation device 301.

Preferably, an array solid state photodetector cells, such as a semiconductor photodetector array is used as a photodetector. Most preferably, charge coupled devices (CCDs), a CMOS active pixel sensor array or a focal plane array are used as the photodetector. The photodetector 302 shown in FIG. 3 includes a substrate 313, such as a semiconductor or other suitable substrate, and a plurality of photosensing pixels or cells 306. Preferably, each photodetector cell or pixel 306 is configured to detect passband radiation having a given peak wavelength from each respective cell of the wavelength separation device 301. The wavelength separation device 301 includes the metal film or islands 305 and an optional radiation transparent substrate 303.

The photodetector 302 can be optically coupled (i.e., in contact or in proximity) to the output plane of the metal film or islands 305 for detection of the near-field output through the metal film or islands. The output of each detector cell is then electronically addressed for display and processing. A processor, such as a computer or a special purpose microprocessor, is preferably provided to determine an intensity of radiation detected by each cell of the photodetector. Thus, the photodetector 302 is preferably optically coupled to the metal film or the metal islands 305 without utilizing diffractive optics between the wavelength separation device and the photodetector.

In a preferred aspect of the invention, the spectrum analyzer 304 thickness in a radiation transmission direction is less than 1 cm and the spectrum analyzer 304 length perpendicular to the radiation transmission direction is less than 1 cm.

In a fourth preferred embodiment of the present invention, the nanophotonic monochromator/spectrum analyzer can be used as a multispectral imaging system, when the monochromator is extended to a two dimensional array configurations. A multispectral imaging system is a system which can form an image made up of multiple colors. One example of a multispectral imaging system is a digital color camera which can capture moving and/or still color digital images of objects or surroundings. Another example of a multispectral imaging system is an infrared camera, which forms a digital image in visible colors of objects emitting infrared radiation, such as a night vision camera. The camera contains a processor, such as a computer, a special purpose microprocessor or a logic circuit which forms a color image (i.e., as data which can be converted to visually observable image or as an actual visually observable image) based on radiation detected by the photodetector. The multispectral imaging system may store the color image in digital form (i.e., as data on a computer readable medium, such as a computer memory or CD/DVD ROM), in digital display form (i.e., as a still or moving picture on a screen) and/or as a printout on a visually observable tangible medium, such as a color photograph on paper.

Figure 4A:
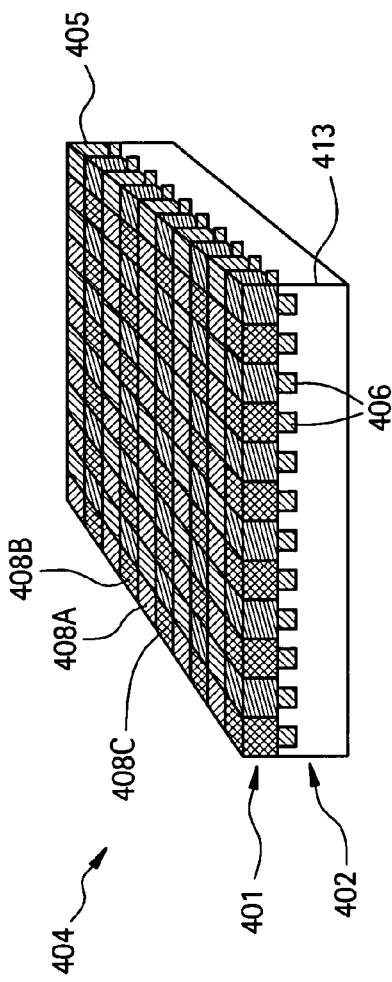
FIG. 4A is a perspective view and FIGS. 4B and 4C are top views of a multispectral imaging system of the preferred embodiments of the present invention.
Figure 4C:
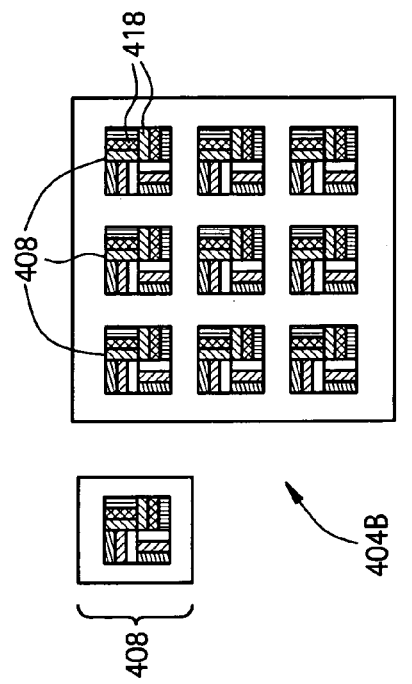
Figure 4B:
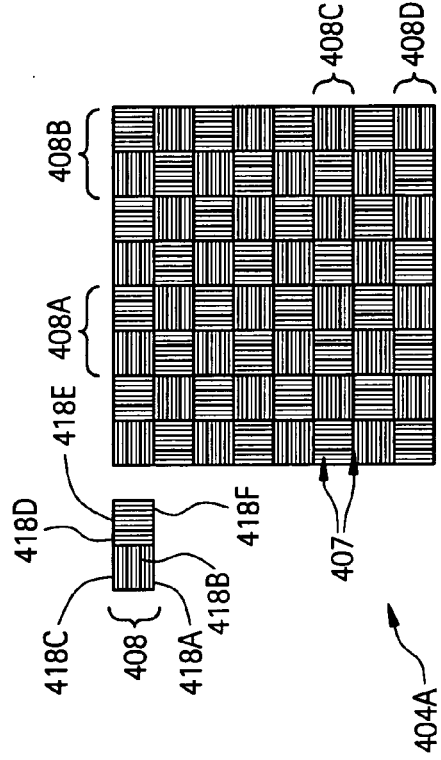

FIGS. 4A, 4B and 4C show examples of a multispectral imaging system 404 comprising a three dimensional wavelength separation device 401 and a photodetector 402. The wavelength separation device 401 comprises a 2D mosaic arrangement of metal islands or subwavelength slits in a metal film 405 that allows multi imaging with spatially resolved polarization detection capability. The system 404 contains an array of cells 408 arranged in two dimensions in the wavelength separation device 401. Preferably, the cells 408 are arranged in a rectangular or square matrix layout. However, any other layout may be used instead. Each cell 408 is adapted to produce a multicolor portion of a multidimensional image.

Each cell 408 comprises at least three subcells 418. Each subcell 418 in a particular cell 408 is designed to transmit one particular color (or a narrow IR, VIS or UV radiation band). Preferably, each subcell 418 comprises metal islands or a metal film 405 with slit shaped openings 407 having a given first period. This first period of the openings is different from the periods of at least some of the other subcells 418 in a given cell 408. In this case, each subcell 418 in a particular cell 408 is designed to transmit one particular color (or a narrow IR or UV radiation band) with a certain polarization. In other words, each subcell 418 allows radiation having a given narrow band of wavelength to pass through. For example, the narrow band of wavelengths may correspond to a particular color of visible light radiation. Each cell 418 of the 2D array 404 is preferably identical to the other cells in the array because each cell contains the same arrangement of subcells 418.

For example, FIG. 4B illustrates a system 404A containing thirty two cells 408 (8×4 array of cells 408A, 408B, 408C, etc.) in the wavelength separation device. Each cell 408 contains six subcells 418. Each subcell is designed to transmit one particular color with a certain polarization to detector 402. Three subcells 418A, 418B, 418C have slit shaped openings 407 oriented in a first direction (such as a horizontal direction). Another three subcells 418D, 418E and 418F have slit shaped openings oriented in a second direction perpendicular to the first direction (such as a vertical direction). Thus, each cell 408 with this subcell layout can transmit both TM and TE polarized light. In one preferred aspect of this embodiment, the period of the openings 407 in each pair of subcells (418A and 418D, 418B and 418E, 418C and 418F) is the same. The subcells in each pair of subcells have slit shaped openings oriented perpendicular to each other to detect TE and TM polarizations of each color. However, the period of openings 407 is different between each pair of subcells. Thus, the system 404A shown in FIG. 4B is a three color imaging system, where each pair of subcells is adapted to transmit one color.

FIG. 4C illustrates a system 404B containing nine cells 408 (3×3 array of cells) in the wavelength separation device. Each cell 408 contains twelve subcells 418. In one preferred aspect of this embodiment, the period of the opening in each pair of subcells is the same. The subcells in each pair of subcells have slit shaped openings oriented perpendicular to each other to detect TE and TM polarizations of each color. However, the period of openings is different between each pair of subcells. Thus, the system 404B shown in FIG. 4C is a six color imaging system, where each pair of subcells is adapted to image one color.

The subcells 418 are arranged in each cell 408 in a square or rectangular matrix. However, any other suitable arrangement may be used. The three- or six-color-separation systems were described above for illustration purposes only. By increasing the number of subcells in each cell, the system can be easily scaled up for high-resolution multichannel analyzers with more than six color separation and imaging. Furthermore, the cells 408 may be located in contact with adjacent cells, as shown in FIG. 4B or separately from adjacent cells, as shown in FIG. 4C. While the mosaic arrangement of subcells 418 within a single cell 408 allows for multicolor separation capability, repeating the mosaic cell into a 2D array results in an array of spectrum analyzers on a single chip to form the multispectral imaging system, such as a color camera.

The systems described above contain metal islands or metal film with subwavelength slit shaped openings. However, metal islands or a metal film with a periodic or quasi-periodic surface topography may be used instead. For example, the multispectral imaging system may comprise a two dimensional array of subcells shown in FIG. 2E instead of metal islands or a metal film with slit shaped openings shown in FIGS. 4A-4C. Thus, FIG. 2E shows one cell of a multicell array, where the cell contains four subcells 18A, 18B, 18C and 18D. Each subcell has features 12 with a different period and a subwavelength opening 17. Thus, this is a four color imaging system. Since these subcells are not polarization dependent, there is no need to form pairs of subcells with the same opening period but perpendicular opening directions to image each color, as in the systems illustrated FIGS. 4A-C.

Furthermore, the multispectral imaging systems also contain a photodetector 402, as described above. Preferably, the photodetector 402 contains one pixel or cell 406 for each cell 408 in the metal film or metal islands. Most preferably, each photodetectror pixel 406 is arranged on a substrate 413 in registry with each cell 408, such that each photodetector pixel 406 receives radiation transmitted through only one cell 408.

In a fifth preferred embodiment of the present invention, the nanophotonic spectrum analyzer or the multispectral imaging system described above are used in an optical analyte detection system. An analyte detection system is a system in which radiation from the analyte is detected by the spectrum analyzer or the multispectral imaging system. The analyte may be an organic material, such as a biomaterial (i.e., protein, antibody, antigen, etc.) or a polymeric material, or an inorganic material, such as a metal, glass, ceramic or semiconductor material. The analyte may be in any one or more of solid, liquid or gas states. Any suitable radiation from the analyte may be detected by the analyte detection system, such as fluorescence or luminescence from the analyte, absorption or transmittance of incident radiation which passes through the analyte or is reflected from the analyte, or modification of the incident radiation by the analyte, such as peak shifting in the radiation that is transmitted through or reflected by the analyte.

Figure 5A:
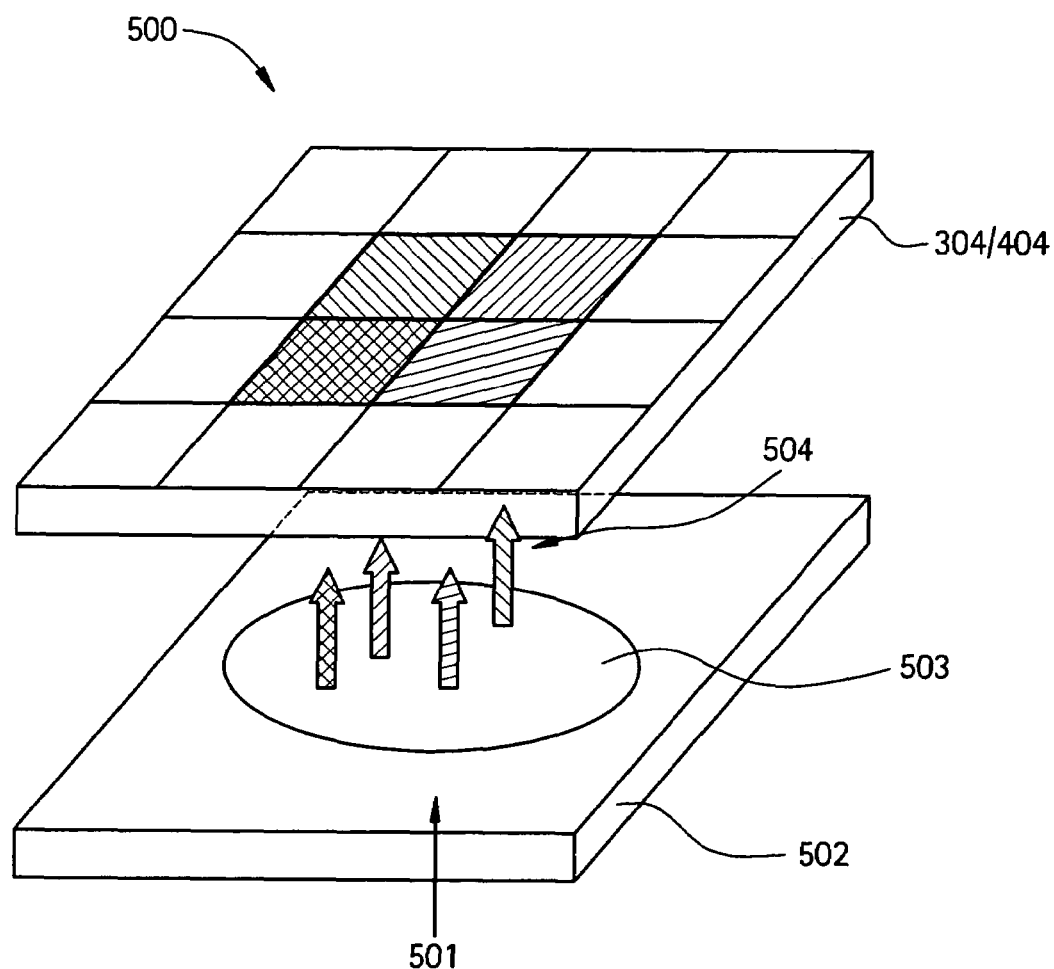
FIGS. 5A and 5B are perspective views of an optical analyte detection system of the preferred embodiments of the present invention.

FIG. 5A illustrates an exemplary optical analyte detection system 500. The system 500 includes an excitation source 501, an analyte holder 502 and either the one dimensional spectrum analyzer 304 or the two dimensional multispectral imaging system 404 described above.

Any suitable excitation source 501 may be used. Preferably, an optical excitation source 501, such as a light emitting diode, laser or lamp emitting in the UV, visible or IR range is used. However, any other non-optical excitation source may be used instead, which generates an optical response 504, such as fluorescence, from the analyte 503. For example, the excitation source may comprise a thermal source, such as a heater or furnace, which causes the analyte to emit radiation in response to heat. Alternatively, an X-ray, gamma ray or electron beam source may be used as an excitation source if the X-rays, gamma rays or electrons cause the analyte to emit radiation.

The analyte holder 502 may comprise any device that can hold the analyte 503 during the optical detection. For example, as shown in FIG. 4A, the analyte holder 502 may comprise a microslide if the analyte 503 is a liquid, solid or gel biomaterial, such as a serum sample. Alternatively, the analyte holder 502 may comprise a radiation transparent gas or liquid container for a gas or liquid analyte, or any suitable shelf, susceptor or support for a solid or gel analyte 503.

The system 500 includes a one dimensional spectrum analyzer 304 (i.e., the monochromator and photodetector combination described above) to detect the radiation 504 from the analyte 503 if two dimensional resolution of the analyte is not required. The system 500 includes the two dimensional multispectral imaging system 404 described above if it is desirable to detect radiation from a two dimensional distribution of analyte 503. For example, the multispectral imaging system may detect differences in radiation 504 emitted by different regions of the analyte 503 and/or may be used to detect radiation 504 from a larger portion of the analyte 503.

Figure 5B:
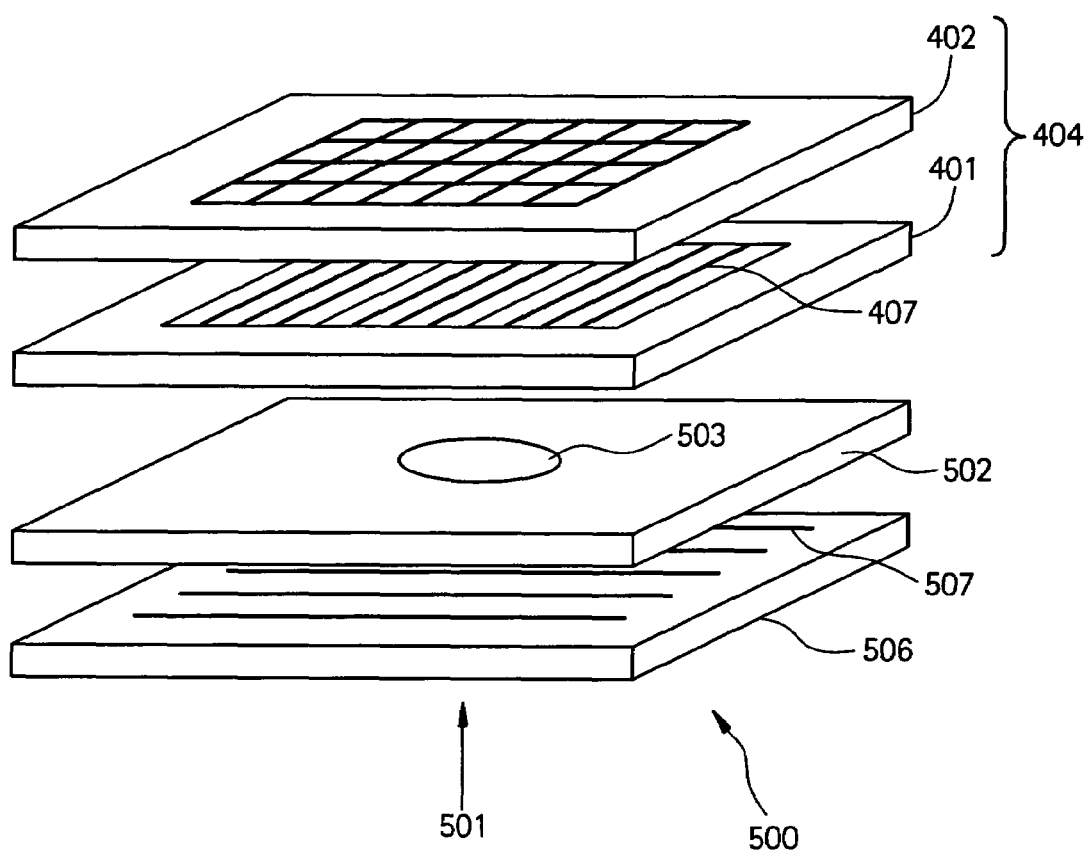

FIG. 5B illustrates a preferred embodiment of the optical analyte detection system 500. In this system 500, the excitation source 501 comprises a light emitting diode or a laser diode. An optional nano-optic excitation filter 506 is placed between the excitation source 501 and the analyte holder 502. The filter 506 may comprise a metal film or metal islands containing subwavelength slit shaped openings 507 having the same period, in order to polarize the incident radiation. Alternatively, the filter may comprise another type of polarizing filter that polarizes the incident radiation. The analyte holder 502 comprises a microslide and the analyte 503 comprises a biomaterial, such as a protein, antibody and/or fluorophore containing sample. The multispectral imaging system 404 includes the photodetector 402 and the wavelength separation device 401 described above. Preferably, the openings 407 in the wavelength separation device 401 are slit shaped and are oriented in a direction perpendicular to the openings in the filter 506. Thus, the openings 407 prevent the polarized excitation source 501 radiation from reaching the photodetector 402, and the photodetector detects fluorescence from the analyte 503 which passes through the openings 407. In other words, the grating lines of the two dimensional nano-optic monochromator 401 are aligned perpendicular to those of the excitation filter 506 so that the unabsorbed incident (i.e., excitation radiation) is significantly filtered out before reaching the detector array 402.

The nano-optic filters show an acceptance angle of about ±5-10 degrees. A spacing between about 200 to about 2000 microns between the nano-optic monochromator array 401 and the analyte holder 402 is expected to be reasonable for an about 10 to about 100 micron cell size of the wavelength separation device (i.e., nano-optic array) 401. This spacing provides sufficient space to slide a plate shaped analyte holder 502 with the analyte 503 in and out of the system 500.

As discussed above, the nano-optic monochromator array 401 can be integrated with a detector chip 402 in a hybrid or monolithic fashion as discussed above. In the hybrid configuration case, commercially available detector chips (CCDs or CMOS active pixel sensor arrays) may be used. The number of cells 408 (i.e., channels) in the nano-optic monochromator 401 may be kept relatively small, such as 10 to 100 cells. However, a larger number of cells, such as 100 to 10,000 cells may be used. The size of each cell may be about 50 to about 500 microns, which is 5 to 50 times larger than the pixel size of commercial photodetector arrays (typically about 10 microns in CCDs). A particular wavelength component of a fluorescence signal that passes through a cell 408 is then detected by about 5 to about 50 pixels. Alternatively, each cell 408 may be designed to correspond to one photodetector pixel. In the case of monolithic integration of the monochromator 401 and photodetector 402, the nano-optic monochromator may be located in a portion of the metal interconnect of a CMOS active pixel array (or of a CCD) chip. Therefore the entire process is compatible with the standard CMOS process.

Figure 6:
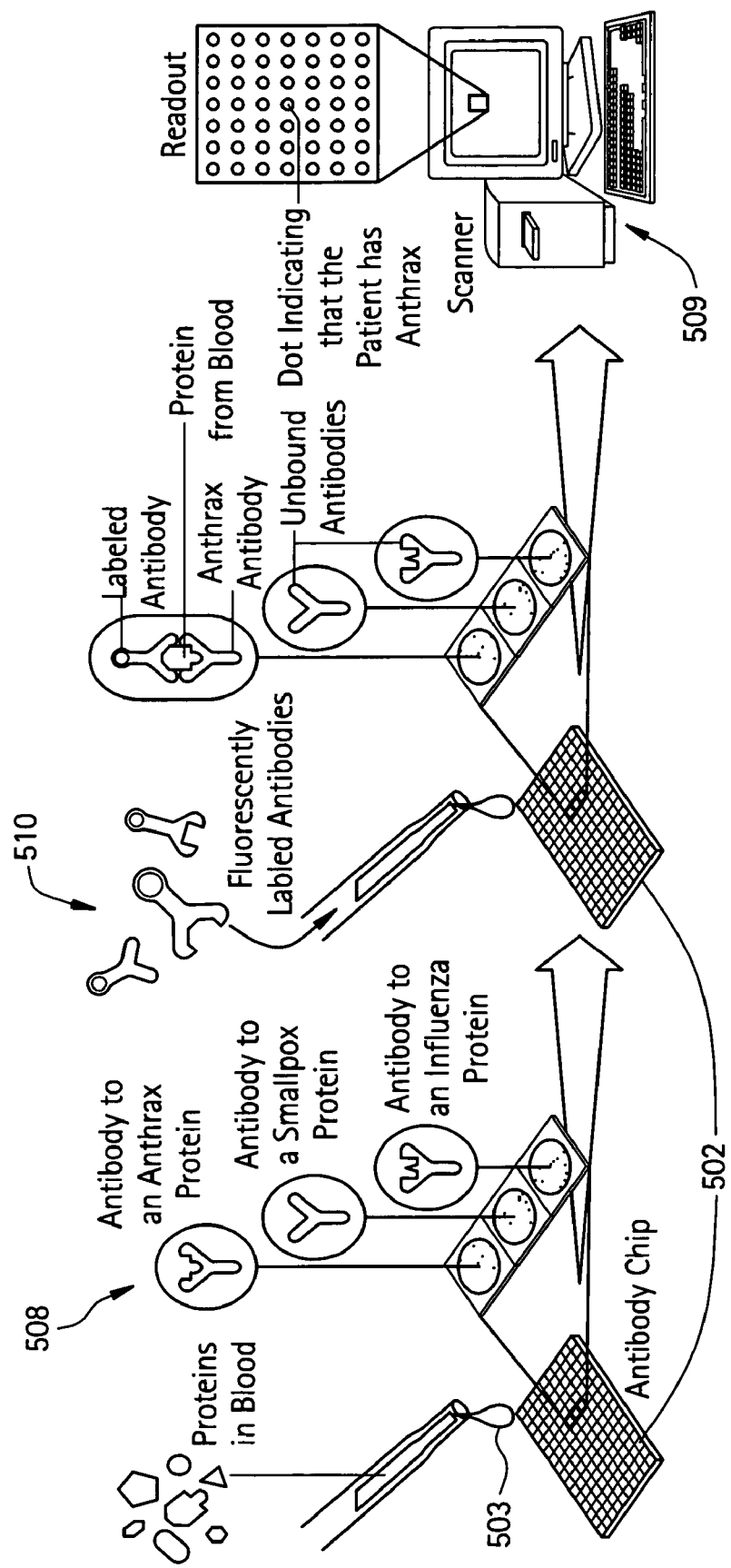
FIG. 6 is a schematic illustration of a method of using the optical analyte detection system of the preferred embodiments of the present invention.

FIG. 6 illustrates a method of using the optical analyte detection system 500 for medical analysis according to a preferred embodiment of the present invention. However, the system 500 may be used on other analytes and/or for other purposes.

As shown in FIG. 6, a bio analyte 503, such as blood or other human or animal body fluid, is provided onto the analyte holder 502. The analyte 503 contains various components of interest, such as proteins, antibodies, etc. The analyte holder 502 contains an array of one or more types of attachment members 508, such as various antibodies, antigen, proteins etc. For example, the attachment members 508 may comprise specific antibodies to various disease proteins, such as influenza, smallpox and anthrax proteins. Alternatively, the attachment members 508 may comprise specific antigen or protein to various disease antibodies.

In one preferred aspect of this embodiment, these antibodies are fluorescently labeled with any suitable fluorophore, such as an organic dye molecule or a semiconductor quantum dot. When the analyte 503 contains antigen or proteins that specifically bind to the antibodies 508, these antigen or proteins bind to the antibodies 508. The binding changes the characteristic of the radiation 504 emitted by the fluorophore in response to the excitation radiation. For example, the wavelength and/or intensity of the radiation 504 emitted by the fluorophore may be changed by the binding. The photodetector 402 detects the radiation 504 and a computer or other processor 509 stores, transmits and/or displays the results of the detection by the photodetector. For example, when the radiation 504 from the fluorophore attached to the anthrax specific antibody 508 changes, the computer 509 indicates that the analyte blood 503 came from a patient who is infected with anthrax.

The binding may be detected by one or more of the following methods. In the first method, different attachment members are provided onto different regions of the analyte holder 502, and this layout information is provided into the computer 509. The analyte holder 502 containing attachment members 508 is irradiated with exciting or incident radiation 501 and the fluorescence radiation 504 of the fluorophores is detected by the photodetector 402 as the background radiation. Then, the analyte 503 is provided onto the analyte holder 502 and the analyte holder is again irradiated with the exciting radiation 501. The photodetector detects the fluorescence radiation 504 and the computer 509 determines if the fluorescence radiation 504 changed from any region on the analyte holder from before to after the placement of the analyte 503. The computer can thus determine if there was binding to the specific attachment members 508 in a particular region of the analyte holder 502, and thus determine the content of the analyte 503 since the attachment members 508 are different in different regions of the analyte holder 502. If desired, the exciting radiation 501 may be directed onto the analyte holder 502 continuously to detect real time binding between the proteins or antigen in the analyte 503 and the attachment members 508.

In another method to detect the binding, a fluorophore having a different fluorescence wavelength is attached to each type of attachment member 508 and this data is stored in the computer 509. The sample holder 502 containing attachment members 508 is irradiated with exciting or incident radiation 501 and the fluorescence radiation 504 of the fluorophores is detected by the photodetector 402 as the background radiation. Then, the analyte 503 is provided onto the analyte holder 502 and the analyte holder is again irradiated with the exciting radiation 501. The photodetector detects the fluorescence radiation 504 and the computer 509 determines if the fluorescence radiation 504 of a particular wavelength changed from before to after the placement of the analyte 503. The computer can thus determine if there was binding to the specific attachment members 508 based on the wavelength of the fluorophore radiation that was changed after the introduction of the analyte 503. If desired, the exciting radiation 501 may be directed onto the analyte holder 502 continuously to detect real time binding between the proteins or antigen in the analyte 503 and the attachment members 508. In this method, it is preferred, but not necessary to locate different types of fluorophores/attachment members 508 on different regions of the analyte holder 502, since the wavelength rather than location of the changed radiation is used to detect binding. It should be noted that the intensity of the detected radiation may be used to determine the degree of binding between the analyte contents and the attachment members 508, if desired.

A third detection method is illustrated in FIG. 6. In this method, the fluorophores are not attached to the attachment members 508. Instead, additional fluorescently labeled members 510, such as fluorescently labeled antibodies, antigen or proteins, are provided onto the analyte holder 502 after the analyte 503. These members 510 are designed to bind to proteins, antigen or antibodies found in the analyte 503. Thus, if the antibodies, antigen or proteins form the analyte 503 are bound to the attachment members 508, then the fluorescently labeled members 510 also bind to these antibodies, antigen or proteins form the analyte 503. The presence of the bound antibodies, antigen or proteins form the analyte 503 is determined by irradiating the analyte holder 502 with exciting or incident radiation 501 and the fluorescence radiation 504 from the members 510 is detected by the photodetector 402. The different types of fluorescently labeled members 510 may be labeled with fluorophores which emit radiation of a different wavelength and/or different types of attachment members 508 may be located in different parts of the analyte holder 502 in order to distinguish a type of protein, antibody or antigen that bound to the attachment members 508.

In this method, while it is preferable to include the attachment members 508, these members 508 may be omitted. Instead, the surface of the analyte holder 502 may be treated to attach all proteins, antibodies, antigens or other analyte components of interest, and the different types of fluorescently labeled members 510 labeled with fluorophores which emit radiation of a different wavelength are provided onto the analyte 503. Members 510 are designed to only bind to specific components of the analyte. If these analyte components are not present, then members 510 will not remain on the analyte holder 502. Thus, presence of a particular component of the analyte may be detected without attachment members 508 by determining the wavelength(s) of radiation emitted by the attached labeled members 510.

The overall system 500 performance is expected to be determined by the following factors: the power and spectral characteristics of both the excitation source and fluorophores, the detector 402 responsivity, spacing between component layers and the filter characteristics of both the excitation filter 506 and monochromator array 401. In the case of multispectral fluorescence using organic dye fluorophores, each dye usually requires different excitation wavelength. LEDs can be used with nano-optic excitation filters shown in FIGS. 1-2E in order to produce a wavelength-multiplexed beam that has a well-defined narrow spectral width at each component wavelength. In the case of quantum dot fluorophores, the fluorophores of different wavelengths can be excited with a single exciting wavelength. This simplifies excitation optics compared with using organic dye fluorophores.

An advantage of the system 500 is its capability to simultaneously detect multiwavelength components of fluorescence signals utilizing the fine resolution of the nano-optic monochromator 401 in conjunction with quantum dot or nanotube probes of narrow spectral width. This multispectral detection allows an application of a deconvolution technique in extracting each wavelength component from mixed-wavelength signals. This is further refines the spectral analysis capabilities of the system 500.

Another advantage of the system 500 is high throughout. For example, as shown in FIGS. 4B and 4C, by using two dimensional monochromators 401 having a 4×8 or 3×3 array configuration, respectively, allows simultaneous analysis of 8×4 or 3×3 analyte arrays. The 2D arrays, whose individual cells possessing multispectral analysis capability, offer an ultimate high-throughput.

The one and two dimensional spectrum analyzers 304, 404 may be made by any suitable method. For example, the wavelength separation device 301, 401 and the photodetector 302, 402 may be manufactured separately and then bonded or attached together to form the analyzer. For example, the wavelength separation device 301, 401 and the photodetector 302, 402 may be attached to each other by a radiation transparent layer or adhesive and/or by a fastening device, such as a bracket. The wavelength separation device 301, 401 and the photodetector 302, 402 may be attached to each other at the periphery or along their entire length. The wavelength separation device 301, 401 may contact the photodetector 302, 402 directly, or a radiation transparent layer, such as a silicon oxide or glass layer, or the substrate 303 may be placed between them.

In another preferred aspect of the third embodiment, the spectrum analyzer device is formed monolithically. In other words, rather than forming the wavelength separation device 301, 401 and the photodetector 302, 402 separately and then attaching them to each other, the individual components or layers of one of the wavelength separation device 301, 401 and the photodetector 302, 402 are formed sequentially over the other. Thus, the individual components or layers the wavelength separation device 301, 401 may be formed sequentially over the photodetector 302, 402 and vise versa.

For example, the solid state photodetector array 302, 402 is provided in or over a substrate 313. This step preferably includes photolithographically forming a CCD, a CMOS active pixel array or a focal plane array in or on the substrate 313. In other words, the photodetector array 302, 402 may be formed by standard microfabrication techniques, such as semiconductor, metal and/or insulating layer deposition, ion implantation, photoresist masking, and etching of the unmasked layer portions.

A metal film 305, 405 is then monolithically deposited on the photodetector array 302, 402 (i.e., the metal film is deposited by a thin film deposition method, such as evaporation, sputtering or CVD rather than being formed and then attached to the array 302, 402). The metal film 305, 405 is then photolithographically patterned to form a plurality of openings therein. The openings may be formed by forming a photoresist layer on the metal film or over a hardmask layer over the metal film, exposing and patterning the photoresist layer, and then etching the uncovered portions of the metal film to form the openings.

Alternatively, a plurality of metal islands are monolithically deposited onto the photodetector array 302, 402. A number of suitable island deposition methods may be used, as will be described in detail below.

If the metal film or metal islands contain a periodic or quasi-periodic surface topography, then the topography may be photolithographically formed on the metal film or islands.

In a preferred aspect of the invention, the wavelength separation device is formed at the same time as the metallization of the photodetector. For example, the metal film or metal islands 305, 405 may be formed over a interlayer insulating layer which is formed over metallization or interconnects of the photodetector 302, 402. In CCD, CMOS or focal plane array photodetectors, one or more levels of metallization interconnects are formed over the semiconductor devices. The wavelength separation device 301, 401 may be formed over the metallization layers, between the metallization layers, as part of one of the metallization layers (i.e., a portion of a metal level acts as the wavelength separation device and another portion acts an interconnect for the photodetector), below the metallization layers, or on the opposite side of the substrate 313 from the metallization layers.

For example, the wavelength separation device may comprise an Al film or islands and may comprise a portion of the Al interconnect parts of a standard CMOS process. In the 0.13-μm CMOS process, for example, five or six levels of metal interconnects are used. These interconnects can be designed as the nano-optic monochromator arrays and be monolithically integrated with CMOS active pixel arrays on the same chip. The nano-optic filter arrays can be designed to cover the spectral range of approximately 400 to 1000 nm, by using grating periods of 250 to 700 nm. Thus, the spectrum analyzer chips 304, 404 can be fabricated using a semiconductor foundry service.

In the devices of the preferred embodiments, a symmetric configuration may be used to reduce a passband width (i.e., to reduce the number of sidelobes or sidebands) if desired. In this configuration, the wavelength separation device is sandwiched between two radiation transparent substrates composed of the same dielectric media.

If metal islands are used as the wavelength separation device, then these islands may be made by any suitable method. For example, in one preferred aspect of the present invention, the metal islands spaced apart by radiation transparent regions or slit shaped openings are formed by self assembly. In other words, rather than forming a metal film and patterning the film into metal islands, the spaced apart metal islands are formed simultaneously or sequentially without first being part of an unpatterned metal film. The metal islands may comprise discrete metal islands that are not connected to each other (i.e., the metal islands are not in direct contact with each other) or metal islands that are connected to each other at a peripheral region of the optical device. In another preferred aspect, the metal islands comprise discrete islands that are formed by patterning a metal film into the islands. Preferably, the islands are patterned using a lithographic method.

The metal islands 5 may have any suitable thickness such that the islands 5 themselves are opaque to radiation but will generate plasmon enhanced radiation transmission through openings or regions 7. Preferably, metal island thickness should be at least about two or three times the skin depth of metal. In silver islands with incident radiation in a visible wavelength range, the skin depth is around 30 nm, and the metal island thickness should be at least about 60 to 90 nm or greater. The skin depth increases for longer wavelength range and is somewhat different for different metals. Thus, for example, the metal islands 5 may have a thickness of about 50 nm to about 2000 nm, such as 100 nm to 400 nm, preferably 120 to 180 nm.

Figure 7:
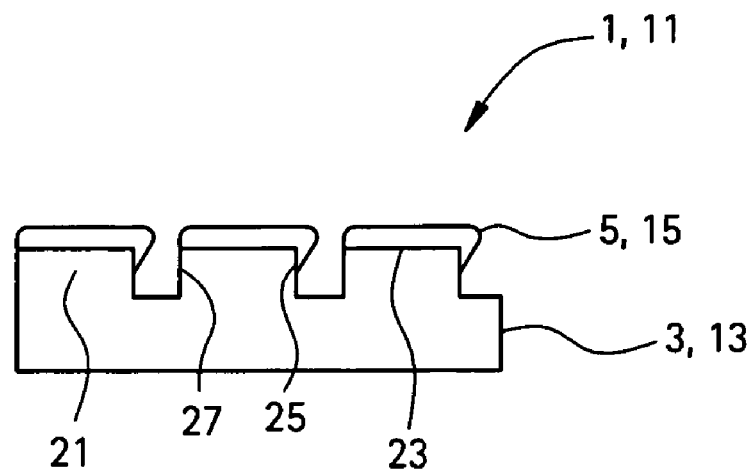
FIG. 7 is a schematic side cross sectional view of a device according to the preferred embodiments of the present invention.

In a preferred aspect of the first and second embodiments, the metal islands 5, 15 are formed by self assembly and are located on a plurality of ridges 21 on the transparent substrate 3, 13. Preferably, as shown in FIG. 7, each one of the plurality of metal islands 5, 15 is located on a corresponding one of the plurality of ridges 21. The metal islands and the ridges may have any suitable shape, as discussed above. Preferably, the metal islands and the ridges are shaped such that the openings 7, 17 between the islands are slit shaped. Thus, a length of each metal island is preferably at least 10 times larger than its width and a length of each ridge is preferably at least 10 times larger than its width. As shown in FIG. 7, the plurality of ridges 21 preferably have a rectangular shape. The ridges 21 may comprise protrusions on the upper portion of the radiation transparent substrate 3, 13, protrusions on the upper portion of a radiation transparent layer located on the radiation transparent substrate or the photodetector 302, 402, or discrete radiation transparent elements located over the radiation transparent substrate or the photodetector 302, 402. Thus, the substrate 3, 13 may comprise a unitary substrate (i.e., a single layer radiation transparent material) or it may contain more than one layer of radiation transparent material. The ridges 21 may have a variable period to form devices of the first preferred embodiment.

Figure 8:
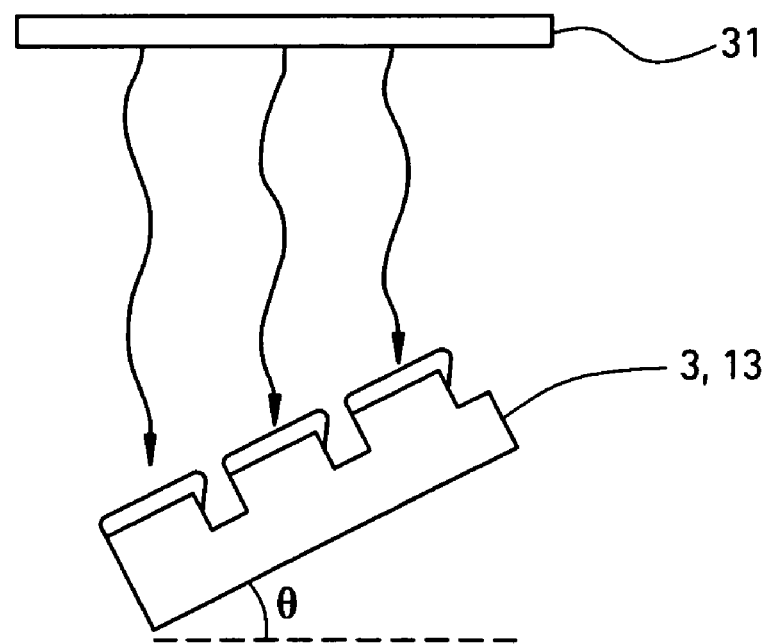
FIG. 8 is a schematic side cross sectional view of an apparatus used to make the device of FIG. 7.

Preferably, each respective metal island 5, 15 extends over an upper surface 23 of each ridge 21 and over at least a portion of at least one side surface 25 of each respective ridge 21. Most preferably, the metal islands are formed by angled deposition, as shown in FIG. 8. In this case, each metal island 5, 15 extends lower over a first side surface 25 of a respective ridge 21 than over a second side surface 27 of the respective ridge 21 because the metal is angle deposited from the first side surface 25, as will be described in more detail below.

In an alternative aspect of the present invention, the substrate 3, 13 comprises a nanopore array. Preferably, the substrate 3, 13 comprises an anodic aluminum oxide nanopore array located over a radiation transparent substrate or the photodetector, as will be described in more detail below.

The optical devices 1, 11 of the preferred aspects of the present invention may be made by any suitable method where a plurality of metal islands 5, 15 are formed on the radiation transparent substrate 3, 13. As described above, the metal islands 5, 15 are preferably selectively deposited on the plurality of ridges 21, such that metal is not deposited between the ridges 21.

FIG. 8 illustrates a preferred method of selectively forming the metal islands 5, 15 by self assembly using angled deposition. In this method, the metal is directed onto the ridges 21 in a non perpendicular direction with respect to tops of the ridges. For example, if the ridges contain a flat upper surface 23, then the metal may be directed at an angle of 20 to 70 degrees, such as 30 to 50 degrees, with respect to the flat upper surfaces 23 of the ridges.

Preferably, the metal islands 5,15 are deposited on the ridges 21 by evaporation (thermal or electron beam), as shown in FIG. 8. In the evaporation method, the metal is evaporated thermally or by an electron beam from a metal source or target 31 onto the substrate 3, 13. For angled deposition, the substrate 3, 13 is inclined by 20 to 70 degrees, such as 30 to 50 degrees, preferably 45 degrees, with respect to the target 31. Since the spaces between the ridges 21 are sufficiently small, no metal is deposited between the ridges during the angled deposition. Thus, the tilt angle theta of the substrate should be sufficient to prevent metal deposition between the ridges 21. The metal islands 5, 15 may also be deposited by any other suitable angled or nonangled metal deposition method, such as metal organic chemical vapor deposition (MOCVD), molecular beam epitaxy (MBE), sputtering and other suitable methods.

The ridges 21 may be formed on the substrate 3, 13 by any suitable method. Preferably, the ridges are made using lithography. Most preferably, the ridges are made using photolithorgraphy, as will be described in more detail below. However, the ridges 21 may be made by using imprint or nanoindentation lithography such as, by stamping a transparent unitary or multilayer substrate with a ridged stamp to form a plurality of ridges and grooves in the transparent substrate.

Figure 9A:
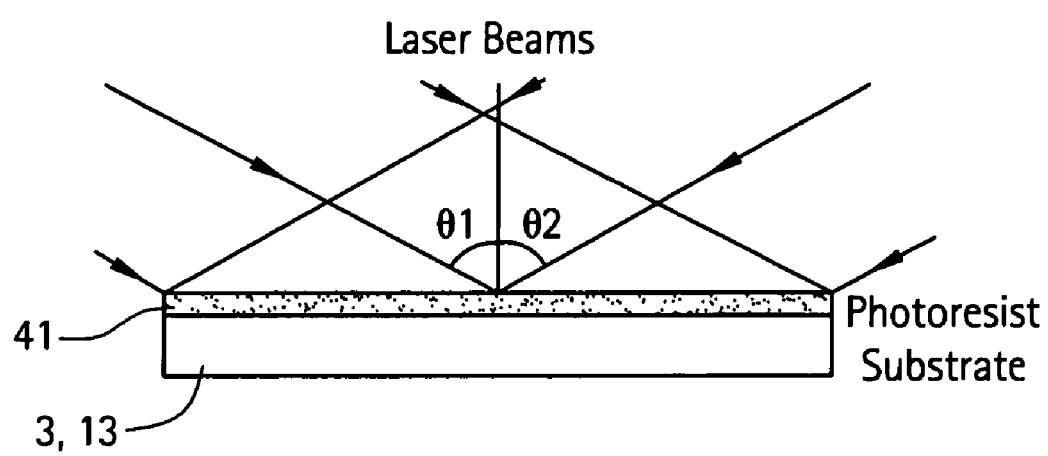
FIGS. 9A and 9B are schematic side cross sectional views of a method of making a device according to the preferred embodiments of the present invention.
Figure 9B:
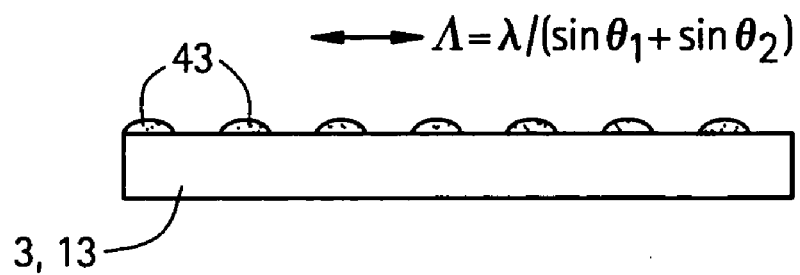
Figure 9C:
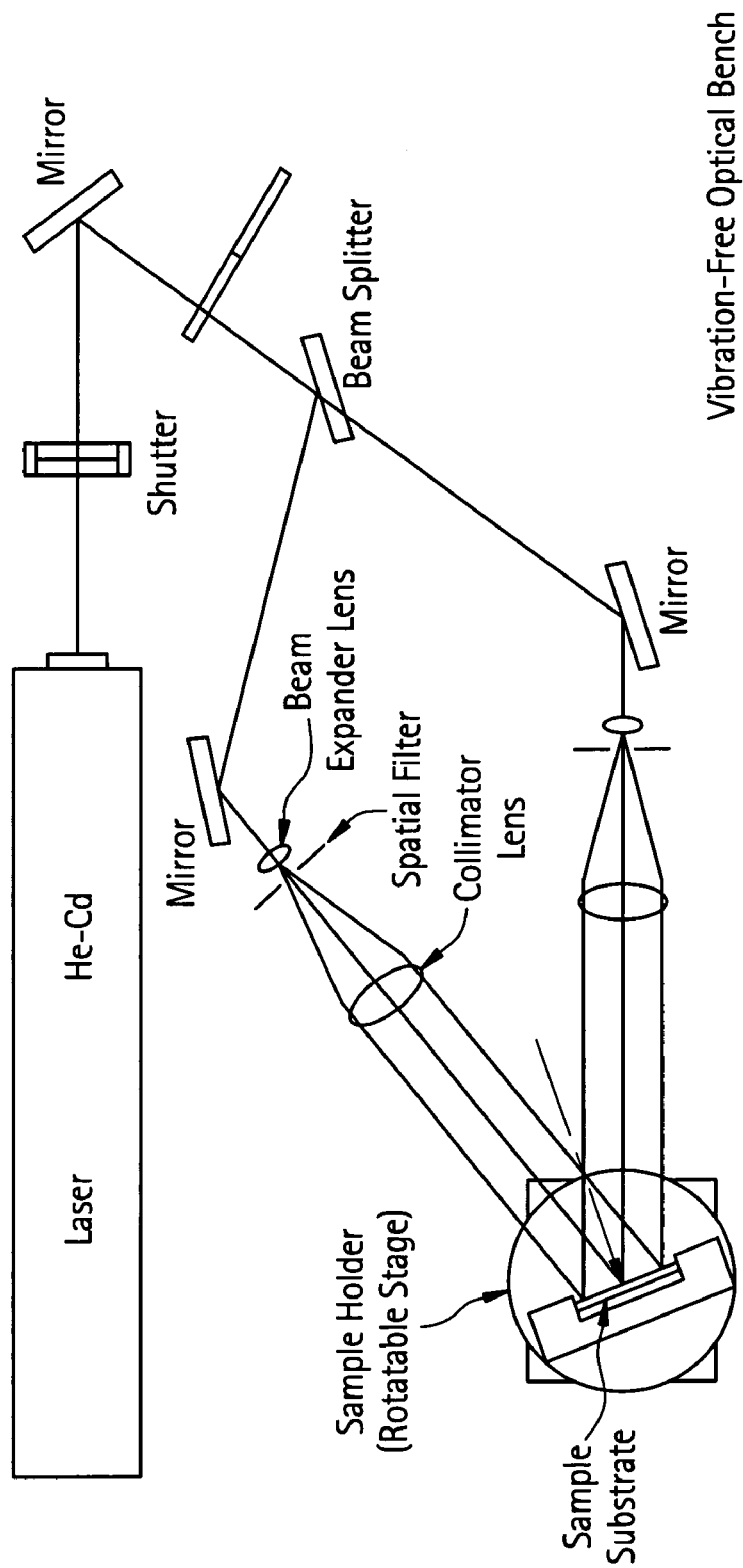
FIG. 9C is a schematic top view of a holographic lithography system.

FIGS. 9A, 9B and 9C illustrate one preferred method of forming the ridges in a transparent substrate (i.e., a unitary substrate or a multilayer substrate) 3, 13 or in a layer over the photodetector 203 using photolithography. As shown in FIG. 9A, a photoresist layer 41 is formed on the first surface of the substrate 3, 13 (or photodetector 203). The term "photoresist layer" includes any suitable positive or negative photosensitive layer used for semiconductor and other microdevice patterning. The photoresist layer 41 is then selectively exposed by radiation, such as UV or visible light, or by an electron beam.

The selective exposure can take place through a mask, by selectively scanning a narrow radiation or electron beam across the photoresist layer 41 or holographically. For example, as shown in FIGS. 9B and 9C, the photoresist layer may be separately exposed holographically for each cell of the wavelength separation device or the entire layer may be exposed at the same time for a chirped grating pattern.

To perform holographic lithography, a laser beam is split into two beams. The two beams are then reflected so that they converge together onto the photoresist layer 41. Where the two beams converge, an interference pattern comprised of multiple parallel lines of intense light is generated. The parallel lines of intense light occur with a particular periodicity which may be adjusted by changing the incident beam angle. Further adjustment of the periodicity may be accomplished by changes in optics, e.g., changes in the wavelength of the light source, and/or the refractive index of the ambient dielectric adjacent to the photoresist. Thus, the photoresist is exposed where the two beams converge and not exposed where the two beams do not converge. The length, $\Lambda$, shown in FIG. 9B is equal to the peak wavelength of the split laser beams divided by ($\sin \theta_1 + \sin \theta_2$), where $\theta_1$ and $\theta_2$ are the angles of the laser beams with the normal to the photoresist surface, as shown in FIG. 9A.

The selective exposure leaves the photoresist layer 41 with exposed and non-exposed regions. The holographic exposure is preferred because it forms slit shaped exposed and non-exposed regions in the photoresist layer 41 which can then be used to form slit shaped ridges and grooves in the substrate.

The exposed photoresist layer 41 is then patterned, as shown in FIG. 9B. If the photoresist layer 41 is a positive photoresist layer, then the exposed regions are removed by a suitable solvent, while leaving the unexposed regions as a photoresist pattern 43 on the substrate 3, 13, as shown in FIG. 9B. If the photoresist layer 41 is a negative photoresist layer, then the unexposed regions are removed by a suitable solvent, while leaving the exposed regions as a photoresist pattern 43 on the substrate 3, 13.

The upper surface of the substrate 3, 13 is then etched to form the ridges using the patterned photoresist layer 41 as a mask (i.e., using the exposed or non-exposed regions 43 remaining on the substrate as a mask). The substrate may be patterned by wet and/or dry etching. It should be noted that other intermediate processing steps, such as photoresist baking, cleaning, etc., may also be added as desired.

Furthermore, if desired, a hardmask layer, such as a silicon nitride, silicon oxide, silicon oxynitride or a metal layer, such as a chromium layer, may be added between the photoresist layer 41 and the substrate 3, 13 if needed, as shown in FIGS. 9D-9I. As shown in FIGS. 9D and 9E, hardmask layer 42, such as a Cr layer, is formed on the substrate 3, 13. A photoresist pattern 43 is then formed on the hardmask layer 42 by any suitable method, such as the holographic lithography method, as shown in FIG. 9F. The hardmask layer 42 is then patterned using the photoresist pattern 43 as a mask to form a hardmask pattern 44, and then the photoresist pattern 43 is removed, as shown in FIG. 9G. The substrate 3, 13 is then patterned to form the ridges 21 using the hardmask pattern 44 as a mask, as shown in FIG. 9H. The hardmask pattern 44 is then removed. The metal islands 5 are then selectively deposited on the ridges 21, such as by angled deposition, as shown in FIG. 9I.

A preferred example of the parameters of the method described above is as follows. An about 40 nm thick Cr hardmask layer is deposited on a quartz substrate by thermal evaporation. This is followed by HMDS application and photoresist spin coating to a thickness of about 100 nm on the hardmask layer. Microposit Photoresist 1805 and Microposit Type P Thinner in 1:1 volume ratio is used with a spin speed 5000 rpm. The photoresist layer was then subjected to a softbake at 95 degrees Celsius for 30 minutes. The photoresist is exposed by holographic lithography. A UV He—Cd laser (325 nm wavelength, 15 mW CW power) is used for the exposure. The photoresist layer is then developed using Microposit 351 and DI water in 1:4 volume ratio. The developed (i.e., patterned) photoresist is then subjected to a hardbake at 120 degree Celsius for 30 minutes.

The Cr hardmask layer is then etched using the patterned photoresist layer as a mask. The Cr layer is etched using a reactive ion etching (RIE) system (PlasmaTherm 790 ICP/RIE) in a two step etching process. In step 1, $Cl_2$ (20 sccm)+$O_2$ (10 sccm) at 10 mTorr pressure, RIE power of 25 W and ICP power of 100 W for 30 seconds are used. In step 2, $Cl_2$ (24 sccm)+$O_2$ (6 sccm) at 10 mTorr pressure, RIE power of 10 W and ICP power of 100 W for 7 minutes are used.

The patterned hardmask layer is then used as a mask to pattern the quartz substrate. The quartz substrate is etched by RIE using $CF_4$ (37 sccm)+$O_2$ (4 sccm) at 15 mTorr, RIE power of 100 W and ICP power of 150 W for 12 minutes. Thereafter, the remaining Cr hardmask is removed by chemical etching with $NaOH+K_3Fe(CN)_6+H_2O$ solution. The Ag islands are then deposited on the mesa etched substrates using angled deposition. The Ag islands are deposited to various thicknesses using thermal evaporation of Ag source in a base pressure of $10^{-5}$ Torr with a tilt angle of 45 degrees. The holographically-patterned and mesa-etched substrates, once made, can be utilized as a master mold in nanoimprinting the array patterns on substrates without involving any separate optical or electron lithography process each time of pattern definition or transfer.

Figure 10A:
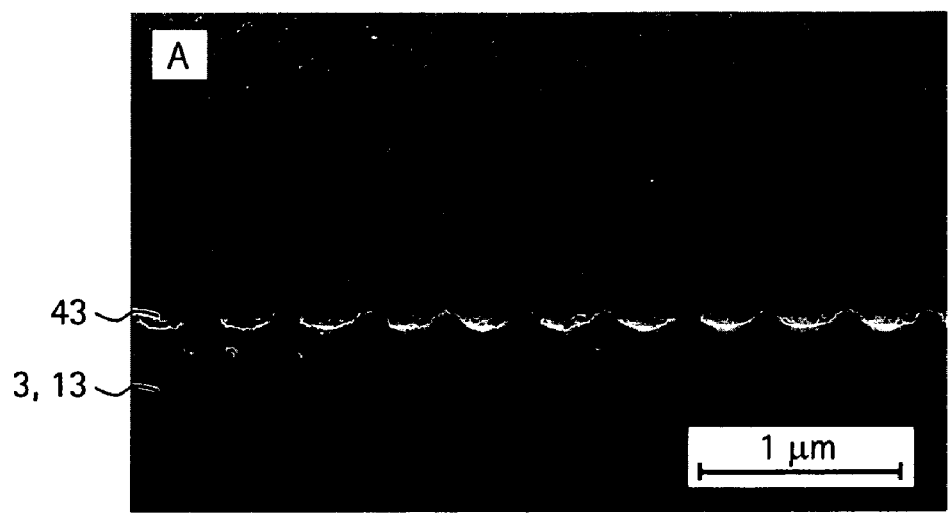
FIGS. 10A, 10B and 10C are micrographs of a method of making a nanopore array according to the preferred embodiments of the present invention.
Figure 10B:

FIGS. 10A and 10B illustrate another preferred method of forming the ridges in a transparent substrate (i.e., a unitary substrate or a multilayer substrate) 3, 13 or over the photodetector 203 using photolithography and a nanopore array. One exemplary method of forming a nanopore array is described in Z. Sun and H. K. Kim, Appl. Phys. Lett., 81 (18) (2002) 3458.

First, as shown in FIG. 10A, a photoresist pattern 43 in a shape of a grating is formed on the substrate 3, 13 or over the photodetector 203 in the same manner as described above and as illustrated in FIGS. 9A-9B. The photoresist pattern may be formed by holographic or non-holographic lithography. After forming the photoresist pattern 43, the substrate 3, 13 may be etched to transfer the grating pattern to the substrate to form ridges 21 illustrated in FIG. 7, after which the photoresist pattern 43 is removed. Alternatively, the substrate etching and photoresist pattern removal steps may be omitted.

A metal layer 51 capable of being anodically oxidized is conformally deposited over the ridges 21, if the ridges are present, or over the photoresist pattern 43, if the photoresist pattern has not been removed, as shown in FIG. 10B. The conformally deposited metal layer 51 assumes the grating pattern of the underlying substrate or photoresist pattern, as shown in FIG. 10B. In other words, the metal layer 51 is formed on a grating patterned transparent substrate (i.e., a ridged substrate or a patterned photoresist 43 covered substrate) such that the grating pattern of the substrate 3, 13 is translated to an upper surface of the first metal layer 51.

The metal layer 51 may comprise any suitable metal, such as Al, Ta, Ti, Nb and their alloys, which may be anodically anodized. The metal layer 51 may be deposited by any suitable method, such as sputtering, MOCVD, evaporation (thermal or electron beam), MBE, etc. The metal layer 51 may have any suitable thickness, such as 100 to 1000 nm, preferably 350-400 nm. The corrugation depth in the upper surface of the metal layer 51 is preferably about the same as the corrugation depth of the substrate or the photoresist pattern. Preferably, the corrugation depth of the metal layer 51 is about 20 to about 300 nm, such as about 80 to 100 nm.

Figure 10C:
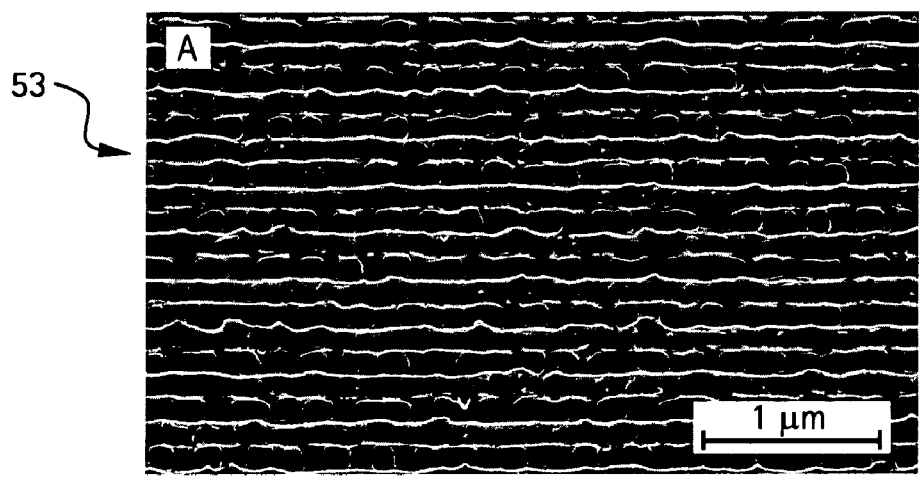

The metal layer 51 then is oxidized anodically, by any suitable method. For example, an Al layer 51 on a silica substrate 3, 13 may be anodically oxidized in dilute electrolyte ($1H_3PO_4 + 800H_2O$ in volume ratio) at room temperature using a platinum wire as a counter electrode. The anodization is preferably conducted under a constant voltage mode for about 40 minutes. The anodic voltage is chosen such that the expected pore distance matches the grating period, for example 140 volts for a 350 nanometer grating period. In a naturally-formed alumina pore array, the interpore distance is proportional to the anodization voltage, i.e. about 2.5 nanometers/volt. The voltage may be varied for anodizing different portions of the metal layer to form pores with a variable period. After anodization, the samples are preferably treated with phosphoric acid (diluted with water in a 1:3 volume ratio) for one to two minutes. FIG. 10C is a electron micrograph of a nanopore array 53 grown in the grating patterned aluminum layer 51 when the aluminum layer 51 is converted to aluminum oxide by anodic oxidation. The resulting alumina pores exhibit a uniform depth, such as about 100 to 2000 nm, preferably about 300 to 400 nm and the pore bottom has a concave, hemispherical shape with barrier thickness of about 100 to 300 nm, such as 150 to 200 nm. The preferred pore diameter is about 5 to 100 nm, such as 5 to 10 nm. The nanopores selectively form in troughs of the grating pattern in the upper surface of the anodically oxidized metal layer 51.

Figure 10D:
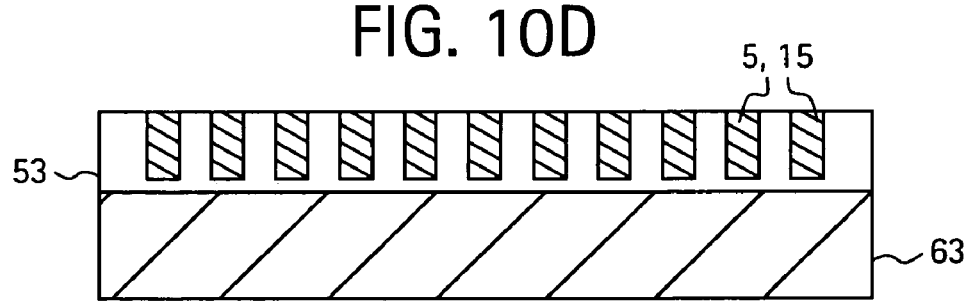
FIG. 10D is a schematic side cross sectional view of a device according to the preferred embodiments of the present invention.
Figure 10E:
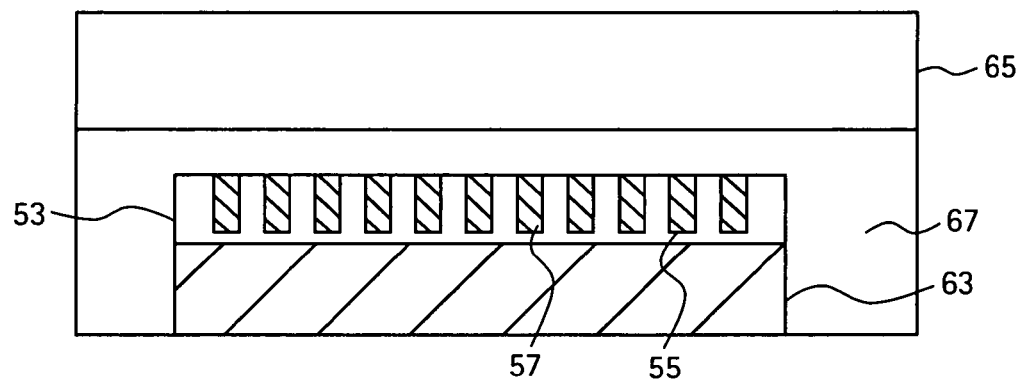
FIG. 10E is a schematic side cross sectional view of an electroplating bath used to make the device of FIG. 10D.

After forming the nanopore array 53, such as the array shown in FIG. 10C, metal islands 5, 15 are selectively grown in the nanopores, as shown in FIG. 10D. One preferred method of selectively growing metal islands inside the nanopores in a metal oxide layer is an electroplating method illustrated in FIG. 10E. The nanopore array 53 is formed on a conductive or a semiconducting substrate 63. The substrate 63 may comprise a metal layer, such as a metal layer which is not anodically oxidized, or a doped semiconductor layer, such as silicon, gallium arsenide or gallium nitride. The substrate 63 may comprise the radiation transparent substrate 3, 13 used in the devices 1, 11 or the substrate 63 may comprise a temporary substrate which is transparent or non-transparent to radiation. The substrate 63 and array 53 are then provided into an electroplating bath 65 containing a liquid metal 67. A potential difference (i.e., a voltage) is applied between the substrate 63 and the array 53. Since the array 53 is thinner in regions 55 below the nanopores 57, a voltage gradient exists in these regions 55. This causes the metal 67 from bath 65 to selectively deposit into the nanopores 57. If desired, the electroplating method may be used to selectively fill the nanopores 57 with metal 67 from bath 65. The metal 67 may be any metal which exhibits the previously described plasmon enhancement effect and which may be deposited into metal oxide pores by electrodeposition, such as Ni, Au, Pt and their alloys. Thus, the islands 5, 15 are formed by filling the nanopores 57 with the electroplated metal 67. A metal island array suitable for monochromator and image analyzer applications and having a structure complementary to the structure illustrated in FIG. 2C may be formed by filling nanopores with electroplated metal.

In an alternative preferred aspect of the present invention, the nanopores 57 are filled only part of the way with the metal 67 during the electroplating step. In this case, the metal 67 may be any metal which can act as a catalyst for selective metal vapor deposition. For example, the metal 67 may be Au. The array 53 with the catalyst metal 67 formed on the bottom of the nanopores 57 is then transferred to a metal vapor deposition chamber, such as a chemical vapor deposition chamber. Metal islands 5,15 are then selectively grown on the catalyst metal 67 by selective vapor deposition. The metal islands 5, 15 may comprise any metal which exhibits the previously described plasmon enhancement effect and which may be selectively deposited on a catalyst metal 67, but not on metal oxide walls of the nanopore array 53. For example, this metal may comprise Al or Ag.

If the nanopore array 53 is formed on a temporary substrate 63, then the temporary substrate may be removed from the array 63 before or after the formation of the metal islands 5, 15 on the array 53. The temporary substrate may be removed by selective etching, polishing or chemical mechanical polishing of the substrate, by selective etching of a release layer (not shown for clarity) located between the temporary substrate 63 and the array 53, or by peeling the substrate 63 away from the array 53. In case of peeling, one or more peel apart layers may be located between the substrate 63 and the array 53. The peel apart layer(s) have a low adhesion and/or strength such that they can be separated mechanically from each other or from the array and/or the substrate. The transparent substrate 3, 13 or the photodetector 203 is then attached to the array 53 before or after forming the metal islands 5,15 on the array, on the same and/or opposite side of the array 53 from where the temporary substrate 63 was located.

In an alternative, preferred aspect of the present invention, a metal film with a plurality of openings, such as a metal film shown in FIG. 2C is formed by angled deposition of metal on the ridges of a nanopore array. The angled deposition method is described above and illustrated in FIG. 8. In another alternative aspect of the present invention, a metal layer is deposited over the nanopore array such that metal extends into the pores, and the metal layer is then chemically mechanically polished or etched back to expose top portions of the nanopore array. The polishing or etch back step leaves discrete metal islands in the nanopores, separated by the metal oxide nanopore array transparent regions.

In another alternative aspect of the present invention, the nanopore array is formed without first patterning the substrate 3, 13 or forming the photoresist pattern 43. In this aspect, a metal layer 51, such as an Al, Ta, Ti or Nb layer is deposited on the unpatterned substrate or over the photodetector 203. Then corrugations are formed in the metal layer 51 by any suitable method. For example, the corrugations may be formed by selective laser ablation of the metal layer, by nanoindentation or nanoimprinting, or by photolithography (i.e., by forming a photoresist pattern on the metal layer, then etching the metal layer using the pattern as a mask and removing the photoresist pattern). Preferably, holographic photolithography is used to pattern the metal layer 51, and a temporary silicon nitride, silicon oxide or silicon oxynitride hard mask is used between the photoresist and the metal layer 51. Then, the metal layer 51 is anodically oxidized as described above.

Figure 11A:
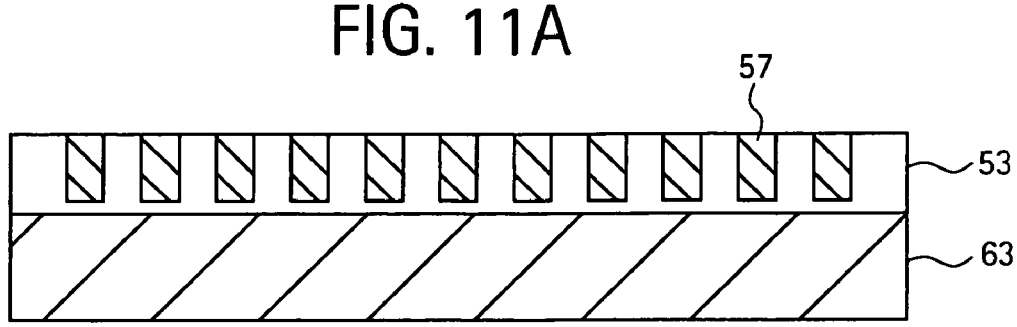
FIGS. 11A, 11B, 11C and 11D are schematic side cross sectional views of a method of making a device according to the preferred embodiments of the present invention.
Figure 11B:
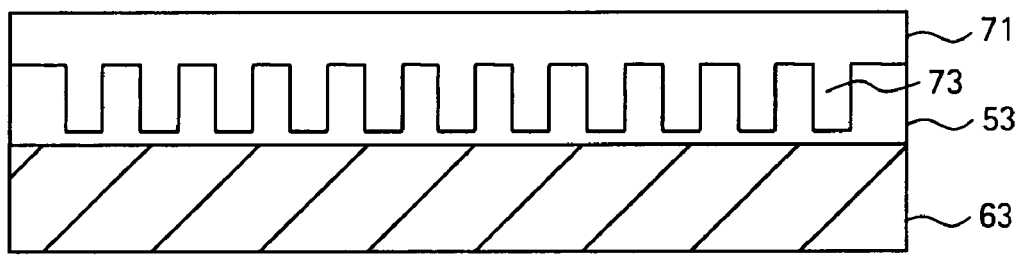

FIGS. 11A-D illustrate an alternative method of forming the metal islands using a templated nanopore array. As shown in FIG. 11A, the metal oxide nanopore array 53 on substrate 63 is formed using the method described above and illustrated in FIGS. 10A-10C. Then, a conformal template material 71 is deposited over the array 63, as shown in FIG. 11B. The conformal template material 71 may comprise any material which can conformally fill the nanopores 57 of the array 53. For example, the conformal template material 71 may comprise silicon oxide, silicon nitride, a glass heated above its glass transition temperature, a CVD phospho- or a borophosphosilicate glass (PSG or BPSG, respectively), a spin on glass or a polymer material. If desired, the conformal template material may comprise all or part of the transparent substrate 3, 13.

Figure 11C:
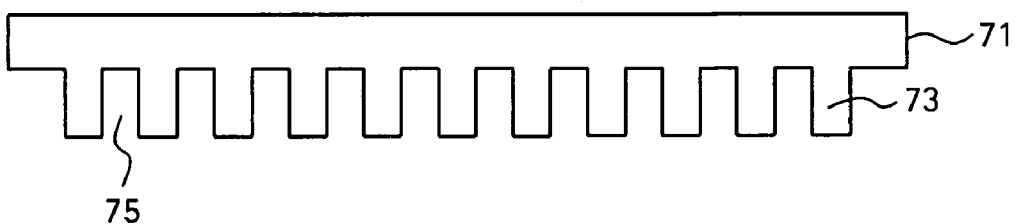
Figure 11D:

Then, as shown in FIG. 11C, the conformal template material 71 is removed from the nanopore array 53. The conformal template material 71 contains ridges 73 which previously extended into the nanopores 57 of the array. Then, the metal islands 5,15 are selectively deposited into the pores 75 between the ridges 73 of the conformal template material 71 using the electroplating method or on the ridges 73 using angled deposition method as described above. If the conformal template material 71 is the transparent substrate 3, 13 material, then the process stops at this point. If the conformal template material 71 is not the transparent substrate 3, 13, then the conformal template material 71 is separated from the metal islands 5, 15 by any suitable method, such as selective etching, polishing or chemical mechanical polishing. The metal islands 5, 15 are attached to the transparent substrate 3, 13 before or after removing material 71.

Figure 12A:
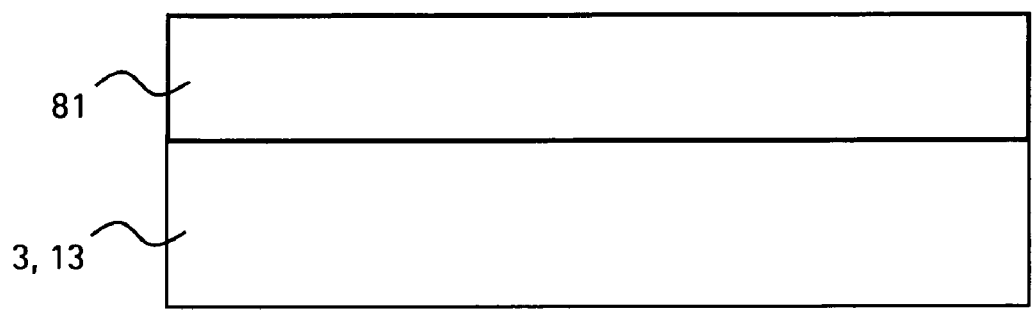
FIGS. 12A and 12B are schematic side cross sectional views of a method of making a device according to the preferred embodiments of the present invention.
Figure 12B:
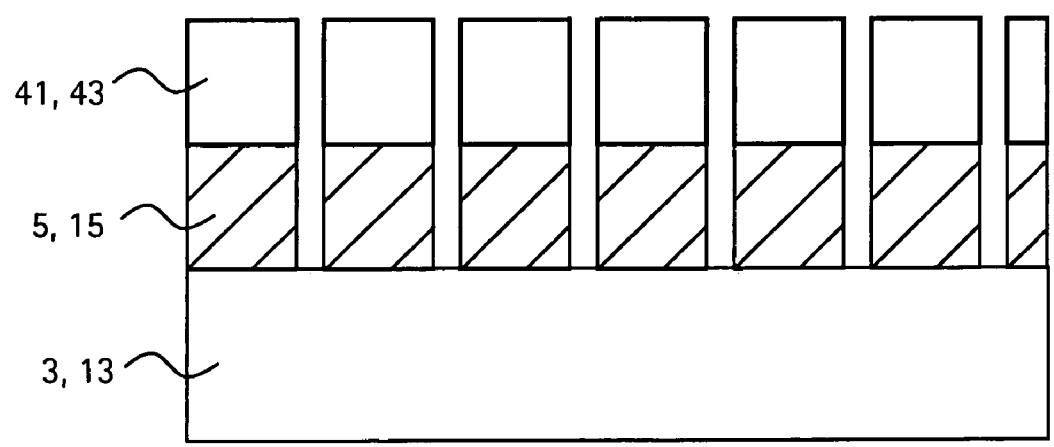

FIGS. 12A and 12B illustrate an alternative method of forming the metal islands 5, 15 without using ridges on a substrate or over the photodetector 203 and without using a nanopore array. In this method, a metal layer 81 is formed on the substrate 3, 13, as shown in FIG. 12A. The substrate 3, 13 may contain features on its upper surface or it may contain a flat upper surface. The metal layer 81 is then patterned into a plurality of metal islands 5, 15 as shown in FIG. 12B. The metal layer 81 may be patterned lithographically as described previously. Thus, a photoresist layer 41 is formed on a first surface of the metal layer 81. The photoresist layer is selectively exposed to form exposed and non-exposed regions. The exposed photoresist layer is patterned into pattern 43 and the metal layer is etched into the plurality of islands 5, 15 using the patterned photoresist layer as a mask.

The photoresist layer may be exposed holographically or non-holographically. If desired, an optional, temporary hardmask layer described above may be formed between the metal layer 81 and the photoresist. Alternatively, the metal layer may be patterned by selective laser ablation or other non-photolithographic methods instead of by photolithography.

Figure 13A:
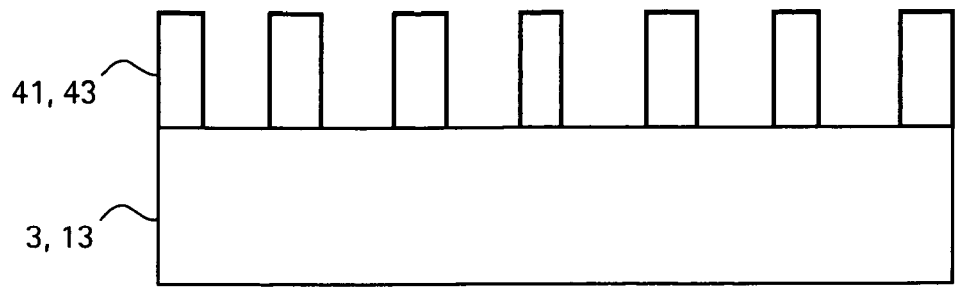
FIGS. 13A, 13B, and 13C are schematic side cross sectional views of a method of making a device according to the preferred embodiments of the present invention.
Figure 13B:
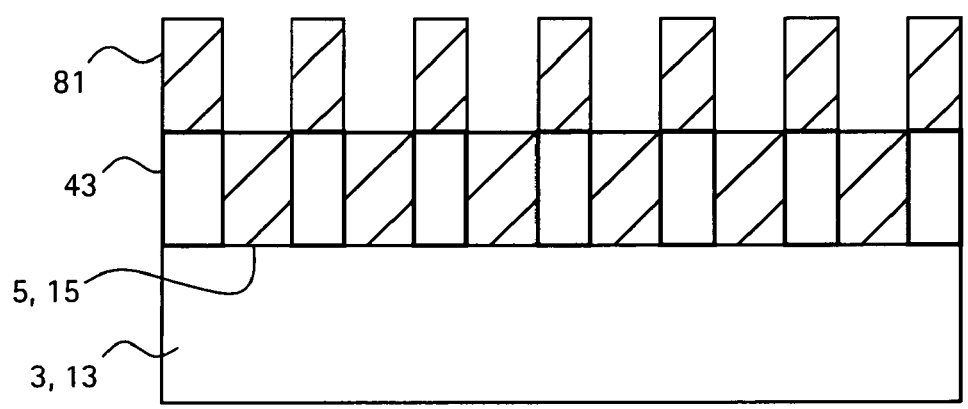
Figure 13C:
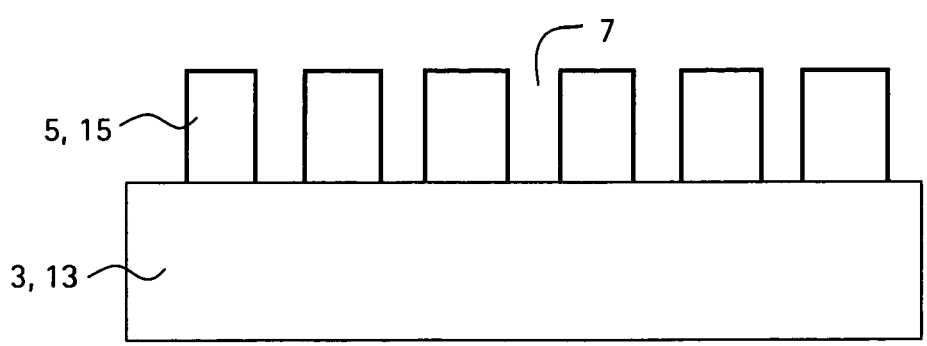

FIGS. 13A, 13B and 13C illustrate an alternative lift off method of forming the metal islands 5, 15. This method also does not require using ridges on a substrate or a nanopore array. In this method, a photoresist layer 41 is formed on the substrate 3, 13 or over the photodetector 203 as shown in FIG. 13A. The substrate 3, 13, may contain features on its upper surface or it may contain a flat upper surface. The photoresist layer is selectively exposed to form exposed and non-exposed regions. The photoresist layer may be exposed holographically or non-holographically.

The exposed photoresist layer 41 is then patterned to form a photoresist pattern 43, exposing portion of the upper surface of the substrate 3, 13. As shown in FIG. 13B, a metal layer 81 is formed over the photoresist pattern 43 and over exposed portions of the upper surface of the substrate 3, 13.

As shown in FIG. 13C, the photoresist pattern 43 is then lifted off, such as by selective etching or other suitable lift off techniques. Portions of the metal layer 81 located on the photoresist pattern 43 are lifted off with the pattern 43 to leave a plurality of metal islands 5, 15 on the upper surface of the substrate 3, 13.

Figure 14:
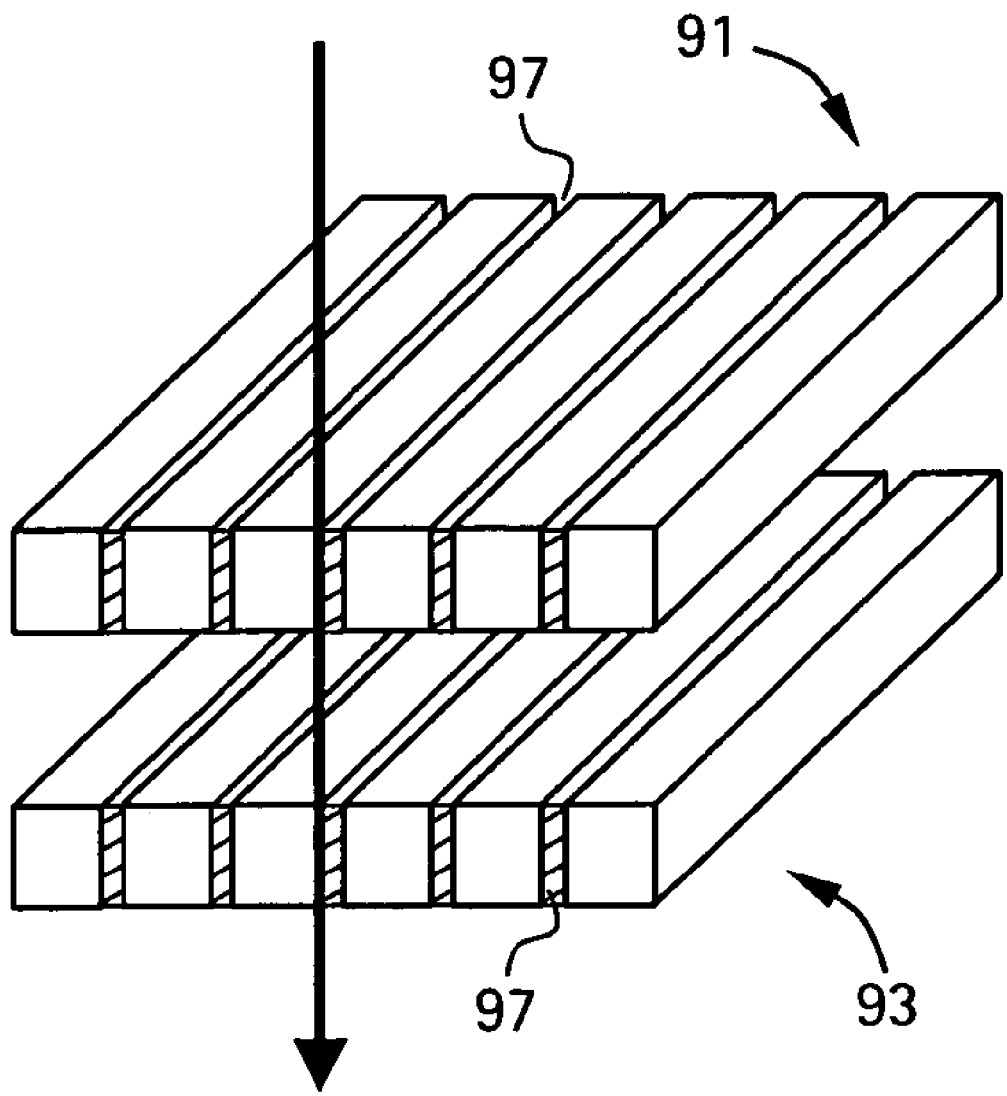
FIG. 14 is a three dimensional view of a device according to the preferred embodiments of the present invention.

In order to improve further the passband characteristics of the optical devices 1, 11, a three dimensional stacked structure of metal film or metal island layers 91, 93 may be used, as shown in FIG. 14. Two pieces of single-layer 1D optical devices 91, 93 are vertically stacked face-to-face, with grating lines (i.e., slit shaped transparent regions) 97 substantially parallel to each other, and with the spacing between faces in a far field regime, where the far field regime comprises spacing that is greater than about 3 to 5 times the wavelength of the incident light or radiation. The transparent regions 97 may be slightly offset from each other by an amount that still allows radiation transmission through both layers. The two metal film or island layers are then expected to interact in the farfield regime, and therefore the overall transmission would be basically a product of two transmission profiles. This will result in suppression of lower intensity side peaks and background transmission and also will narrow the width of the main peak. Overall, the use of a three-dimensional stacked structure of metal film or metal island layers will enhance the bandpass characteristics of the optical filter arrays.

The present inventors have also discovered that localized surface plasmon (SP) resonance can occur at metal islands or in a metal film in an array of slit shaped transparent regions aligned in one direction between the metal islands or in the metal film, but not in an array of non-slit shaped apertures in a metal film. The transmission of radiation is higher through the array of slit shaped transparent regions between the metal islands or in the metal film than through the array of non-slit shaped apertures in a metal film.

Furthermore, the present inventors have discovered that in the array of slit shaped transparent regions between the metal islands, the width of the slit shaped transparent regions and the metal island height (i.e., thickness) determine the transmission characteristics of these arrays. Without wishing to be bound by a particular theory, the present inventors believe that the localized SP resonance is responsible for this effect. When the transparent region width is within a preferred range, high transmission in the main passband wavelength and low transmission in the long wavelength range may be achieved. The preferred range is between about one and about three times the penetration depth of SP fields in the metal islands. Most preferably, the width is greater than 30 nm and less than 100 nm. This range is preferable for the visible spectrum of light, and the preferred slit width will proportionally increase for the longer wavelength regime. This feature of 1D metal island/slit shaped transparent region arrays may be used in designing and/or developing spectral characteristics of wavelength separation devices. In contrast, when the transparent region width is greater than this preferred range, the transmission at a main passband wavelength and in the long wavelength range is high. When the transparent region width is less than this preferred range, it results in extremely low transmission at the main passband wavelength and in the long wavelength range.

Without wishing to be bound by a particular theory, the present inventors believe that two types of surface plasmon excitation are responsible for the characteristics of the radiation transmitted through the slit shaped transparent regions between metal islands or in the metal film: 1) the SP resonance along the planes that comprise either the metal/air or metal/substrate interfaces, and 2) the SP resonance localized along the surface that encloses each metal island separated by the slit shaped transparent region (i.e., the metal island sidewalls or transparent region sidewalls in a metal film).

The present inventors also believe that a peak transmission occurs in a device where the localized SP resonance is slightly off-tuned from the plasmon resonance at the metal/substrate surface. It is then expected that in such devices, the main passband transmission will remain high while the long-wavelength transmission will be low. Furthermore, the height (i.e., thickness) of the metal islands or metal film affects the width of the main passband peak. Generally, the width of the main passband peak decreases with a decreasing metal island or film thickness. It should be noted that the device ideally contains one passband at one peak wavelength. However, the devices may contain more than one passband with more than one peak wavelength.

In some aspects of the present invention, metal islands separated by subwavelength radiation transparent regions may be used for the plasmon enhanced transmission of radiation instead of subwavelength aperture(s) in a metal film. Preferably, the metal islands are formed using lithography and/or self assembly to simplify processing and to increase the precision of the optical device.

In one preferred aspect of the present invention, the metal islands spaced apart by radiation transparent regions are formed by self assembly. In other words, rather than forming a metal film and patterning the film into metal islands, the spaced apart metal islands are formed simultaneously or sequentially without first being part of an unpatterned metal film. The metal islands may comprise discrete metal islands that are not connected to each other (i.e., the metal islands are not in direct contact with each other) or metal islands that are connected to each other at a peripheral region of the optical device.

In another preferred aspect, the metal islands comprise discrete islands that are formed by patterning a metal film into the islands. Preferably, the islands are patterned using a lithographic method.

FIG. 19A illustrates a surface plasmon resonant optical device 1 which includes a radiation transparent substrate 3 and a plurality of metal islands 5 on the substrate 3. The metal islands 5 are separated by a plurality of radiation transparent regions 7. FIG. 19B illustrates a side cross sectional view of the device 1 along line A-A'.

Any suitable materials may be used for the substrate 3 and the metal islands 5. For example, any radiation transparent material (i.e., visible light, UV and IR transparent material) may be used as the substrate material. For example, the substrate 3 may comprise glass, quartz, ceramic, plastic or semiconductor material. The substrate 3 may comprise a plurality of films or layers or it may comprise a unitary body.

Any metal which exhibits surface plasmon resonance effects (i.e., a negative epsilon material) may be used as the metal island 5 material. For example, metals such as silver, gold, copper and aluminum and alloys thereof which exhibit a bulk plasmon frequency about 9-10 eV, are preferred as the metal island material.

Adjacent metal islands 5 are separated by a distance 9 which is less than at least one first predetermined wavelength of incident radiation to be provided onto the device 1. Preferably the distances is less than 100 nm, such as 40-60 nm. This range is preferable for the visible spectrum of light, and the preferred distance will proportionally increase for the longer wavelength regime. The metal islands 5 are configured such that the incident radiation is resonant with a surface plasmon mode on the metal islands, thereby enhancing transmission of radiation between the plurality of metal islands. Preferably the transmitted radiation has at least one peak wavelength whose transmission is enhanced by the surface plasmon resonance.

Any suitable radiation may be used as incident radiation. For example, the incident radiation may comprise visible light, UV or IR radiation. The incident radiation may comprise radiation with a narrow wavelength distribution, such as radiation with a peak wavelength and narrow band width around the peak wavelength, or radiation with a wide distribution of wavelengths, such as white light. For example, radiation having wavelengths greater than the plasmon wavelength of the metal islands may be used. For example, for silver islands, the plasmon wavelength is about 350 nm. Thus, radiation having wavelengths ranging from about 350 nm to microwave wavelengths may be used. If silicon photodetectors are used to detect the radiation, then a preferred incident radiation wavelength range is about 350 nm to about 1100 nm.

Preferably, radiation having a peak wavelength less than 700 nm, such as 400 nm to 700 nm (i.e., visible light) is used as the incident radiation. In this case, the metal islands 5 are separated by a distance 9 of 700 nm or less, such as by 15 to 200 nm, preferably 40 to 60 nm.

The metal islands 5 may have any suitable thickness such that the islands 5 themselves are opaque to radiation but will generate plasmon enhanced radiation transmission through regions 7. Preferably, metal island thickness should be at least about two or three times the skin depth of metal. In silver islands with incident radiation in a visible wavelength range, the skin depth is around 30 nm, and the metal island thickness should be at least about 60 to 90 nm or greater. The skin depth increases for longer wavelength range and is somewhat different for different metals. Thus, for example, the metal islands 5 may have a thickness of about 50 nm to about 2000 nm, such as 100 nm to 400 nm, preferably 120 to 180 nm.

In a one embodiment of the present invention, the plasmon enhancement of the transmitted radiation occurs due to the period or spacing of the transparent regions 7 between the metal islands. For example, as shown in FIG. 19A, the plurality of metal islands have a width 10, thereby forming an array of transparent regions between the plurality of metal islands with a period, $a_o$, equal to the width 10 of the islands 5 plus the width 9 of the transparent regions. The period $a_o$ of the transparent regions 7 is selected based on the wavelength(s) of the incident radiation that will be used to irradiate the device 1 in order to enhance the transmission of radiation by plasmon resonance. Preferably, the period of the transparent regions, $a_o$, is about three to ten, such as five to six times as large as the width of the transparent regions 7. Thus, for a preferred width 9 of about 30 to 100 nm of the transparent regions 7 for incident visible light, the period $a_o$ is about 200 nm to about 780 nm, for example, 200 nm to 700 nm, such as about 370 nm to about 700 nm. However, the period $a_o$ may range from about 60 nm to about 2 microns, such as 0.1 to 1.8 microns.

As shown in FIG. 19A, the transparent regions 7 are slit shaped. These slits have a length that is significantly larger than the width 9. Preferably, the length is at least ten times larger than the width 9. However, the transparent regions 7 may have any other suitable shape instead of a slit shape which results in plasmon enhanced transmission of radiation.

Without wishing to be bound by a particular theory, the present inventors believe that two types of surface plasmon excitation are responsible for the characteristics of the radiation transmitted through the slit shaped transparent regions between metal islands: 1) the SP resonance along the planes that comprise either the metal/air or metal/substrate interfaces, and 2) the SP resonance localized along the surface that encloses each metal island separated by the slit shaped transparent region (i.e., the metal island sidewalls).

Figure 20A:
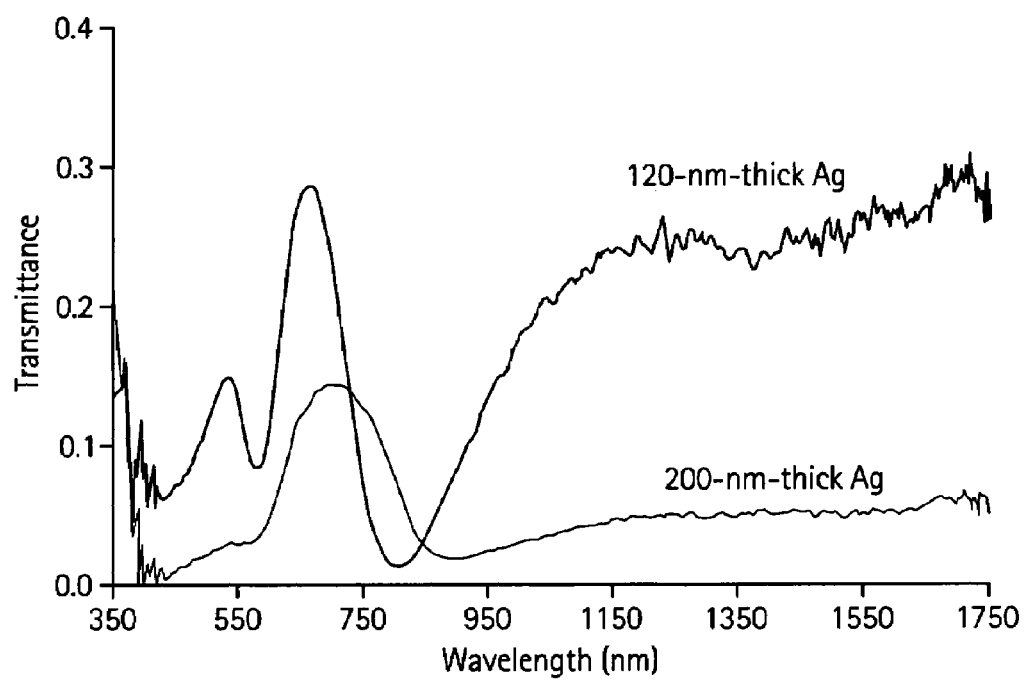
FIGS. 20A and 20C are graphs of the transmission spectra of devices according to examples of the present invention.

FIG. 20A shows the transmission spectra of the devices made according to examples 1 and 2, described in more detail below. The devices include metal islands with a grating period of 370 nm. The device of example 1 contains 120 nm thick Ag islands having a minimum (i.e., width at the narrowest point) transparent region 7 width of about 50 to 100 nm. The device of example 2 contains 120 nm thick Ag islands having a minimum transparent region 7 width of about 30 nm. Optical transmission through the devices is measured at a spectral range of 350-1750 nm. A beam from a multimode fiber (core diameter of 62.5 μm and a numerical aperture of 0.20) connected to an unpolarized white light source is normally incident to the metal island array from the substrate side. The zero-order transmission through the array is collected with another multimode fiber placed close to the Ag layer surface (with 3-5 μm gap), and is then characterized with an optical spectrum analyzer. The transmission measurement is repeated with a dummy sample that has the same mesa-etched quartz structure but without an Ag layer. The transmission through the array is then calculated by dividing the spectrum obtained from a real sample by the one from the dummy, a process designed to void (or alleviate) the effects of involving a mesa-etched quartz substrate structure and an optical fiber on the measured transmission spectra.

As shown in FIG. 20A, peak transmission of approximately 30 and 15% is observed from the 120 nm and 200 nm thick metal island arrays, respectively. Considering that the incident beam is unpolarized and the TE polarization component does not transmit through the array having slit shaped transparent region, the maximum transmission for TM polarization is estimated to be around 60%. This corresponds to about a 500% transmission efficiency, which is defined as the optical power transmitted through a slit divided by the incident power impinging upon the slit area.

As shown in FIG. 20A, the main peak (i.e., the peak which corresponds to the main passband wavelength range) shifts from 660 to 690 nm as the Ag island thickness is increased from 120 to 200 nm. The peak width also noticeably increased with the increased Ag thickness. These characteristics of the transmission spectra, i.e., the main peak's red-shift and the peak width increase, is the opposite of the characteristics of the transmission spectra in an 2D array of apertures in a metal film, in which the main peak initially blue-shifts with reduced peak-width and then the peak position and width remain constant as the metal thickness is further increased.

In an analytical study of the optical transmission through a 2D aperture array, the initial regime that shows a blue-shift is modeled by the evanescent coupling of the two surface plasmons at the top and bottom surfaces of a metal layer and the second regime is by decoupled SPs.

In contrast, it is believed that the propagating modes in a slit shaped transparent region are at least partially responsible for the optical transmission through an array of slit shaped transparent regions. The clear difference between the 1D and 2D array optical transmission characteristics strongly suggests that different mechanisms are involved in transmitting the light though a slit shaped transparent region than through an aperture in a film.

The transmission spectra in FIG. 20A show three major dips. The minimum transmission point at around 580 nm tends to stay at nearly the same position for different metal island thickness, although the exact location cannot be resolved due to an overlap with a neighboring peak. This insensitivity to metal thickness suggests that the phenomenon occurring at this minimum transmission point involves an interaction of light primarily with the top or bottom surfaces of metal but not the sidewalls of the metal islands. The SP resonance along the plane that comprises the metal/substrate interface of each metal island is expected to occur at 600 nm wavelength of light, based on a calculation using the formula:

$$\lambda = \frac{L}{m} \sqrt{\frac{\varepsilon_d \varepsilon_m}{\varepsilon_d + \varepsilon_m}}. \quad (1)$$

Here, L is the grating period, m is the order of the grating vector involved in SP coupling, and $\varepsilon_m$ and $\varepsilon_d$ are the dielectric constants of metal and adjacent dielectric (i.e., a quartz substrate in this case). This number calculated for m=1 reasonably well matches the minima observed in Figure 20A. Similarly the transmission minimum at around 430 nm well corresponds to the SP resonance at the air/metal interface, which is expected to occur at 430 nm according to the formula above, although an exact position cannot be clearly resolved due to an overlap with the bulk plasmon wavelength (about 360 nm) at which metal islands are significantly transparent.

It should also be noted that the sample with 120 nm thick Ag metal islands show a clear, well-defined major dip at around 800 nm, which corresponds to significantly longer wavelength than that of the transmission minima related to the metal/substrate interface. Considering that a slit shaped transparent region structure allows propagating modes (or vertical SPs along the metal island sidewalls), it is possible that the SP waves on the top and bottom surfaces of a metal island couple to each other via these island sidewalls. The SPs are then expected to resonate along the island surface, i.e., the periphery of metal cross-section when the following condition is satisfied along the close loop:

$$\oint k_{sp} \cdot dr = 2\pi m \quad (2)$$

Here, m is an integer, and $k_{sp}$ is the SP wave vector and can be expressed as $$k_{sp} = \left(\frac{2\pi}{\lambda}\right)\left(\frac{\varepsilon_m \varepsilon_d}{\varepsilon_m + \varepsilon_d}\right)^{1/2}, \qquad (3)$$

where $\lambda$ is the free-space wavelength of incident light. Along the periphery of metal cross-section, the magnitude of the SP wave vector $k_{sp}$ varies depending on the dielectric material interfacing with a metal, i.e., either air or quartz in this case. Due to the irregular geometry of the metal cross-section, an approximation may be used to calculate the total phase change along the periphery of the metal islands. Assuming a simple geometry of circular cross-section with radius $r_o$ surrounded by a homogeneous dielectric, the resonance condition in Equation 2 is reduced to $k_{sp}r_o=m$. For an approximation of $r_o=110$ nm and 30% of the metal periphery interfaces with silica and the rest with air, the resonance wavelength is calculated to be 820 nm for the dipolar resonance case, i.e., m=1. This number closely matches the location of the transmission dip (800 nm) of the sample with 120 nm thick Ag island, as shown in FIG. 20A. The minimum transmission point shifts to longer wavelength as the metal island thickness is increased. This behavior is also consistent with the resonance condition discussed above. It is important to note that this surface plasmon resonance is a phenomenon highly localized at each metal island and differs from the SP resonance that occurs along the planes that comprise either the top or bottom surfaces of an array of metal islands.

Figure 20B:
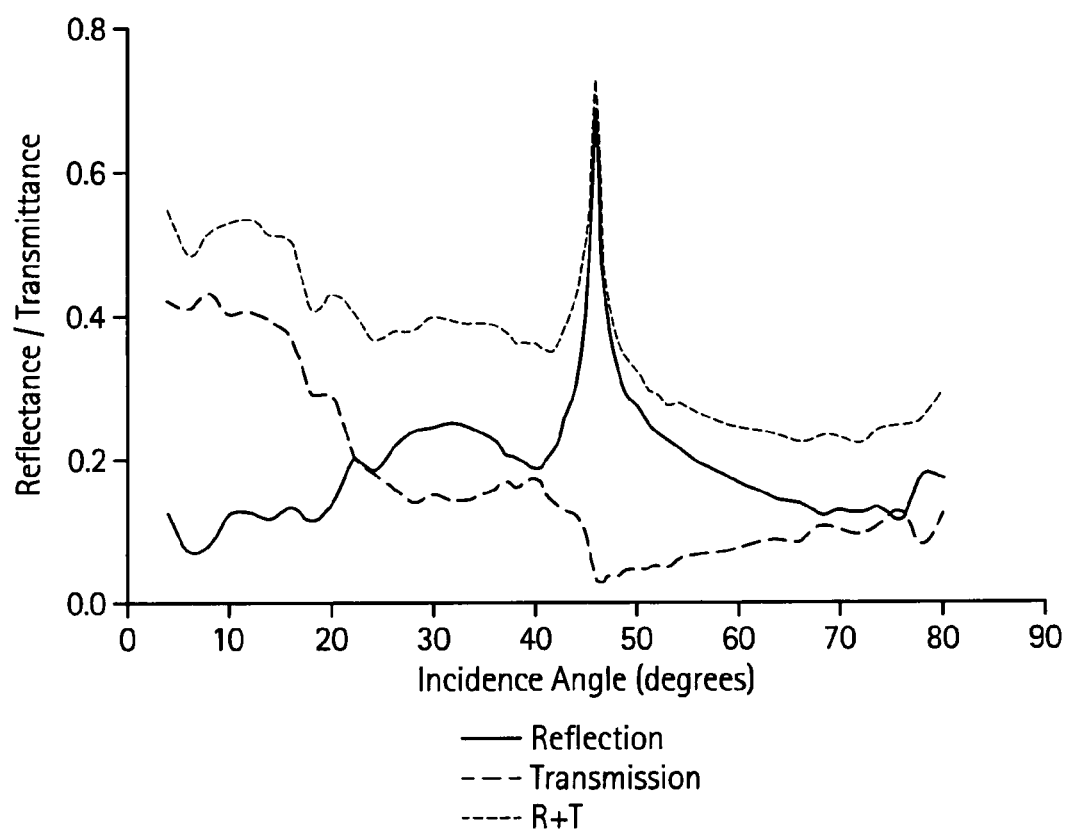
FIG. 20B is a graph of the transmission/reflectance spectra, of devices according to examples of the present invention.

The angular dependence of both transmission and reflection at a fixed wavelength (633 nm) using a He—Ne laser are shown in FIG. 20B. Transmission and reflection are measured as a function of incidence angle at 633 nm wavelength (TM polarized) for the 1D array sample with 120 nm thick Ag islands. The results shown in FIGS. 20A and 20B suggest that the three major transmission minima in FIG. 20A can be ascribed to the SP resonances that involve different sections of the metal surfaces. For a TM polarized light at this wavelength, the transmission spectra shows a minimum when the incidence angle is 45 degrees (the dashed curve in FIG. 20B). This angular position well matches the value (43 degrees) that is calculated from the condition for SP excitation at the plane that comprises the metal/substrate interfaces, i.e., $k_{sp}=k_o \sin\theta \pm mK_g$, where $k_o$ is the wave vector of an incident beam, $\theta$ is the incidence angle measured from the substrate normal, and $K_g$ is the grating vector. The reflection spectra (solid curve) shows a maximum with a sharp peak profile (with the full-width-half-maximum of 2-3 degrees) at the same incidence angle. The power loss, calculated as the difference between the incident power and the transmitted plus reflected power, is minimal at the SP resonance point. While it is possible that this result can be attributed to the diffraction-related Wood's anomaly, which occurs at close proximity to the SP resonance point, it is more likely that SP resonance plays a dominant role in this transmission/reflection anomaly.

Thus, without wishing to be bound by a particular theory, the present inventors believe that surface plasmon resonance is responsible for the observed transmission minima, involving two different modes of interaction with the metal island arrays: 1) the SP resonance along the planes that comprise either the metal/air or metal/substrate interfaces, and 2) the SP resonance localized along the surface (i.e., the metal island sidewalls) that encloses each metal island separated by slit shaped transparent regions. At these resonance points, little or no net-power flows along the metal surfaces and thus there is little or no funneling of incident power into a slit shaped transparent region. The incident power then strongly reflects back from the metal surface without incurring any major loss of power. For the case of relatively thin metal islands, the peak (i.e., passband) transmission through the array is believed to be due to that SP excitation is off-tuned from the resonance points such that a net power flow along the metal surfaces funnels into a slit region and then decouples into radiation modes which form a propagating transmitted beam. Thus, the resonance points of the SPs localized at metal islands can be tuned independent of the grating period by selecting metal island thickness and/or transparent region width, and may be used to tailor the transmission characteristics of the arrays, as described below.

The effect of the width 9 of the transparent regions 7 on the transmission characteristics of the radiation through the metal island array will now be described. The present inventors have determined that for band pass filters with high selectivity, the transparent region width should vary between about one and three times the penetration or skin depth of SP fields in the metal islands, when the incident radiation is directed onto the metal islands from an air/metal island interface.

The present inventors believe that a peak transmission corresponds to a situation where SP resonance is slightly off-tuned from that at the metal/substrate surface. The surface plasmons localized at each metal island are then expected to couple each other via a tunneling process as the transparent region width is reduced. The coupling between the surface plasmons in neighboring islands is expected to depend on the degree of overlap of the SP fields across a slit shaped transparent region, which is determined by the spatial extension of SP fields compared to the transparent region width (i.e., gap size).

The skin or penetration depth of SP fields is expressed as follows from H. Raether, *Surface Plasmons* (Springer-Verlag, New York, N.Y., 1988) page 6:

$$\frac{\lambda}{2\pi\sqrt{\varepsilon_d}}\sqrt{\frac{\varepsilon'_m + \varepsilon_d}{\varepsilon_d}} \text{ in } dieletric(\varepsilon_d)$$

$$\frac{\lambda}{2\pi\sqrt{\varepsilon'_m}}\sqrt{\frac{\varepsilon'_m + \varepsilon_d}{\varepsilon'_m}} \text{ in metal.}$$

Here, $\lambda$ is the free space wavelength of light, $\epsilon'_m$ is the real part of metal's dielectric constant and $\epsilon_d$ is the dielectric constant of the medium adjacent to the metal. The field strength decays by 1/e from the peak value at the surface. Thus, the penetration depth is dependent on both the wavelength and the materials through which the radiation is transmitted.

Once strong coupling occurs between metal islands, the metal islands become virtually connected (despite a gap) from the surface plasmon oscillation point of view. Propagation of SPs through the transparent region will eventually be blocked and the transmission spectra would show profiles similar to those of metal without a transparent region. It is thus expected that the metal island array would act as a narrow band pass filter by keeping the main (passband) transmission high while suppressing the long-wavelength transmission, when the transparent region width is within the range of about one to about three times the penetration depth of the SP fields in the metal islands.

The effect of the metal island thickness on the transmission characteristics of the radiation through the metal island array will now be described. The width of the main passband peak decreases with decreasing metal island thickness.

The main passband peak width is basically determined by the separation of the two transmission dips around the peak, i.e., the resonance wavelength of SP at the metal/dielectric interface and that of the SP localized at metal islands. Whereas the former wavelength is determined mostly by the grating period itself, the latter is governed by other mechanism, basically involving the periphery of cross-section of a metal island. While keeping the lateral dimension of the metal island close to the grating period (about a one to three skin depth length shorter than the grating period, in order to achieve good bandpass characteristics), the vertical dimension (i.e., thickness) of the metal island may be varied in order to adjust the total periphery. The change in thickness of the islands changes the resonance wavelength of the localized SPs and thus the passband width. Use of smaller thickness of metal islands thus reduces the passband width.

Figure 20C:
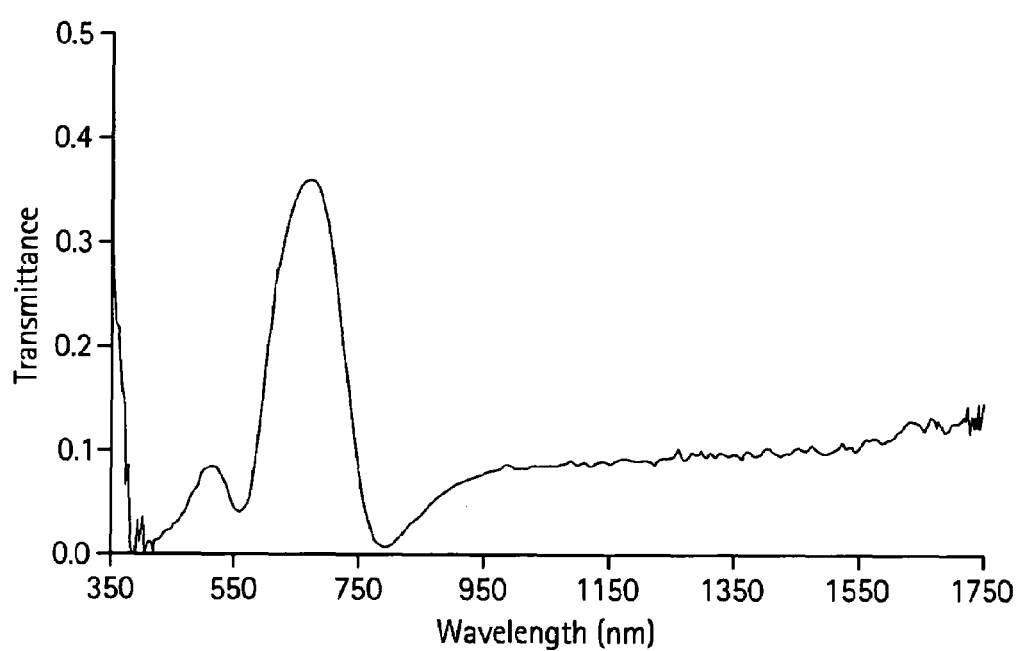

Examples of bandpass characteristics of the metal island array of this embodiment are illustrated in FIGS. 20A and 20C. FIG. 20C illustrates a transmission spectra of silver metal islands whose thickness is 180 nm (i.e., intermediate between those of the 120 and 200 nm thick Ag islands whose spectra are shown in FIG. 20A). The minimum transparent region width of this device is measured to be about 50 nm. In contrast, the minimum widths of the transparent regions of the devices having 200 nm and 120 nm thick islands are about 30 nm and 50-100 nm, respectively. In the devices of examples 1-3, the metal islands are deposited by angled deposition onto a ridged substrate. Thus, increased metal island thickness leads to a decreased transparent region width. However, for metal island arrays made by other methods, the width of the transparent regions does not necessarily decrease with increasing thickness of the metal islands.

As shown in FIG. 20C, peak transmission of over 70% (for TM polarization) is observed, even higher than that of the device having 120-nm thick islands, while maintaining the long-wavelength transmission low at around 20%. Thus, $(I_{longer-wavelength}/I_{main})<0.4$, preferably less than or equal to 0.3, where $I_{main}$ is the intensity of the main passband peak and $I_{longer\ wavelength}$ is the intensity of the transmitted radiation at longer wavelengths than the main passband peak. As shown in FIG. 20A, very high transmission (nearly the same level as the peak transmittance of the main passband at around 650 nm) in the long wavelength range (beyond 950 nm) is visible for the device with 120 nm thick islands and about 30 nm wide transparent regions. The transmission in the long wavelength regime, however, dramatically decreases (from 60% level to 10% transmission for TM polarization) for the device with 200 nm thick islands and 50-100 nm wide transparent regions. However, the peak (passband) transmission for this device also significantly decreased.

In the case of Ag/air interface at $\lambda=600$ nm, the penetration depth is calculated to be 390 nm in the air or 25 nm in metal. In the case of Au/air interface at $\lambda=600$ nm, the penetration depth is calculated to be 280 nm in the air and 30 nm in metal. FIGS. 20A and 20C illustrate that the preferred transparent region width is between 40 and 50 nm to achieve narrow band pass characteristics while maintaining high transmission of the main peak. In contrast, a device with a 30 nm wide transparent regions, showed narrow band pass characteristics, but a lower main peak transmission intensity. A device with up to 100 nm wide transparent regions did not exhibit narrow passband characteristics in view of the high intensity of the transmission at longer wavelengths.

Thus, the preferred range of minimum transparent region width (around 40-50 nm for desirable bandpass characteristics) that is provided in FIGS. 20A and 20C shows a close match to the penetration depth of SP fields in metal (or approximately $\frac{1}{10}$ of the air-side penetration depth). The preferred range of transparent region width for narrow bandpass filters is found to be approximately one to three penetration depths of SP fields in the metal side (or about $\frac{1}{10}$ to $\frac{3}{10}$ of the penetration depth in air).

The peak radiation transmission for unpolarized light is estimated to be up about to 50%, which is the theoretical maximum for the unpolarized light. This corresponds to near 100% transmission for a TM-polarized light. Taking into account the transparent region fill-factor, the transmission efficiency is greater than 100%, such as 100% to 500% through each transparent region. The upper bound may also be greater than 500% because it is determined by the inverse fill factor (i.e., period/slit width).

Figure 21:
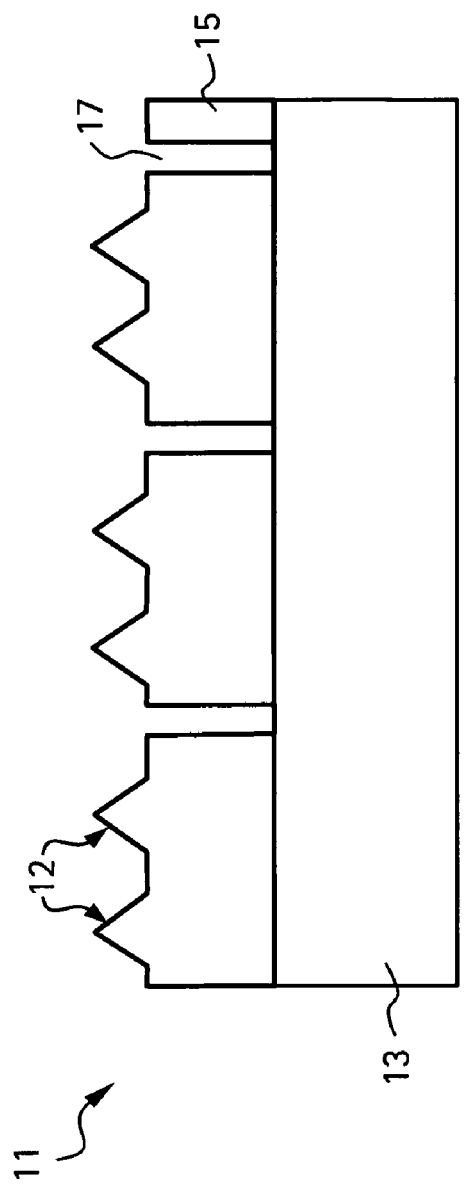
FIG. 21 is a schematic side cross sectional view of a device according to a preferred embodiment of the present invention.

In another preferred embodiment, the metal islands 15 of the optical device 11 are also located over a radiation transparent substrate 13. In one preferred aspect of this alternative embodiment, the metal islands 15 have a periodic surface topography 12 provided on at least one surface of the metal islands 15, as shown in FIG. 21. The topography 12 is configured such that it enhances the transmission of the radiation between the plurality of metal islands. The periodic topography 12 may comprise any metal features which provide strong coupling of the metal surface plasmons with incident radiation. For example, the topography may comprise any suitable raised and/or depressed regions on the surface of the metal islands 15 which are arranged in a regularly repeating (i.e., periodic) pattern, such as a two dimensional lattice. The raised regions may comprise cylindrical protrusions, semi-spherical protrusions, linear or curved ribs, rectangular ribs, raised rings and/or raised spirals. The depressed regions may comprise cylindrical depressions, semi-spherical depressions, linear or curved troughs, rectangular troughs, ring shaped troughs and/or spiral shaped troughs. The width or diameter of the raised or depressed regions is preferably less than the period of these features, and the product of this period with the refractive index of the substrate should be less than the maximum desired transmitted wavelength of the radiation.

In another preferred aspect of this embodiment, the surface topography 12 comprises a topography comprising a material other than metal which includes surface plasmon coupling into the metal. In one example, the refractive index of the dielectric layer or ambient medium adjacent to the metal surface is periodically or quasi-periodically modulated, without topographic modulation of the metal surface (i.e., without corrugation/indentation on the metal surface). For example, periodic arrangement of dielectric layer or layers formed on a flat or corrugated metal surface can induce the surface plasmon coupling into metal. Thus, element 12 in FIG. 21 may refer to periodically or quasi-periodically arranged dielectric material features formed on a flat metal island 15 surface. Alternatively, a flat or textured dielectric layer or layers with a variable refractive index may be used for plasmon coupling. A variable refractive index in a flat dielectric layer or layers may be achieved by periodically or quasi-periodically modulating the composition of the layer or layers along their width on the metal islands. Any suitable dielectric material many be used, such as silica, quartz, alumnia, silicon nitride, polymer material, etc. Dielectric modulation (instead of or in addition to metal surface corrugation) may be used in wavelength tunable structures. The non-metal topography may also be used on metal films having one or more apertures.

In this embodiment, the transparent regions 17 are separated by a period $a_o$ which is much larger than the period of the previous embodiment, such that the period of the transparent regions 17 does not substantially contribute to the enhancement of the transmission of the radiation. Thus, the width of the metal islands 15 of this embodiment is much greater than the width of the islands 5 of the previous embodiment. For example, the period $a_o$ and thus the approximate width of the islands 15 is preferably equal to the effective propagation distance of the SPs, such as 5 microns or greater, preferably about 5-10 microns for Ag islands being irradiated with visible light.

As shown in FIG. 21, the transparent regions 17 are slit shaped. These slits have a length that is significantly larger than their width. Preferably, the length is at least ten times larger than the width. However, the transparent regions 17 may have any other suitable shape instead of a slit shape which results in plasmon enhanced transmission of radiation.

Figure 22:
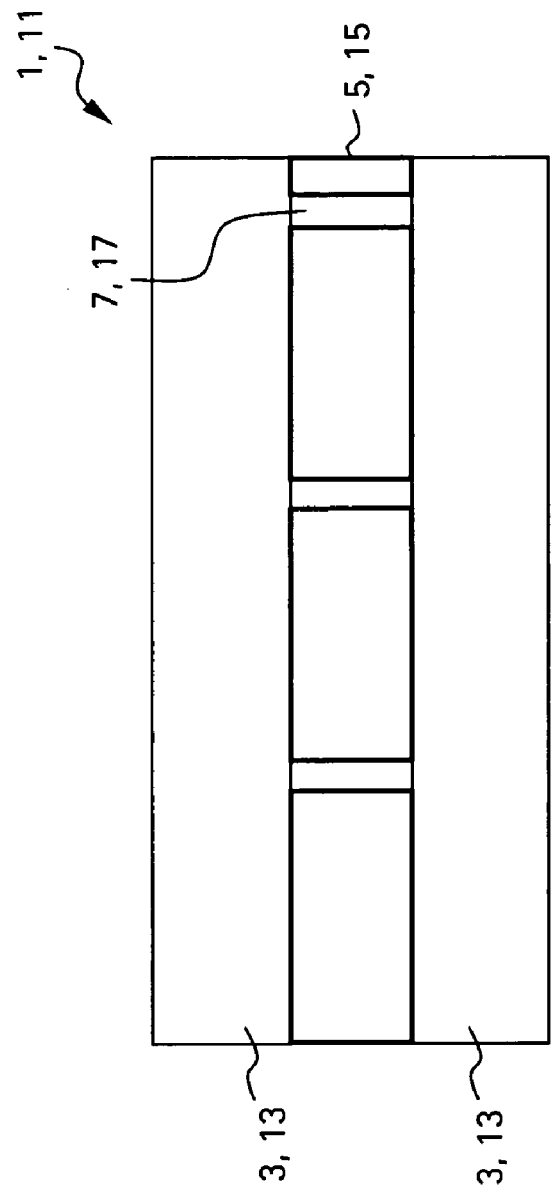
FIG. 22 is a schematic side cross sectional view of a device according to the preferred embodiments of the present invention.

In the devices 1, 11, a symmetric configuration may be used to reduce a passband width (i.e., to reduce the number of sidelobes or sidebands) if desired. In this configuration, a second substrate composed of the same dielectric media as the first substrate 3, 13 is attached over the top of the metal islands 5, 15, such that the metal islands 5, 15 have interfaces with the same dielectric media on both sides, as illustrated in FIG. 22.

As discussed above, the metal islands 5, 15 may comprise discrete metal islands that are not connected to each other (i.e., the metal islands are not in direct contact with each other) or metal islands that are connected to each other at a peripheral region of the optical device. For example, as shown in FIG. 23, the metal islands 5, 15 are discrete metal islands. In contrast, as shown in FIG. 24, the metal islands 5, 15, are connected to each other at the periphery of the devices 1, 11.

Figure 15:
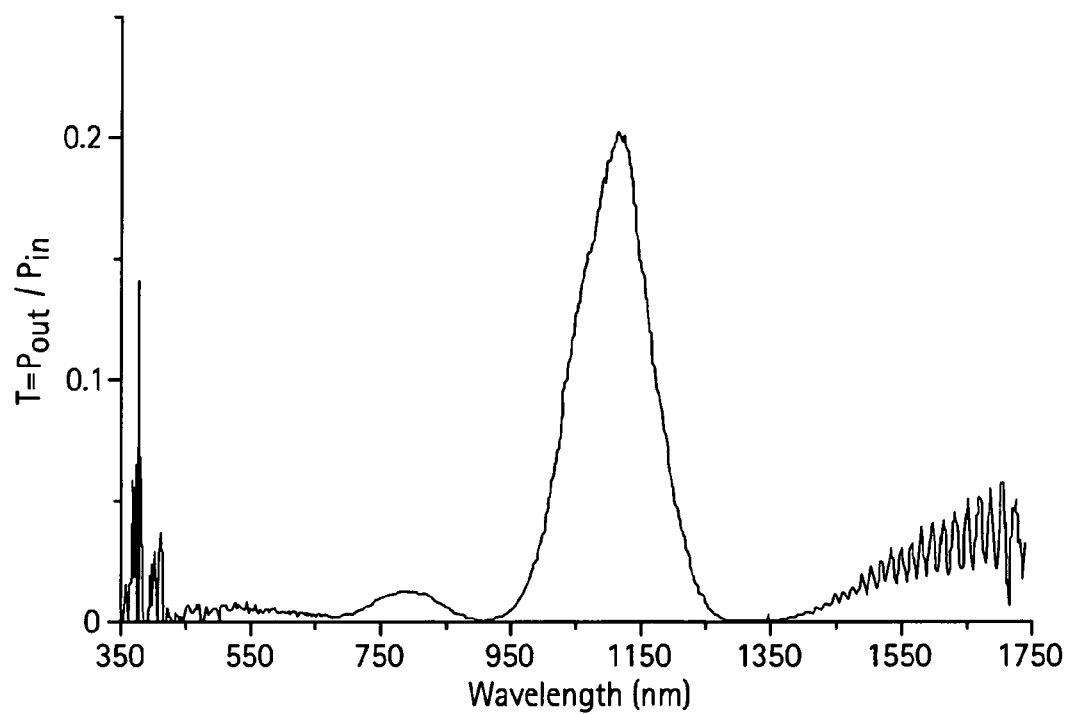
FIGS. 15 and 18 are plots of transmission spectra through devices of a preferred embodiment of the present invention.

The transmission spectra through the transparent regions in the three dimensional Ag metal island array of FIG. 14 is shown in FIG. 15. The vertical axis corresponds to the transmission ratio, $P_{out}/P_{in}$. The measurement result shown in FIG. 15 confirms that the side peaks are well suppressed. The main peak is also narrowed from 170 nm to 140 nm in FWHM value. The three dimensional structures are not limited to just two layers and may have any suitable number of layers greater than two and various different layer patterns and interlayer spacing.

If desired, the optical devices described herein may include an integrated radiation source, such as a laser, LED or lamp adapted to emit the incident radiation and/or an integrated radiation detector, such as a charge coupled device (CCD) array or CMOS active pixel array, adapted to detect the radiation transmitted through the substrate and between the plurality of metal islands. Alternatively, a separate radiation source and/or the radiation detector may be used with the devices.

The optical devices may be used for any suitable application. Thus, the devices may be used as a nano-optic filter with a narrow passband width or as a polarizer. The devices may also be used for wavelength separation of incident radiation. The devices may be used for other applications, such as a light collector, collimator or coupler for an optical fiber, a light selection device in near field optical scanning microscope, and a photolithography mask.

SPECIFIC EXAMPLES

The following specific examples illustrate preferred embodiments of the present invention and should not be considered limiting on the scope of the invention.

Figure 16A:
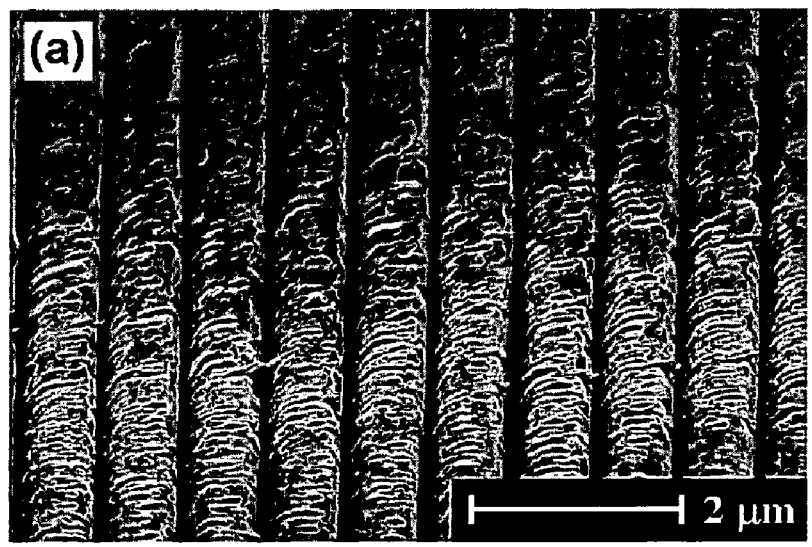
FIGS. 16A, 16B, 16C and 17 are micrographs of devices according to an embodiment of the present invention.
Figure 16B:
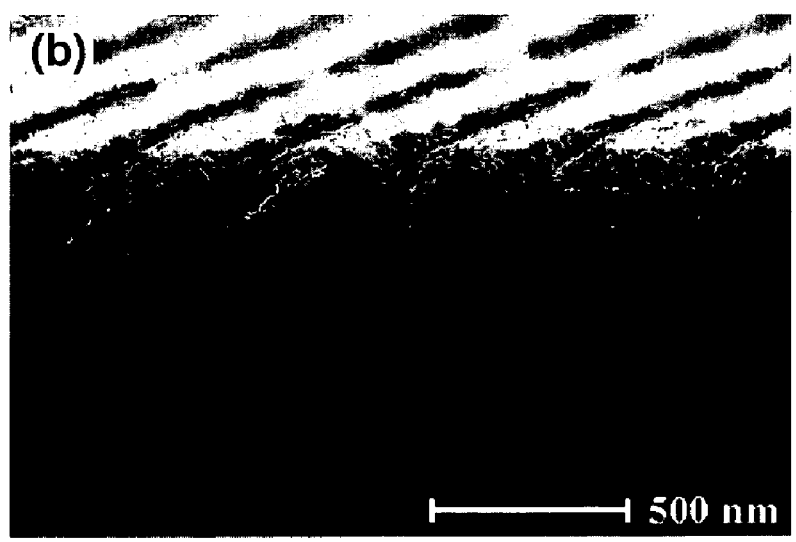
Figure 16C:
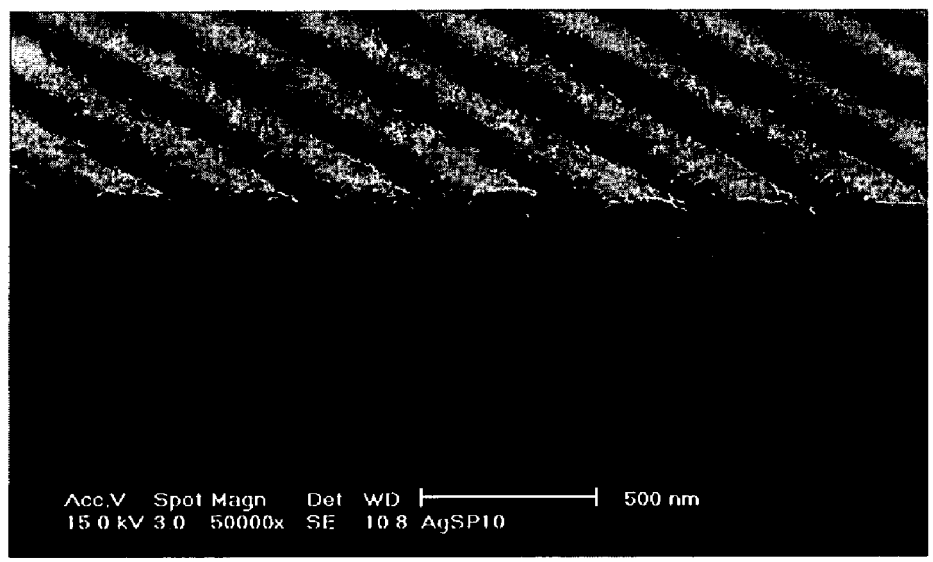

The devices of examples 1, 2 and 3 are made by the same process, except that the metal island thickness is 200 nm in example 1, 120 nm in example 2 and 180 nm in example 3. Since the metal islands are deposited by angled deposition, the width of the transparent regions increased with decreasing metal island thickness. Thus, the minimum width of the transparent regions in example 1 is about 50 to 100 nm (the width varies due to the slight non-uniformity of the metal islands), the minimum width of the transparent regions in example 2 is about 30 nm and the minimum width of the transparent regions in example 3 is about 50 nm. The transmission spectra of the devices of examples 1 and 2 with 120 and 200 nm thick metal islands, respectively, are shown in FIG. 20A and the transmission spectra of the device of example 3 with 180 nm islands is shown in FIG. 20C. FIGS. 16A, 16B and 16C illustrate SEM micrographs of metal island arrays with metal island thicknesses similar to those of examples 1-3. The thickness of metal islands in FIG. 16A is 400 nm, in FIG. 16B, 250 nm and in FIG. 16C 180 nm. The devices of examples 1, 2 and 3 are made by the method illustrated in FIGS. 9D-9I.

Figure 17:
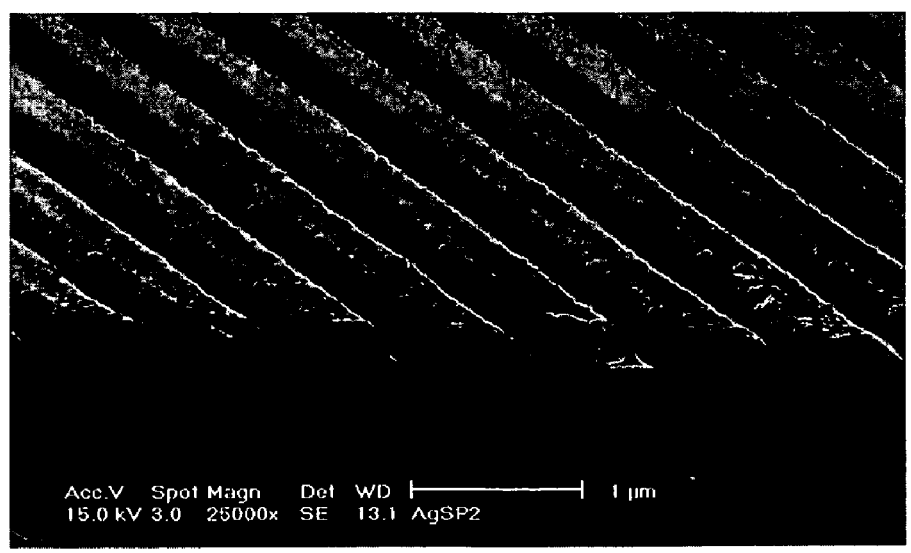

FIG. 17 shows a micrograph of a one dimensional (1D) silver metal island array device of Example 4 with narrow slit shaped transparent regions. The device is formed by depositing a 200-nm-thick Ag on a 1D-grating-etched quartz substrate. The grating pattern is generated with a holographic process and the grating period is designed to be 750 nm. The slit width is measured to be around 150 nm at the narrowest part. This corresponds to about a 20% ratio of the transparent region/metal island surface area for normal incident waves.

Figure 18:
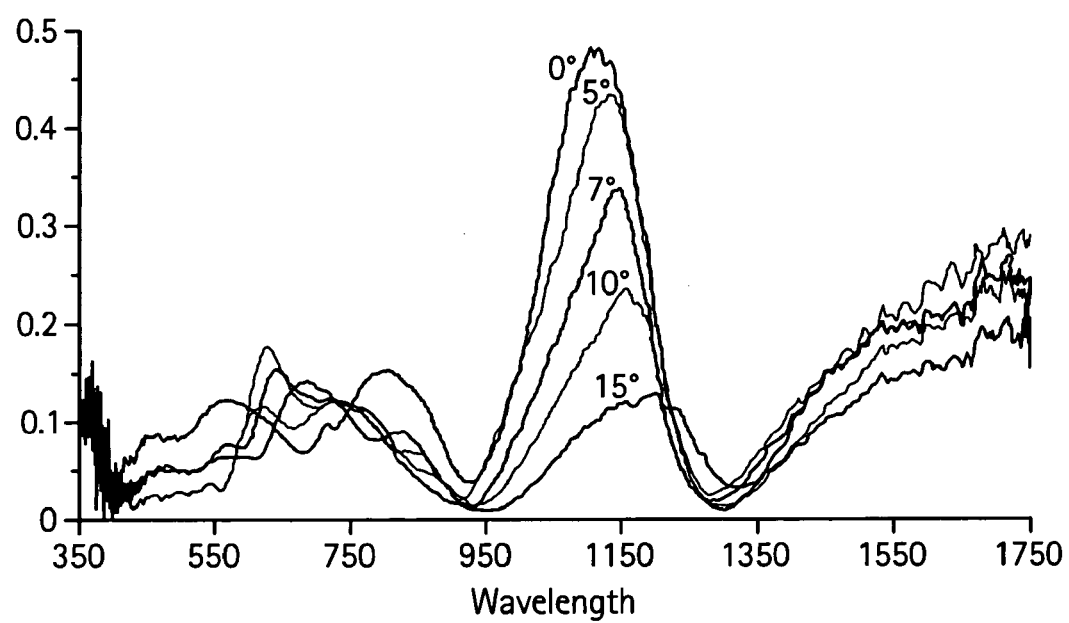

FIG. 18 illustrates transmission spectra through the transparent regions in the Ag metal island array. The vertical axis corresponds to the transmission ratio, $P_{out}/P_{in}$ for unpolarized light. For TM polarization, the peak transmission is over 90%. The dependence of the transmission spectra on the incidence angle of incident radiation is also shown in FIG. 18. As the incidence angle is varied, the transmission peaks shift and split. The main passband peak shows a full-width-half-maximum value of about 170 nm. A much narrower passband width of about 10 nm to about 160 nm and well suppressed transmission at long wavelength is possible with a different transparent region design and improved uniformity, and with an optimized metal island thickness and slit width, using a numerical analysis of transmission spectra based on a transfer matrix and a quasi-analytical model.

Figure 25:
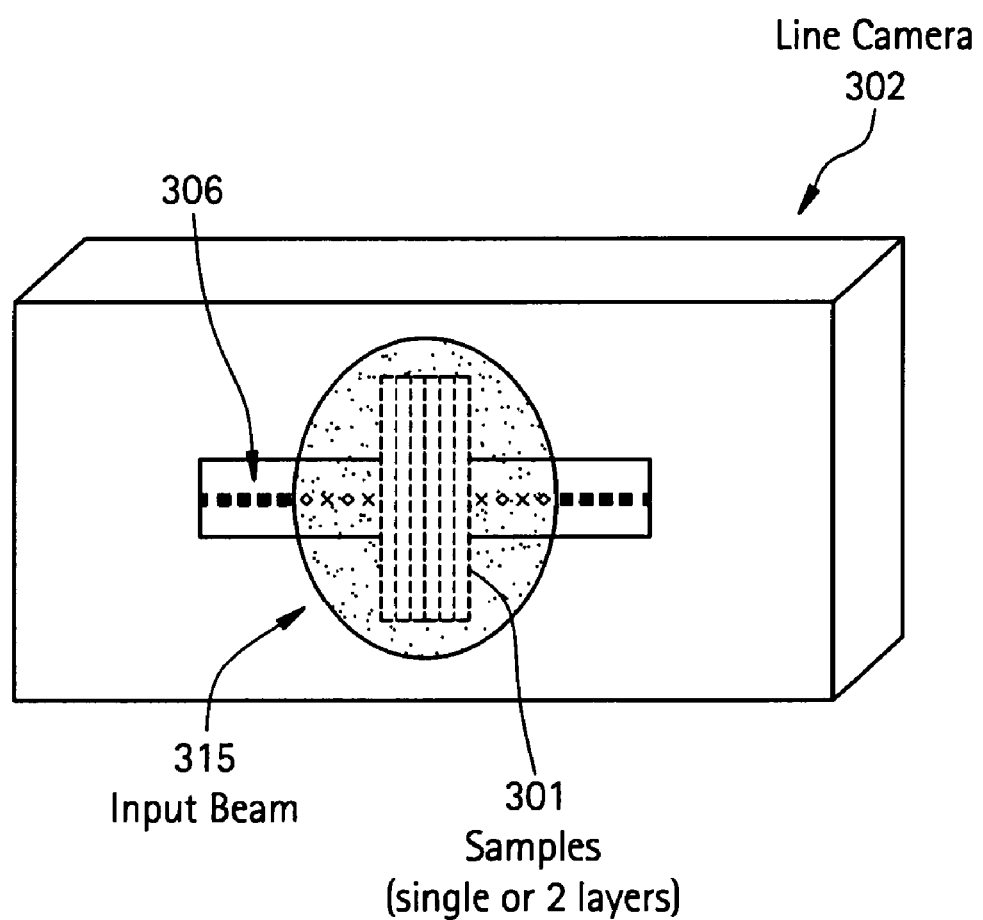
FIG. 25 is a schematic top view of an experimental set up for examples 5-12.

FIG. 25 illustrates a top view of the experimental set up for examples 5-12. As shown in FIG. 25, a single or double layer wavelength separation device 301 comprising metal islands or a metal film containing a plurality of openings is positioned over a line camera 302 containing a plurality of pixels 306. The incident or input light beam 315 area is larger than that of the wavelength separation device 301, such that some of the incident light 315 is detected by pixels 306 of the camera 302 without passing through the wavelength separation device.

Figure 26:
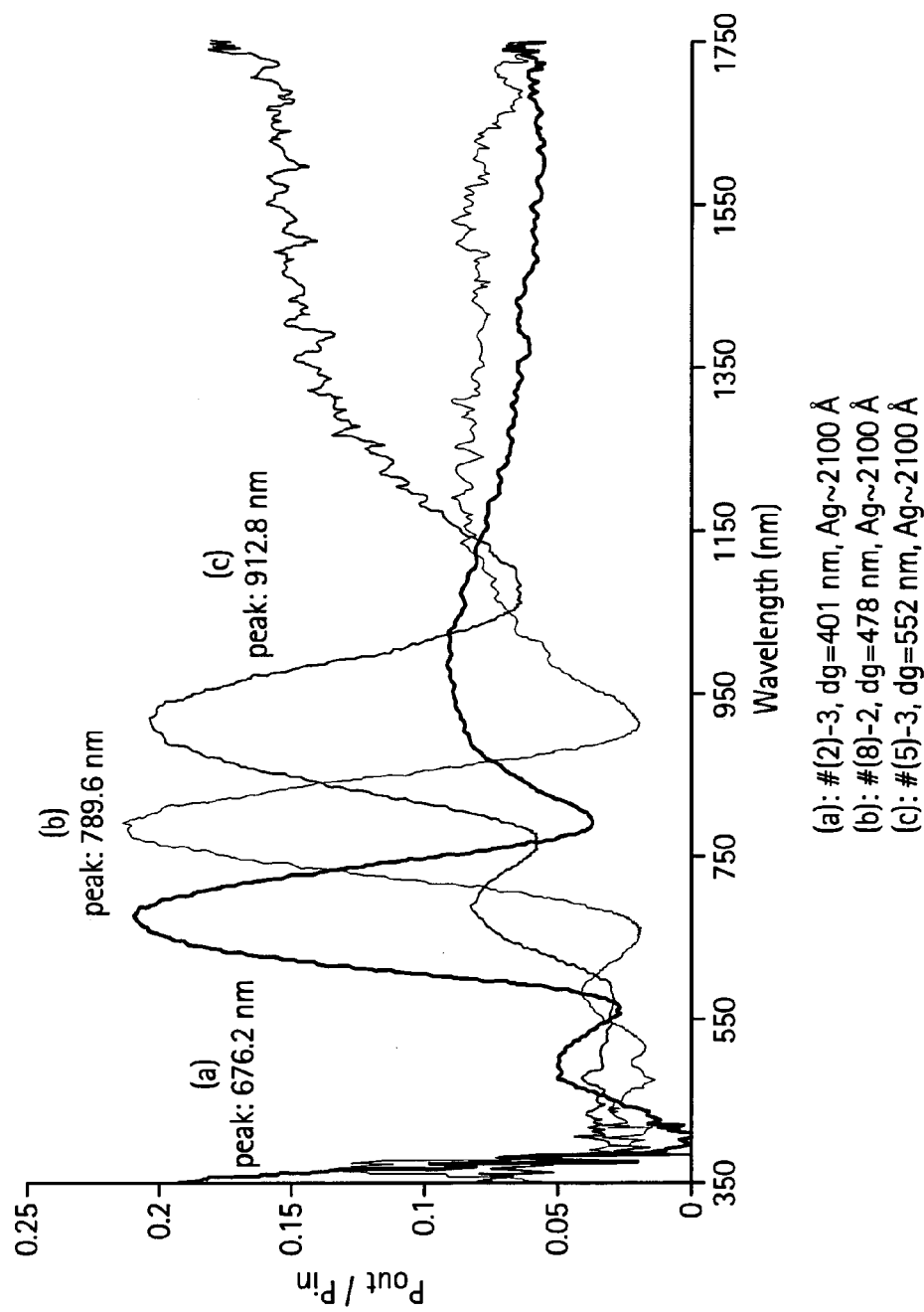
FIG. 26 is a plot of transmission spectra for examples 5, 6 and 7.

FIG. 26 illustrates the transmission spectra for examples 5, 6 and 7. FIG. 26 is a plot of the ratio of the transmitted to incident radiation versus wavelength of the radiation. In example 5, white light was transmitted through a metal island array having about 2100 Angstrom thick silver islands. The openings between the islands have a grating period ($d_g$) of about 401 nm. The grating period is also referred to herein as the period of the transparent regions, $a_o$. As shown by peak (a) on the left of FIG. 26, the transmitted radiation through this array has a peak wavelength of about 676.2 nm. In example 6, white light was transmitted through a metal island array having about 2100 Angstrom thick silver islands. The openings between the islands have a grating period ($d_g$) of about 478 nm. As shown by peak (b) in the middle of FIG. 26, the transmitted radiation through this array has a peak wavelength of about 789.6 nm. In example 7, white light was transmitted through a metal island array having about 2100 Angstrom thick silver islands. The openings between the islands have a grating period ($d_g$) of about 552 nm. As shown by peak (c) on the right of FIG. 26, the transmitted radiation through this array has a peak wavelength of about 912.8 nm. Thus, as illustrated in FIG. 26, radiation of a different peak wavelength is transmitted through the array depending on the grating period of the openings in the array.

Figure 27:
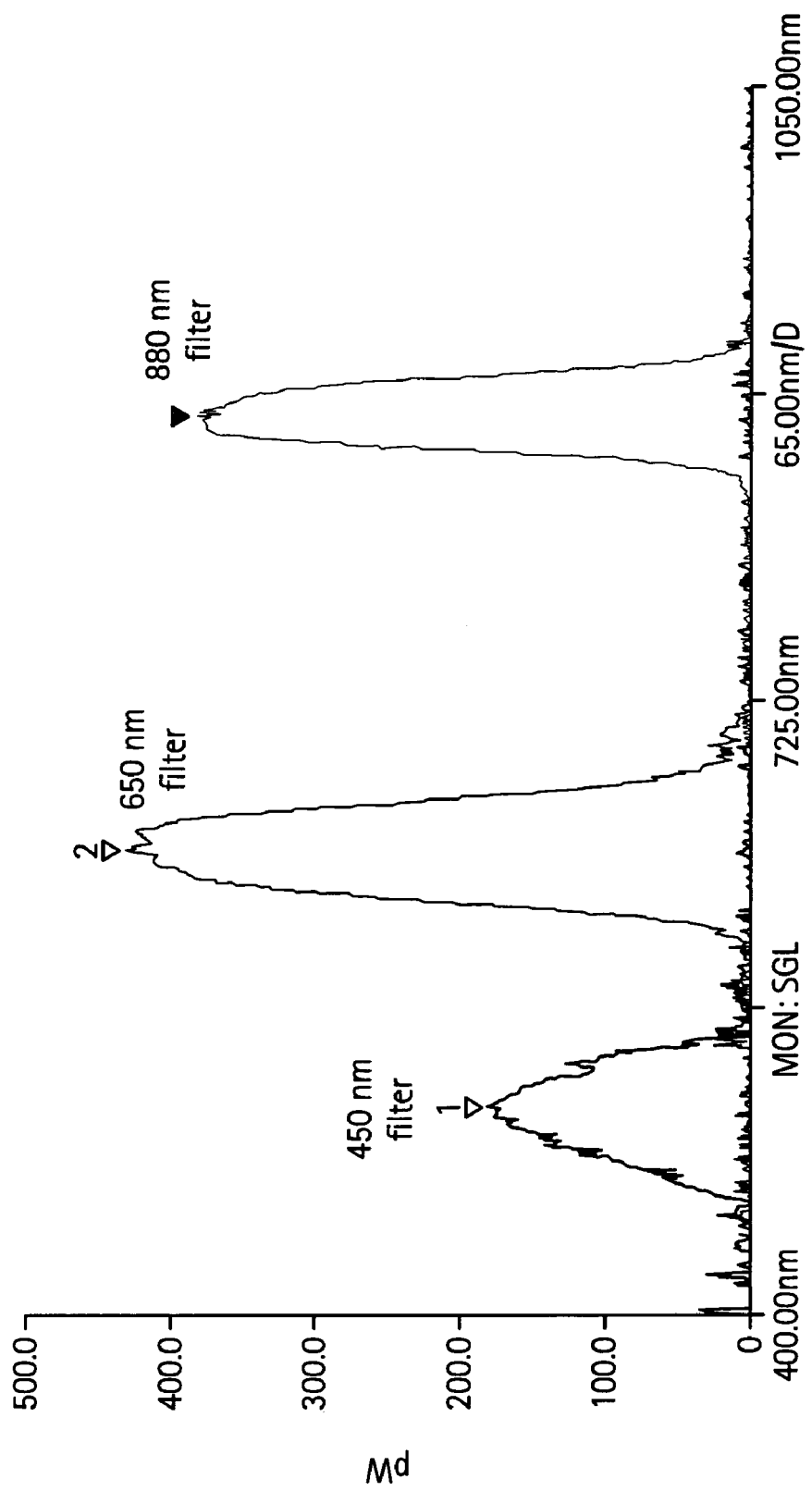
FIG. 27 is a plot of transmission spectra for three prior art filters.
Figure 28:
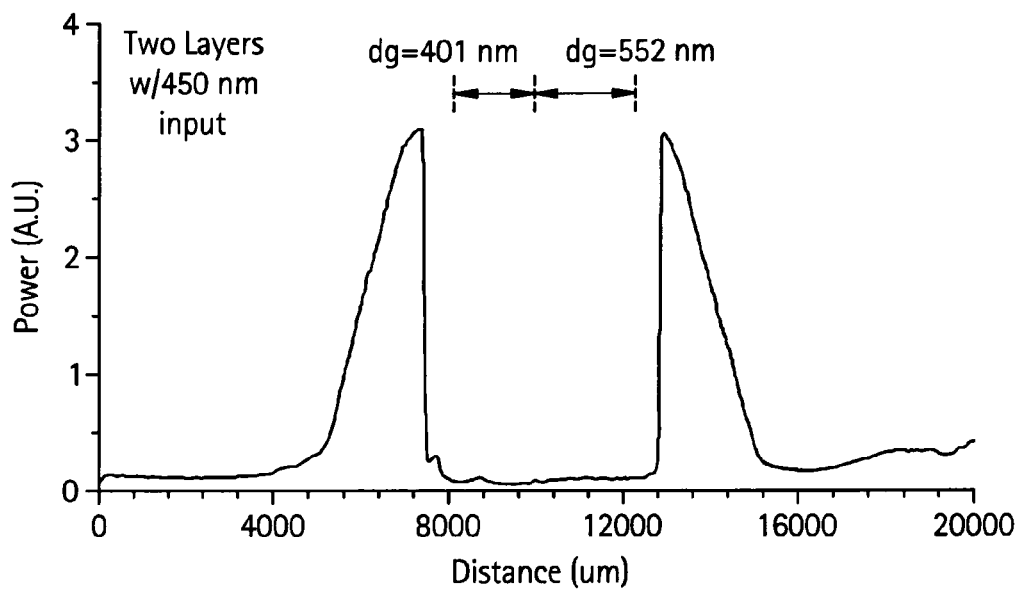
FIGS. 28, 29 and 30 are plots of transmission versus location on the detector for examples 8, 9 and 10 respectively.

FIG. 27 illustrates a transmission spectra for white light passed through prior art 450 nm, 650 nm and 880 nm filters. FIG. 28 illustrates the results of example 8. In example 8, the wavelength separation device of example 5 was placed next to the wavelength separation device of example 7. In other words, the metal island array having grating period ($d_g$) of about 401 nm is placed at a first arbitrary location on the camera 302 (i.e., at a location between 8000 and 10,000 microns from a reference point), while the metal island array having grating period ($d_g$) of about 552 nm is placed at a second arbitrary location on the camera 302 (i.e., at a location between 10,000 and 12,000 microns from a reference point). White light is then passed through the 450 nm prior art filter illustrated in FIG. 27 and then through the arrays of examples 5 and 7. The transmitted light is then detected by the camera 302. As shown in FIG. 28, the large peaks at about 7,000 and about 13,000 microns corresponds to the light which was not transmitted through the arrays. Furthermore, as shown in FIG. 28, the arrays of examples 5 and 7 were effective in filtering 450 nm peak wavelength light. This is to be expected because the peak transmission of the arrays of examples 5 and 7 is 676.2 nm and 912.8 nm, respectively.

Figure 29:
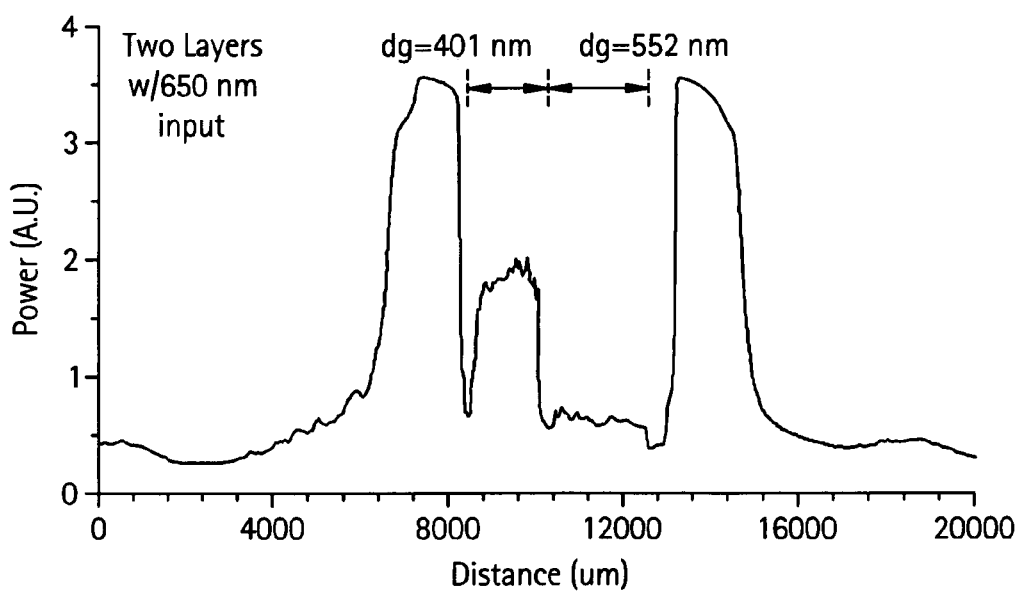

FIG. 29 illustrates the results of example 9. The conditions of example 9 are identical to those of example 8, except that white light was passed through the 650 nm prior art filter of FIG. 27 rather than the 450 nm prior art filter. As shown in FIG. 29, the array example 7 was effective in filtering 650 nm peak wavelength light because the peak transmission of this array is 912.8 nm. In contrast, the array of example 5 transmitted a portion of the 650 nm light because the peak transmission of this array is 676.2 nm.

Figure 30:
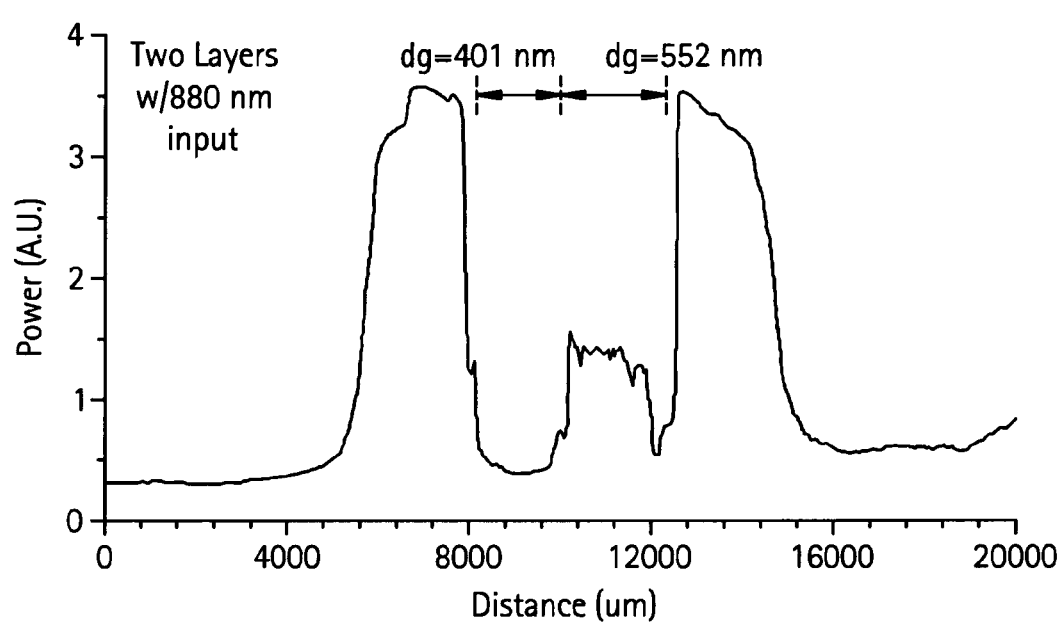

FIG. 30 illustrates the results of example 10. The conditions of example 10 are identical to those of example 8, except that white light was passed through the 880 nm prior art filter of FIG. 27 rather than the 450 nm prior art filter. As shown in FIG. 30, the array example 5 was effective in filtering 880 nm peak wavelength light because the peak transmission of this array is 676.2 nm. In contrast, the array of example 7 transmitted a portion of the 880 nm light because the peak transmission of this array is 912.8 nm.

Figure 32A:
FIGS. 31A and 32A are schematic top views of wavelength separation devices according to embodiments of the present invention.
Figure 32B:
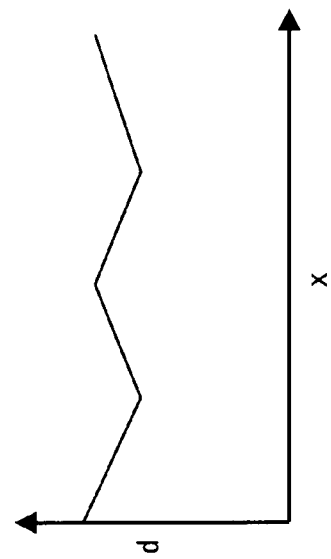
FIG. 32B is a schematic plot of grating period versus location on the detector for the device of FIG. 32A.
Figure 31A:
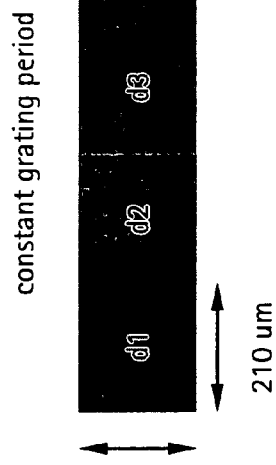
Figure 31B:
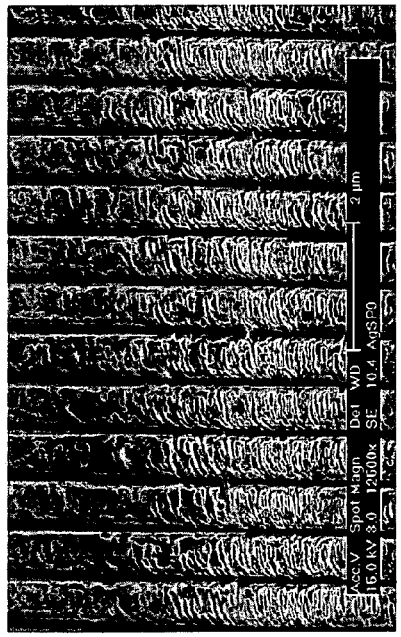
FIG. 31B is a micrograph of the device of FIG. 31A.

As discussed above, the wavelength separation devices 101, 301 may have a constant grating period ($d_g$) in each cell or a chirped grating period along the length of the device. FIG. 31A illustrates an example of a wavelength separation device where each cell contains a different grating period d1, d2, d3 and d4. FIG. 31B is a micrograph of such a device. FIG. 32A illustrates an example of a wavelength separation device where the grating period is chirped. FIG. 32B illustrates an exemplary plot of grating period versus location (x) on the wavelength separation device.

Figure 33A:
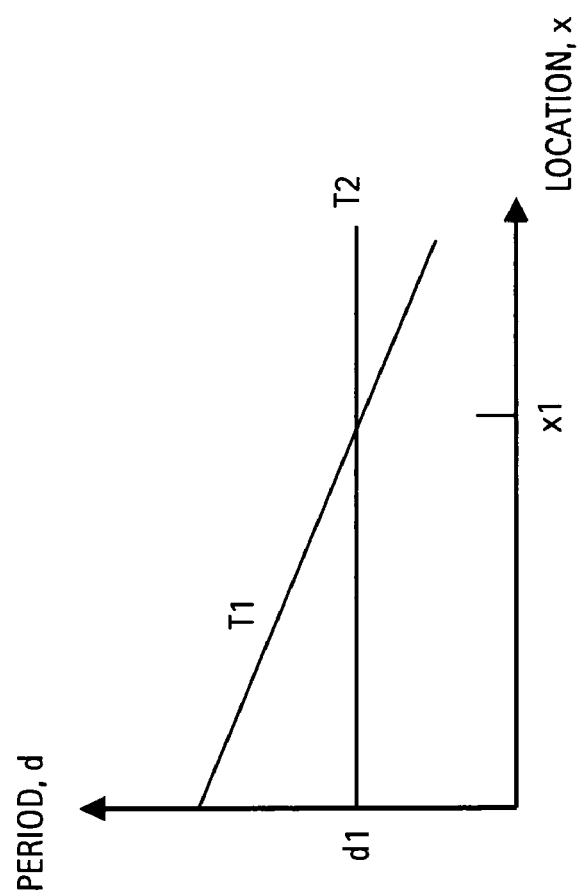
FIG. 33A is a schematic illustration of the device of example 11.
Figure 33B:
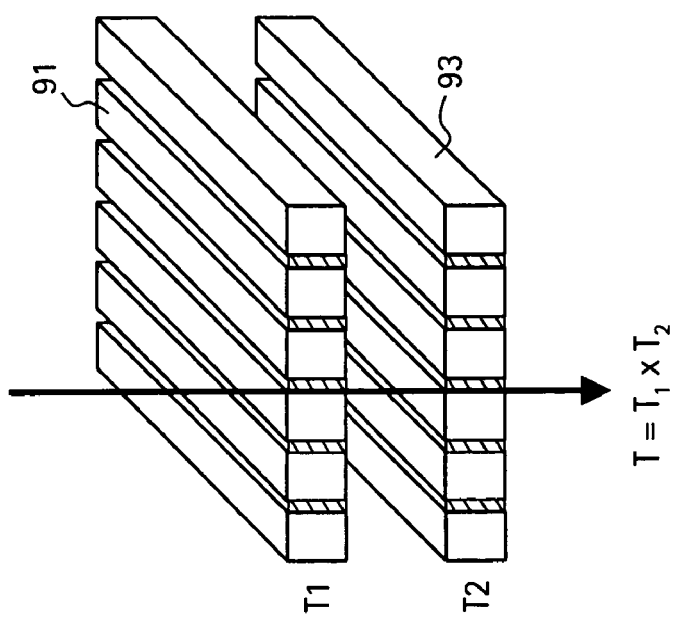
FIG. 33B is a schematic plot of grating period versus location on the detector for the device of FIG. 33A.
Figure 34A:
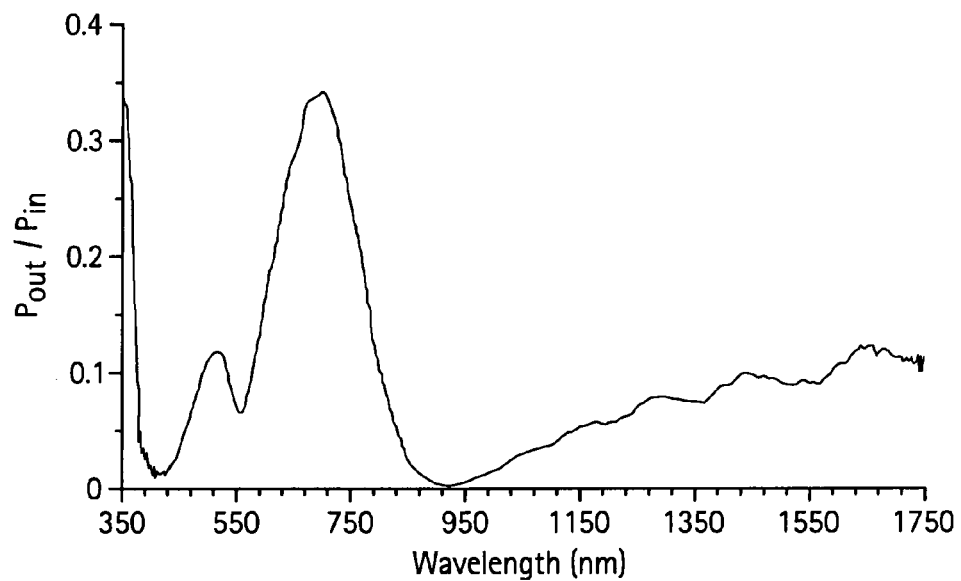
FIGS. 34A, 34B and 34C are plots of transmission spectra for the device of example 11.
Figure 34B:
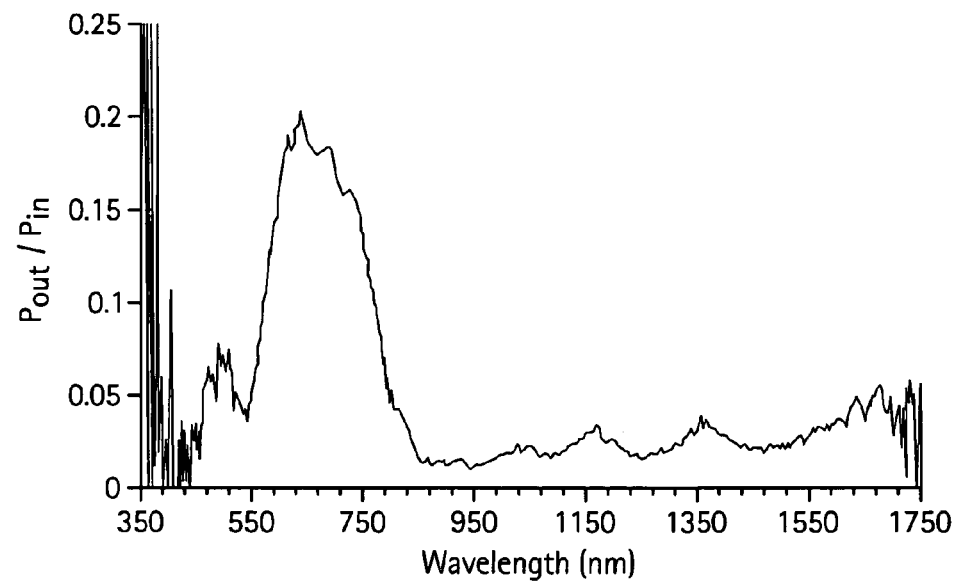
Figure 34C:
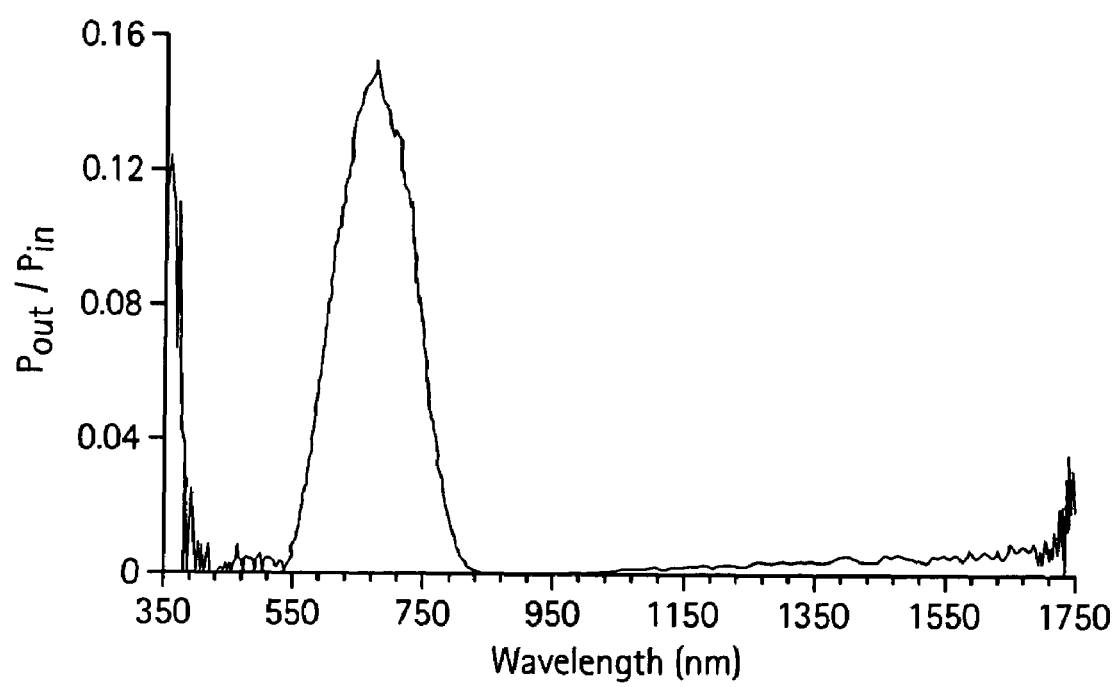

FIG. 33A schematically illustrates example 11 having a two layer wavelength separation device. The device contains an array with a chirped grating period 91 which is stacked over an array with a constant grating period 93. Is should be noted that array 93 may be stacked over array 91 instead if desired. Any suitable grating periods may be selected. Preferably, the chirped grating period of array 91 overlaps a constant grating period d1 of array 93 in at least one location, x1, of the wavelength separation device. This is shown in FIG. 33B, which is a plot of grating period versus location on the device, x. One of the detector pixels 306 is positioned at location x1 in the camera 302. The total transmittance, T, of white light through both arrays 91 and 93 (shown in FIG. 34C) is a product of transmittance T1 through the first array 91 (shown in FIG. 34B) and the transmittance T2 through the second array 93 (shown in FIG. 34A). As can be seen from FIGS. 34A-C, the radiation transmitted through both arrays (i.e., T) has a narrower peak width than the radiation transmitted through each of the arrays 91, 93 alone (i.e., T1 or T2). Thus, stacking two arrays reduces a peak width of the transmitted radiation as well as reduces the intensity of the sidebands or side peaks relative to the intensity of the main peak.

FIG. 35A schematically illustrates example 12 wherein two arrays 91, 93 having a chirped grating period are stacked over each other. The detector pixels 306 are located along different locations on the camera 302. Thus, each pixel 306 window (a 7 micron window for example) captures radiation of a different peak wavelength that passed through a different portion of the wavelength separation device that has a different grating period of the chirped grating period. For example, FIG. 35A illustrates the case where the arrays 91 and 93 have the same chirped grating period. The arrays 91, 93 may be stacked such that the transparent regions in each array are aligned with the transparent regions in the adjacent array or the arrays 91, 93 may be stacked such that transparent regions in one array are offset by a predetermined amount from the transparent regions in the other array in the horizontal (i.e., x) direction along the direction of the pixels 306. FIG. 35B illustrates transmittance spectra for various arrangements of chirped arrays. The peak labeled "No offset" corresponds to transmittance of white light through both arrays 91, 93 at a predetermined location over the detector (x=290 microns) where there is no offset between transparent regions of the chirped arrays 91, 93. The grating period of the arrays is 340 nm at this location (x=290 microns). The peak labeled "40 micron offset" corresponds to transmittance of white light through both arrays 91, 93 at a predetermined location over the detector (x=330 microns) where there is a 40 micron offset between transparent regions of the chirped arrays 91, 93. The grating period is 400 nm at this location. As can be seen from these two peaks, by introducing the offset between the arrays, the peak width is narrowed, but the overall peak intensity is decreased.

FIG. 36A illustrates a transmission spectra of a single-layer wavelength-separation device of example 13 having a chirped grating period along the length of the device (see FIG. 32A). The device is 800 micron wide (along the length direction) and comprises nine cells or filters. Each filter is 98 microns wide and has a different (but constant) grating period, linearly chirped from 390 nm to 630 nm with 30 nm step between neighboring cells. The transmission spectra measured at each cell show a progressive and linear shift of the main passband position from around 750 nm to around 1100 nm. The peaks listed in the legend of FIG. 36A are shown in the Figure from right to left (i.e., the dg=630 nm "black" peak is the right most peak and the dg=390 nm "violet" peak is the left most peak).

FIG. 36B illustrates a transmission spectra of a two layer stacked wavelength separation device of example 14 comprising two pieces of the same device shown in FIG. 36A. Enhancement of bandpass characteristics of the stacked configuration is clearly observed. FIG. 36 illustrates a suppression of lower intensity side peaks at the shorter wavelength region, reduced transmission in the longer wavelength region, and reduction of the main passband width from about 150-200 nm to about 100-150 nm compared to FIG. 36A. Further refinement of bandpass characteristics, especially suppression of long wavelength transmission is expected by optimum control of metal thickness and thus the metal slit width. In the example shown in FIG. 36A, the mesa-etched quartz substrate is designed to have a slit width of 120 nm. After angled deposition of a 150 nm thick Ag layer, the slit width is reduced to 50-80 nm. Control of metal thickness can adjust the slit width.

Figure 36C:
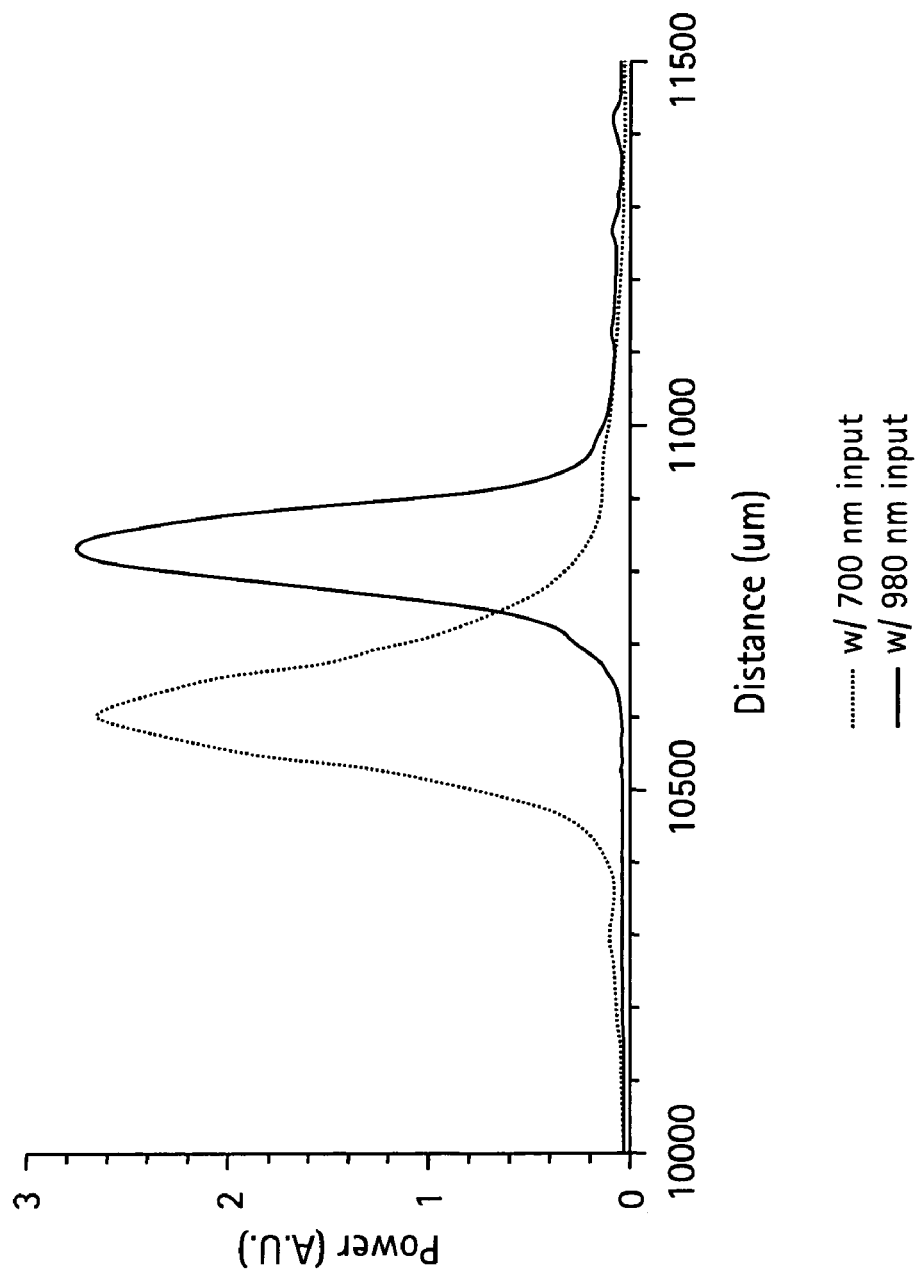
FIG. 36C is a plot of transmission power versus location the detector for the device of example 15.

FIG. 36C illustrates wavelength separation with a two layer stacked device of example 15, as measured with a linear array CCD detector (see FIG. 25 for experimental configuration). The wavelength separation device is a 390 micron wide array comprising 28 cells (filters) with each cell having a 14 micron width. The grating period is chirped from 360 nm to 630 nm with a 10 nm step along the array direction. A 980 nm wavelength light is incident to a wavelength separation device (two layer stacked). The light is registered at pixels at around 10850 micron location of a CCD array. When a 700 nm light is incident to the same device, the light is registered at 10600 micron location of the CCD array. This spatial separation on CCD matches the spectral separation of the two input lights. In other words, the different wavelength of light is detected by a different portion of the CCD array which is located under the portion of the wavelength separation device designed to transmit light of that particular wavelength.

Various embodiments and preferred aspects of the present invention have been separately described above. However, each step or feature from one preferred embodiment or aspect may be used in another embodiment or aspect, in any appropriate way.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

The invention claimed is:

1. A device comprising:
a Fabry-Perot cavity filter comprising a first mirror and a second mirror, wherein a gap between the first and the second mirror monotonically varies as a function of width of the filter; and
a channel selection filter comprising a metal nanooptic filter array based on plasmon resonance,
wherein the channel selection filter has a wider wavelength passband width than the Fabry-Perot cavity filter and
wherein the metal nanooptic filter array comprises a plurality of subwavelength apertures in a metal film or between metal islands, such that a distance between the apertures in different regions of the metal nanooptic filter array is different.

2. The device of claim 1, wherein the first mirror is tilted with respect to the second mirror such that the gap varies in a continuous fashion along the width of the filter.

3. The device of claim 1, wherein the first mirror and the second mirror comprise flat mirrors.

4. The device of claim 1, wherein:
the gap comprises an air filled gap; and
the first mirror is tilted with respect to the second mirror such that the gap between the first and the second mirror monotonically varies.

5. The device of claim 1, wherein:
a tapered spacer material is located in the gap; and
the first and the second mirrors contact the tapered spacer material such that the gap between the first and the second mirror monotonically varies.

6. The device of claim 1, further comprising a photodetector, wherein a first photodetector pixel is adapted to detect radiation from the Fabry-Perot cavity filter position having a first gap height and a second photodetector pixel is adapted to detect radiation from the Fabry-Perot cavity filter position having a second gap height different from the first gap height.

7. A device, comprising:
a Fabry-Perot cavity filter comprising a first mirror and a second mirror wherein a gap between the first and the second mirror is variable; and
a photodetector array, wherein a first photodetector pixel is adapted to detect radiation from the Fabry-Perot cavity filter position having a first gap height and a second photodetector pixel is adapted to detect radiation from the Fabry-Perot cavity filter position having a second gap height different from the first gap height;
a channel selection filter array positioned such that only one peak from the Fabry-Perot cavity filter is incident on each pixel of the photodetector array;
wherein the channel selection filter comprises a metal nanooptic filter array based on plasmon resonance;
wherein the channel selection filter has a wider wavelength passband width than the Fabry-Perot cavity filter; and
wherein the metal nanooptic filter array comprises a plurality of subwavelength apertures in a metal film or between metal islands, such that a distance between the apertures in different regions of the metal nanooptic filter array is different.

8. The device of claim 7, wherein:
the photodetector array comprises a plurality of pixels; and
each detector pixel is adapted to detect radiation from a different Fabry-Perot cavity filter position having different gap height.

9. The device of claim 7, wherein:
the channel selection filter is positioned between the photodetector array and the Fabry-Perot cavity filter.

10. The device of claim 7, wherein:
the first mirror is tilted with respect to the second mirror such that the gap varies in a continuous fashion as a function of width of the Fabry-Perot cavity filter; and
the first mirror and the second mirror comprise flat mirrors.

11. The device of claim 7, wherein the device comprises a color camera, a spectrum analyzer, a monochromator or an optical analyte detection system.

12. An optical filtering method, comprising:
passing incident radiation through a Fabry-Perot cavity filter comprising a first mirror and a second mirror, wherein a gap between the first and the second mirror monotonically varies as a function of width of the filter;
passing the incident radiation through a channel selection filter such that only one peak from the incident radiation that passes through Fabry-Perot cavity filter is incident on each pixel of a photodetector;
wherein the channel selection filter comprises a metal nanooptic filter array which comprises a plurality of subwavelength apertures in a metal film or between metal islands, such that a distance between the apertures in different regions of the metal nanooptic filter array is different; and
wherein the incident radiation is filtered by the channel selection filter based on plasmon resonance between the incident radiation and the metal film or metal islands of the channel selection filter.

13. The method of claim 12, wherein the first mirror is tilted with respect to the second mirror such that the gap varies in a continuous fashion along the width of the filter.

14. The method of claim 12, wherein the channel selection filter has a wider wavelength passband width than the Fabry-Perot cavity filter.

15. The method of claim 12, further comprising:
detecting radiation from the Fabry-Perot cavity filter position having a first gap height at a first photodetector pixel; and
detecting radiation from the Fabry-Perot cavity filter position having a second gap height different from the first gap height at a second photodetector pixel.

16. The method of claim 12, wherein the method comprises a spectrum analysis method, a color image formation method, a wavelength separation method or an optical analyte detection method.

17. The method of claim 12, wherein the incident radiation first passes through the Fabry-Perot filter and then through channel selection filter.

18. The device of claim 1, wherein the metal nanooptic filter array comprises a metal film.

19. The device of claim 7, wherein the metal nanooptic filter array comprises a metal film.

20. The device of claim 1, wherein the metal nanooptic filter array comprises metal islands.

21. The device of claim 7, wherein the metal nanooptic filter array comprises metal islands.

22. The method of claim 12, wherein the metal nanooptic filter array comprises a metal film.

23. The method of claim 12, wherein the metal nanooptic filter array comprises metal islands.

24. The method of claim 12, wherein at each location on the metal nanooptic filter array and on the Fabry-Perot cavity filter corresponding to one photodetector pixel, the Fabry-Perot cavity filter passes a set of wavelength peaks and the metal nanooptic filter array passes a wavelength band that overlaps with only one of the Fabry-Perot wavelength peaks.

* * * * *

UNITED STATES PATENT AND TRADEMARK OFFICE
CERTIFICATE OF CORRECTION

PATENT NO. : 7,426,040 B2  Page 1 of 1
APPLICATION NO. : 11/206900
DATED : September 16, 2008
INVENTOR(S) : Kim et al.

It is certified that error appears in the above-identified patent and that said Letters Patent is hereby corrected as shown below:

On the Title page,

Item [*] Notice: Subject to any disclaimer, the term of this patent is extended or adjusted under 35 USC 154(b) by 449 days Delete the phrase "by 449 days" and insert -- by 477 days --

Signed and Sealed this

Eighteenth Day of May, 2010

David J. Kappos
*Director of the United States Patent and Trademark Office*